US006387893B1

(12) United States Patent
Evans et al.

(10) Patent No.: US 6,387,893 B1
(45) Date of Patent: May 14, 2002

(54) SPIROTRICYCLIC SUBSTITUTED AZACYCLOALKANE DERIVATIVES AND USES THEREOF

(75) Inventors: Ben E. Evans; Jacob M. Hoffman, both of Lansdale; Kevin F. Gilbert, Barto; Kenneth E. Rittle, Green Lane, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/671,520

(22) Filed: Sep. 27, 2000

Related U.S. Application Data

(60) Provisional application No. 60/156,890, filed on Sep. 30, 1999.

(51) Int. Cl.[7] .................. A61K 31/55; A61K 31/54; C07D 223/10; C07D 239/02
(52) U.S. Cl. .............. 514/212.02; 514/211.03; 514/211.04; 514/212.04; 514/224.5; 514/267; 514/278; 540/485; 540/495; 540/543; 540/547; 544/249; 544/315; 544/318
(58) Field of Search ............. 514/211.03, 211.04, 514/212.02, 212.04, 224.5, 267, 278; 540/485, 495, 543, 547; 544/249, 315, 318

(56) References Cited

U.S. PATENT DOCUMENTS

| | | |
|---|---|---|
| 5,403,847 A | 4/1995 | Gluchowski et al. |
| 5,488,062 A | 1/1996 | Dunlap et al. |
| 5,578,611 A | 11/1996 | Gluchowski et al. |
| 5,610,174 A | 3/1997 | Craig et al. |
| 5,620,993 A | 4/1997 | Patane et al. |
| 5,661,163 A | 8/1997 | Patane et al. |

FOREIGN PATENT DOCUMENTS

| | | |
|---|---|---|
| EP | 0204597 | 5/1986 |
| EP | 0748800 | 12/1996 |
| WO | WO 92/00073 | 1/1992 |
| WO | WO 92/16213 | 10/1992 |
| WO | WO 94/08040 | 4/1994 |
| WO | WO 94/10989 | 5/1994 |
| WO | WO 94/22829 | 10/1994 |
| WO | WO 95/28397 | 10/1995 |
| WO | WO 96/14846 | 5/1996 |
| WO | WO96/39140 | 12/1996 |
| WO | WO 96/40135 | 12/1996 |
| WO | WO 96/40136 | 12/1996 |
| WO | WO 97/17969 | 5/1997 |
| WO | WO 97/42956 | 11/1997 |
| WO | WO 98/57632 | 12/1998 |
| WO | WO 98/57638 | 12/1998 |
| WO | WO 98/57639 | 12/1998 |
| WO | WO 98/57640 | 12/1998 |
| WO | WO 98/57641 | 12/1998 |
| WO | WO 98/57642 | 12/1998 |
| WO | WO 98/57940 | 12/1998 |

OTHER PUBLICATIONS

Watson & Girdlestone, "Receptor & Ion Channel Nomenclature Supplement", 1995.

Michel, et al., Naunyn–Schmiedeberg's Arch. Pharmacol., 352:1–10; 1995.

Mayor, et al, "The Synergic Nucleophilic and Electrophilic Properties of Carbenes. Synthesis of Carbazoles, Azafluorenes, o–Carbolines, and Pyrido–and Pyrimido[2,1–a]isoindoles by Carbene Rearrangement", Organic Chemistry, pp. 7467–7480 (1975).

P. Ting, et al., "Synthesis of Dibenzo[a,d]Cycloheptanes As Cytokine Biosynthesis Inhibitors", Bioorganic 7 Medicinal Chemistry Letters, vol. 5, No. 22, pp. 2749–2754 (1995).

S. Inagaki, "Mechanism of [2+2] Cycloaddition and Related Reactions between Electron Donors and Electron Acceptors. Perepoxide Quasi–Intermediate and Its Roles in the Reactions of 1g Molecular Oxygen with Olefins", Journal of the American Chemical Society, vol. 97:26, pp. 7480 (1975).

K. Kloc, et al., "Synthesis of Azafluorenones", Journal f. prakt. Chemie. Band, pp. 959–967, (1977).

M. A. Patane, "Potent and selective a–1B receptor antagonists", 214th ACS National Meeting & Exposition Program, Las Vegas, Nevada, Sep. 7–11, 1997 (Abstract).

D. Nagarathnam et al., "Design, synthesis and evaluation of hydropyrimidinones as a–1A selective antagonists 1: Identification of SNAP 5582 as a novel lead.", 214th ACS National Meeting & Exposition Program, Las Vegas, Nevada, Sep. 7–11, 1997 (Abstract).

D. Nagarathnam et al., "Design, synthesis and evalution of dihydropyrimidinones as a–1A selective antagonists 11: Structure–activity relationship of SNAP 5502 analogs", 214th ACS National Meeting & Exposition Program, Las Vegas, Nevada, Sep. 7–11, 1997 (Abstract).

(List continued on next page.)

Primary Examiner—Richard L. Raymond
Assistant Examiner—Tamthom N. Truong
(74) Attorney, Agent, or Firm—Baerbel R. Brown; Catherine D. Fitch; Kenneth R. Walton

(57) ABSTRACT

Spirotricyclic azacycloalkyl compounds and pharmaceutically acceptable salts thereof are disclosed. The synthesis of these compounds is also described. One application of these compounds, which are alpha 1a adrenergic receptor antagonists, is in the treatment of benign prostatic hyperplasia. These compounds are selective in their ability to relax smooth muscle tissue enriched in the alpha 1a receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia can be achieved.

23 Claims, No Drawings

OTHER PUBLICATIONS

M. R. Marzabadi et al., "Design, synthesis, and evalution of dihydropyrimidinones as a–1A selective antagonists 111: Modification of the piperidine moiety", 214th ACS National Meeting & Exposition Program, Las Vegas, Nevada, Sep. 7–11, 1997 (Abstract).

B. R. Lagu et al., "Design, synthesis, and evaluation of dihydropyrimidinoes as a–1A selective antagonists 1V: Dihydropyrimidone–fused lactones", 214th ACS National Meeting & Exposition Program, Las Vegas, Nevada, Sep. 7–11, 1997 (Abstract).

SPIROTRICYCLIC SUBSTITUTED AZACYCLOALKANE DERIVATIVES AND USES THEREOF

This application claims the benefit of U.S. Provisional No. 60/156,890 filed Sep. 30, 1999, the disclosure of which is hereby incorported by reference in its entirety.

FIELD OF THE INVENTION

This invention relates to spirotricyclic substituted azacycloalkane derivatives and pharmaceutically acceptable salts thereof, their synthesis, and their use as alpha 1a adrenoceptor antagonists. More particularly, the compounds of the present invention are useful for treating benign prostatic hyperplasia (BPH).

References are made throughout this application to various publications, the disclosures of which are hereby incorporated by reference in their entireties, in order to more fully describe the state of the art to which this invention pertains.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, $\beta_1$, and $\beta_2$ subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., α-*Adrenoreceptors: Molecular Biology, Biochemistry* and *Pharmacology,* (Progress in Basic and Clinical Pharmacology series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Michel et al., *Naunyn-Schmiedeberg's Arch. Pharmacol.* (1995), 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concommitantly, the increased noradrenergic innervation of the enlarged prostate leads to an increased adrenergic tone of the bladder neck and urethra, further restricting the flow of urine through the urethra.

In benign prostatic hyperplasia, the male hormone 5alpha-dihydrotestosterone has been identified as the principal culprit. The continual production of 5α-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.'s product PROSCAR® (finasteride). The effect of this compound is to inhibit the enzyme testosterone 5-α reductase, which converts testosterone into 5α-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/00073, the selective ability of the R(+) enantiomer of terazosin to bind to adrenergic receptors of the alpha 1 subtype was reported. In addition, in WO 92/16213, combinations of 5α-reductase inhibitory compounds and alpha1-adrenergic receptor blockers (terazosin, doxazosin, prazosin, bunazosin, indoramin, alfuzosin) were disclosed. However, no information as to the alpha 1d, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The relatively recent cloning of the human alpha 1a adrenergic receptor (ATCC CRL 11140) and the use of a screening assay utilizing the cloned human alpha 1a receptor has enabled identification of compounds which specifically interact with the human alpha 1a adrenergic receptor. For further description, see WO 94/08040 and WO 94/10989. As disclosed in the instant patent disclosure, a cloned human alpha 1a adrenergic receptor and a method for identifying compounds which bind the human alpha 1a receptor have made possible the identification of selective human alpha 1a adrenergic receptor antagonists useful for treating BPH.

Several classes of compounds have been disclosed to be selective alpha 1a adrenergic receptor antagonists useful for treating BPH. WO 94/22829 discloses, for example, certain 4-(un)substituted phenyl-1,4-dihydropyridine derivatives which are described as potent, selective alpha 1a antagonists with weak calcium channel antagonistic activity and which are further described to be anticipated as useful for treating BPH. As another example, WO 96/14846, WO 97/17969 and WO 97/42956 each disclose certain dihydropyrimidine derivatives (e.g., certain 1,2,3,6-tetrahydro-2-oxo-pyrimidine derivatives) which are selective antagonists for the human alpha 1a receptor and useful for treatment of BPH, impotency, cardiac arrhythmia, and other diseases where antagonism of the alpha 1a receptor may be useful. As still another example, WO 96/40135 discloses, inter alia, certain phenylpiperidinyl alkyl saccharin derivatives and their use as selective alpha 1a antagonists. Other examples are U.S. Pat. No. 5,661,163 and WO 96/40136, which disclose, inter alia, piperidinyl- and piperazinyl-alkyl-substituted phenyl acetamides. Yet another example is EP 748800, which discloses, inter alia, certain arylpiperazinyl-propyl substituted pyrimidinediones useful as alpha 1 adrenoceptor antagonists. Still other alpha 1a selective antagonist compounds are disclosed in WO 98/57632, WO 98/57638, WO 98/57639, WO 98/57640, WO 98/57641, WO 98/57642, and WO 98/57940.

The instant patent disclosure discloses novel spirotricyclic azacycloalkyl compounds (e.g., spirotricyclic azetidinyl, pyrrolidinyl, piperidinyl, etc. compounds) which bind to the human alpha 1a receptor. These compounds are further tested for binding to other human alpha 1 receptor subtypes, as well as counterscreened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still another object of the invention is to identify alpha 1a adrenergic receptor antagonists which are useful for relaxing lower urinary tract tissue in animals, preferably mammals, especially humans.

The compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The present invention provides spirotricyclic azacycloalkyl compounds and pharmaceutically acceptable salts thereof for the treatment of urinary obstruction caused by benign prostatic hyperplasia (BPH). The compounds antagonize the human alpha 1a adrenergic receptor at nanomolar and subnanomolar concentrations while typically exhibiting lower affinity for the alpha 1d and alpha 1b human adrenergic receptors and many other G-protein coupled receptors. This invention can have the advantage over non-selective alpha 1 adrenoceptor antagonists of reduced side effects related to peripheral adrenergic blockade. Such side effects include hypotension, syncope, lethargy, etc.

More particularly, the present invention is a compound of formula (I):

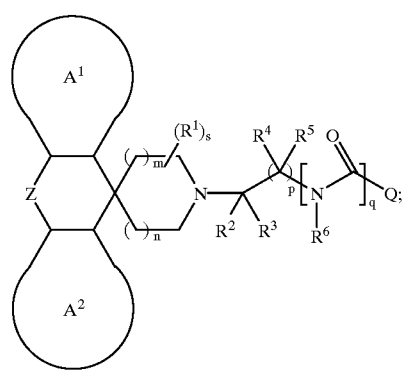

(I)

wherein Q is

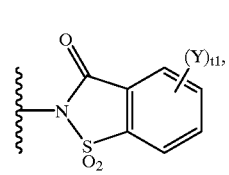

(i)

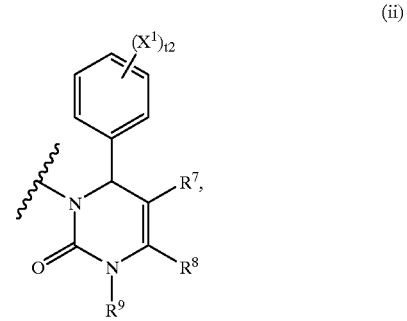

(ii)

-continued

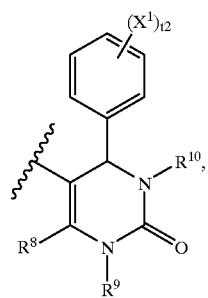
(iii)

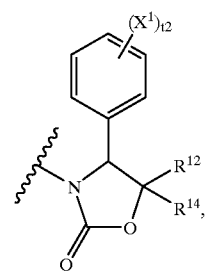
(iv)

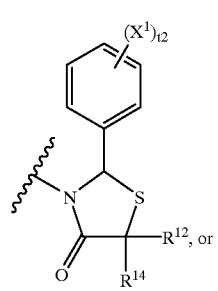
(v)

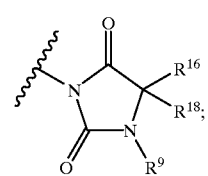
(vi)

$A^1$ is a benzene ring, substituted benzene, heterocyclic or substituted heterocyclic, wherein each of the substituents on substituted benzene or substituted heterocyclic is independently halogen, cyano, nitro, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalky;

$A^2$ independently has the same definition as set forth for $A^1$;

Z is absent, O, S, SO, $SO_2$, $NR^a$, C=O, $NR^aC(=O)$, $C(=O)NR^a$, $NR^aSO_2$, $SO_2NR^a$, $C(R^bR^c)$, $C(R^bR^c)C(R^bR^c)$, $C(R^b)=C(R^c)$, $C(R^bR^c)S$, $SC(R^bR^c)$, $C(R^bR^c)SO$, $SOC(R^bR^c)$, $C(R^bR^c)NR^a$, $NR^aC(R^bR^c)$, $C(R^bR^c)C(=O)$, or $C(=O)C(R^bR^c)$;

each Y is independently hydrogen, halogen, cyano, nitro, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalkyl;

each $X^1$ is independently hydrogen, halogen, cyano, nitro, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalkyl;

each $R^1$ is a substituent connected to a ring atom other than N or spiro subsituted carbon and is independently hydrogen or $C_1$–$C_4$ alkyl;

$R^2$, $R^3$, $R^4$ and $R^5$ are each independently selected from hydrogen, $C_1$–$C_6$ alkyl, and $C_3$–$C_8$ cycloalkyl;

$R^6$ is hydrogen, $C_1$–$C_8$ alkyl, or fluorinated $C_1$–$C_8$ alkyl;

$R^7$ and $R^8$ are each independently selected from hydrogen, halogen, cyano, $C_1$–$C_6$ alkyl, $C_1$–$C_6$ alkoxy, fluorinated $C_1$–$C_6$ alkyl, fluorinated $C_1$–$C_6$ alkoxy, $CO_2R^d$, $C_2$–$C_8$ alkoxyalkyl, and fluorinated $C_2$–$C_8$ alkoxyalkyl;

$R^9$ and $R^{10}$ are each independently selected from hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, $C_4$–$C_{20}$ cycloalkylalkyl, or $CHR^eR^f$;

$R^{12}$ and $R^{14}$ are each independently selected from hydrogen, $C_1$–$C_6$ alkyl, $C_3$–$C_8$ cycloalkyl, $C_1$–$C_6$ alkoxy, fluorinated $C_1$–$C_6$ alkyl, fluorinated $C_1$–$C_6$ alkoxy, fluorinated $C_3$–$C_8$ cycloalkyl, $C_2$–$C_8$ alkoxyalkyl, and fluorinated $C_2$–$C_8$ alkoxyalkyl; or one of $R^{12}$ and $R^{14}$ is $CO_2R^d$ or $CON(R^e)_2$ and the other of $R^{12}$ and $R^{14}$ is as earlier defined; or $R^{12}$ and $R^{14}$ together with the carbon atom to which they are attached form $C_3$–$C_7$ cycloalkyl or substituted $C_3$–$C_7$ cycloalkyl, wherein the each of the substituents on substituted cycloalkyl is independently halogen, cyano, $C_1$–$C_6$ alkyl, fluorinated $C_1$–$C_6$ alkyl, $C_1$–$C_6$ alkoxy, fluorinated $C_1$–$C_6$ alkoxy, $CO_2R^d$, $C_2$–$C_8$ alkoxyalkyl, or fluorinated $C_2$–$C_8$ alkoxyalkyl;

$R^{16}$ and $R^{18}$ are each independently selected from hydrogen, $C_1$–$C_6$ alkyl, phenyl, substituted phenyl, naphthyl, substituted naphthyl, heterocyclic, and substituted heterocyclic, provided that $R^{16}$ and $R^{18}$ are not both hydrogen; wherein each of the substituents on substituted phenyl or substituted naphthyl is independently halogen, $C_1$–$C_6$ alkyl, fluorinated $C_1$–$C_6$ alkyl, $C_1$–$C_6$ alkoxy, $CO_2R^d$, $C_2$–$C_8$ alkoxyalkyl, or fluorinated $C_2$–$C_8$ alkoxyalkyl; and wherein each of the substituents on substituted heterocyclic is independently halogen, $C_1$–$C_6$ alkyl, fluorinated $C_1$–$C_6$ alkyl, $C_1$–$C_6$ alkoxy, fluorinated $C_1$–$C_6$ alkoxy, $C_2$–$C_8$ alkoxyalkyl, fluorinated $C_2$–$C_8$ alkoxyalkyl, or phenyl;

$R^a$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, or $C_4$–$C_{20}$ cycloalkylalkyl;

$R^b$ and $R^c$ are each independently selected from hydrogen, $C_1$–$C_6$ alkyl, $C_3$–$C_6$ cycloalkyl, fluorinated $C_1$–$C_6$ alkyl, phenyl, and substituted phenyl, wherein each of the substituents on the substituted phenyl is independently halo, $C_1$–$C_6$ alkyl, fluorinated $C_1$–$C_6$ alkyl, $C_1$–$C_6$ alkoxy, fluorinated $C_1$–$C_6$ alkoxy, $CO_2R^d$, $C_2$–$C_8$ alkoxyalkyl, or fluorinated $C_2$–$C_8$ alkoxyalkyl;

$R^d$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, or $C_4$–$C_{20}$ cycloalkylalkyl;

$R^e$ is hydrogen or $C_1$–$C_6$ alkyl;

$R^f$ is phenyl or substituted phenyl, wherein each of the substituents on substituted phenyl is halogen, cyano, $C_1$–$C_6$ alkyl, fluorinated $C_1$–$C_6$ alkyl, $C_1$–$C_6$ alkoxy, fluorinated $C_1$–$C_6$ alkoxy, or $CO_2R^d$, $C_2$–$C_8$ alkoxyalkyl, or fluorinated $C_2$–$C_8$ alkoxyalkyl;

m and n are each independently integers from 0 to 3;

p is an integer from 1 to 5;

q is 0 or 1, provided that when Q is (iii)

then q is 0;

s is an integer from 0 to 4;

t1 is an integer from 0 to 4; and t2 is an integer from 0 to 5;

or a pharmaceutically acceptable salt thereof.

The present invention also includes pharmaceutical compositions, methods of preparing pharmaceutical compositions, and methods of treatment.

These and other embodiments, aspects and features of the present invention are either further described in or will be apparent from the ensuing description, examples and appended claims.

DETAILED DESCRIPTION OF THE INVENTION

The present invention includes spirotricyclic compounds of Formula (I) above. These compounds and their pharmaceutically acceptable salts are useful as alpha 1a antagonists.

A first embodiment of the present invention is a compound of Formula1a (I), wherein $A^1$ is a benzene ring, substituted benzene ring, heteroaryl, or substituted heteroaryl;

$A^2$ independently has the same definition as set forth for $A^1$;

Z is absent, O, S, SO, $SO_2$, $NR^a$, $C(R^bR^c)$, $C(R^bR^c)C(R^bR^c)$, or $C(R^b)=C(R^c)$;

one of $R^2$ and $R^3$ is hydrogen and the other of $R^2$ and $R^3$ is hydrogen, $C_1$–$C_6$ alkyl, or $C_3$–$C_8$ cycloalkyl;

one of $R^4$ and $R^5$ is hydrogen and the other of $R^4$ and $R^5$ is hydrogen, $C_1$–$C_6$ alkyl, or $C_3$–$C_8$ cycloalkyl;

$R^{16}$ and $R^{18}$ are each independently selected from hydrogen, $C_1$–$C_6$ alkyl, phenyl, substituted phenyl, naphthyl, substituted naphthyl, heterocyclic, and substituted heterocyclic, provided that $R^{16}$ and $R^{18}$ are not both hydrogen; wherein each heterocyclic is independently pyridyl, thienyl, or furanyl;

m and n are each integers from 0 to 3, provided that the sum of m and n is an integer less than or equal to 3;

and all other variables are as originally defined above;

or a pharmaceutically acceptable salt thereof.

A second embodiment of the present invention is a compound of formula (II):

(II)

wherein each $X^2$ is independently hydrogen, halogen, cyano, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalkyl;

w1 and w2 are each independently integers from 0 to 4;

and all other variables are as defined in the first embodiment;

or a pharmaceutically acceptable salt thereof.

A first class of the present invention is a compound of Formula (II), wherein Q is (ii)

(iv)

(v)

-continued

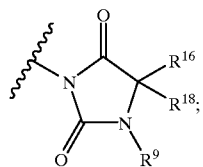

(vi)

and all other variables are as defined in the second embodiment;
or a pharmaceutically acceptable salt thereof A subclass of the preceding class is a compound of Formula (III):

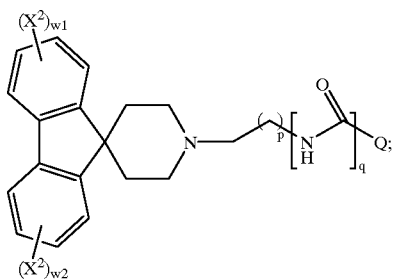

(III)

wherein
- $R^7$ and $R^8$ are each independently selected from hydrogen, halogen, cyano, $C_1$–$C_4$ alkyl, $C_1$–$C_4$ alkoxy, $(CH_2)_{0-4}CF_3$, $OCF_3$, $CO_2R^d$, $(CH_2)_{1-4}OCH_3$, and $(CH_2)_{1-4}OCF_3$;
- $R^9$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl;
- $R^{12}$ and $R^{14}$ are each independently selected from hydrogen, $C_1$–$C_4$ alkyl, $C_3$–$C_6$ cycloalkyl, $C_1$–$C_4$ alkoxy, $(CH_2)_{0-4}CF_3$, $OCF_3$, fluorinated $C_3$–$C_6$ cycloalkyl, $(CH_2)_{1-4}OCH_3$, $(CH_2)_{1-4}OCF_3$; or one of $R^{12}$ and $R^{14}$ is $CO_2R^d$ or $CON(R^e)_2$ and the other of $R^{12}$ and $R^{14}$ is as earlier defined; or $R^{12}$ and $R^{14}$ together with the carbon atom to which they are attached form $C_3$–$C_7$ cycloalkyl;
- one of $R^{16}$ and $R^{18}$ is hydrogen, $C_1$–$C_4$ alkyl, phenyl, mono- or di- or tri-substituted phenyl, naphthyl, mono- or di- or tri-substituted naphthyl, heterocyclic, or mono- or di- or tri-substituted heterocyclic; the other of $R^{16}$ and $R^{18}$ is phenyl, mono- or di- or tri-substituted phenyl, naphthyl, mono- or di- or tri-substituted naphthyl, heterocyclic, or mono- or di- or tri-substituted heterocyclic; wherein each of the substituents on substituted phenyl or substituted naphthyl or substituted heterocyclic is independently halogen, $C_1$–$C_4$ alkyl, $(CH_2)_{0-4}CF_3$, $C_1$–$C_4$ alkoxy, $OCF_3$, $CO_2R^d$, $(CH_2)_{1-4}OCH_3$, and $(CH_2)_{1-4}OCF_3$;
- $R^d$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl;
- $R^e$ is hydrogen or $C_1$–$C_4$ alkyl;
- p is an integer from 2 to 5;

and all other variables are as defined in the first class;
or a pharmaceutically acceptable salt thereof.

Exemplary of compounds of the second embodiment of the present invention are compounds selected from the group consisting of (+)-1'-{5-[((4(S)-(3,4-difluorophenyl)-2-oxo-oxazolidin)-3-yl)]-pentyl}-spirofluorene-9,4'-piperidine;
1'-[3-(5,5-bis-p-tolyl-2,4-dioxoimidazolidin-3-yl)propyl]spirofluorene-9,4'-piperidine;
1'-{6-[((4S)-(3,4-difluorophenyl)-2-oxooxazolidin)-3-yl]hexyl}-spirofluorene-9,4'-piperidine;
1'-{3-[(4S)-(3,4-difluorophenyl)-2-oxooxazolidin-3-carbonylamino]propyl}spirofluorene-9,4'-piperidine;
1'-{3-[(2S)-(3,4-difluorophenyl)-4-oxooxazolidin-3-carbonylamino]propyl}spirofluorene-9,4'-piperidine;
1,2,3,6-tetrahydro-1-[(spirofluorene-9,4'-piperidin-1'-yl)propyl]aminocarbonyl-5-methoxycarbonyl-4-methoxymethyl-6(S)-(3,4-difluorophenyl)-2-oxopyrimidine;
1'-[3-(5,5-bis-p-tolyl-2,4-dioxoimidazolidin-3-yl)propyl]-2-bromospirofluorene-9,4'-piperidine;
1,2,3,6-tetrahydro-1-[((2-bromospirofluorene-9,4'-piperidin)-1'-yl)propyl]aminocarbonyl-5-methoxycarbonyl-4-methoxymethyl-6(S)-(3,4-difluorophenyl)-2-oxopyrimidine;
1'-{3-[(4S)-(3,4-difluorophenyl)-2-oxooxazolidin-3-carbonylamino]propyl}-(2-bromospirofluorene-9,4'-piperidine);
1,2,3,6-tetrahydro-1-[((2-fluorospirofluorene-9,4'-piperidin)-1'-yl)propyl]aminocarbonyl-5-methoxycarbonyl-4-methoxymethyl-6(S)-(3,4-difluorophenyl)-2-oxopyrimidine;
1'-{3-[(4S)-(3,4-difluorophenyl)-2-oxooxazolidin-3-carbonylamino]propyl}-(2-fluorospirofluorene-9,4'-piperidine);

and pharmaceutically acceptable salts thereof.

A third embodiment of the present invention is a compound of Formula (IV):

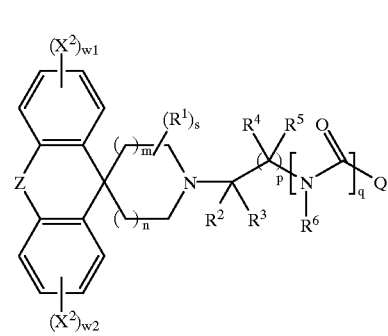

(IV)

wherein
- Z is O, S, SO, or $SO_2$;
- each $X^2$ is independently hydrogen, halogen, cyano, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalkyl;
- w1 and w2 are each independently integers from 0 to 4;

and all other variables are as defined in the first embodiment;
or a pharmaceutically acceptable salt thereof.

A second class of the invention is a compound of Formula (IV), wherein Q is

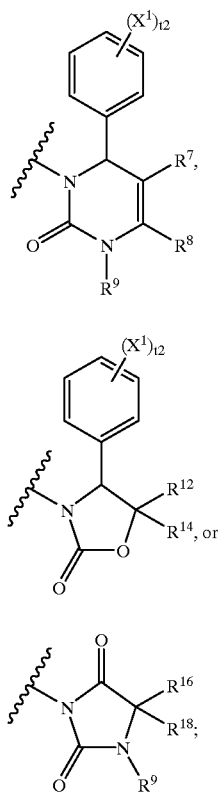

(ii)

(iv)

(vi)

and all other variables are as defined in the third embodiment;
or a pharmaceutically acceptable salt thereof.

A subclass of the preceding class is a compound of Formula (V):

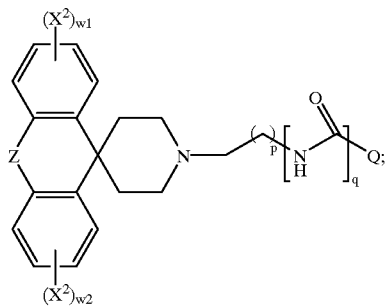

(V)

wherein
R$^7$ and R$^8$ are each independently selected from hydrogen, halogen, cyano, C$_1$–C$_4$ alkyl, C$_1$–C$_4$ alkoxy, (CH$_2$)$_{0-4}$CF$_3$, OCF$_3$, CO$_2$R$^d$, (CH$_2$)$_{1-4}$OCH$_3$, and (CH$_2$)$_{1-4}$OCF$_3$;
R$^9$ is hydrogen, C$_1$–C$_4$ alkyl, (CH$_2$)$_{0-4}$CF$_3$, C$_3$–C$_6$ cycloalkyl, or fluorinated C$_3$–C$_6$ cycloalkyl;
R$^{12}$ and R$^{14}$ are each independently selected from hydrogen, C$_1$–C$_4$ alkyl, C$_3$–C$_6$ cycloalkyl, C$_1$–C$_4$ alkoxy, (CH$_2$)$_{0-4}$CF$_3$, OCF$_3$, fluorinated C$_3$–C$_6$ cycloalkyl, (CH$_2$)$_{1-4}$OCH$_3$, (CH$_2$)$_{1-4}$OCF$_3$; or one of R$^{12}$ and R$^{14}$ is CO$_2$R$^d$ or CON(R$^e$)$_2$ and the other of R$^{12}$ and R$^{14}$ is as earlier defined; or R$^{12}$ and R$^{14}$ together with the carbon atom to which they are attached form C$_3$–C$_7$ cycloalkyl;
one of R$^{16}$ and R$^{18}$ is hydrogen, C$_1$–C$_4$ alkyl, phenyl, mono- or di- or tri-substituted phenyl, naphthyl, mono- or di- or tri-substituted naphthyl, heterocyclic, or mono- or di- or tri-substituted heterocyclic; the other of R$^{16}$ and R$^{18}$ is phenyl, mono- or di- or tri-substituted phenyl, naphthyl, mono- or di- or tri-substituted naphthyl, heterocyclic, or mono- or di- or tri-substituted heterocyclic; wherein each of the substituents on substituted phenyl or substituted naphthyl or substituted heterocyclic is independently halogen, C$_1$–C$_4$ alkyl, (CH$_2$)$_{0-4}$CF$_3$, C$_1$–C$_4$ alkoxy, OCF$_3$, CO$_2$R$^d$, (CH$_2$)$_{1-4}$OCH$_3$, and (CH$_2$)$_{1-4}$OCF$_3$;
R$^d$ is hydrogen, C$_1$–C$_4$ alkyl, (CH$_2$)$_{0-4}$CF$_3$, C$_3$–C$_6$ cycloalkyl, or fluorinated C$_3$–C$_6$ cycloalkyl;
R$^e$ is hydrogen or C$_1$–C$_4$ alkyl;
p is an integer from 2 to 5;
and all other variables are as defined in the second class;
or a pharmaceutically acceptable salt thereof.

Exemplary of compounds of the third embodiment of the present invention are compounds selected from the group consisting of 4-(S)-(+)-(3,4-difluorophenyl)-3-[4-(spirothioxanthen-9,4'-piperidin-1'-yl)-butyl]-oxazolidin-2-one;

4-(S)-(3,4-difluorophenyl)-3-[5-(spirothioxanthen-9,4'-piperidin-1'-yl)-pentyl]-oxazolidin-2-one;

4-(S)-(3,4-difluorophenyl)-3-[6-(spirothioxanthen-9,4'-piperidin-1'-yl)-hexyl]-oxazolidin-2-one;

1'-{3-[(4S)-(3,4-difluorophenyl)-2-oxooxazolidin-3-carbonylamino]propyl}-(spirothioxanthene-9,4'-piperidine);

1,2,3,6-tetrahydro-1-[(spirothioxanthene-9,4'-piperidin-1'-yl)propyl]aminocarbonyl-5-methoxycarbonyl-4-methoxymethyl-6(S)-(3,4-difluorophenyl)-2-oxopyrimidine;

1'-{3-[(4S)-(3,4-difluorophenyl)-2-oxooxazolidin-3-carbonylamino]propyl}-(10-oxo-spirothioxanthene-9,4'-piperidine);

1,2,3,6-tetrahydro-1-[(10-oxo-spirothioxanthene-9,4'-piperidin-1'-yl)propyl]aminocarbonyl-5-methoxycarbonyl-4-methoxymethyl-6(S)-(3,4-difluorophenyl)-2-oxopyrimidine;

1'-{3-[(4S)-(3,4-difluorophenyl)-2-oxooxazolidin-3-carbonylamino]propyl}-(10,10-dioxo-spirothioxanthene-9,4'-piperidine);

1,2,3,6-tetrahydro-1-[(10,10-dioxo-spirothioxanthene-9,4'-piperidin-1'-yl)propyl]aminocarbonyl-5-methoxycarbonyl-4-methoxymethyl-6(S)-(3,4-difluorophenyl)-2-oxopyrimidine;

1'-{3-[(4S)-(3,4-difluorophenyl)-2-oxooxazolidin-3-carbonylamino]propyl}spiroxanthene-9,4'-piperidine;

1,2,3,6-tetrahydro-1-[(spiroxanthene-9,4'-piperidin-1'-yl)propyl]aminocarbonyl-5-methoxycarbonyl-4-methoxymethyl-6(S)-(3,4-difluorophenyl)-2-oxopyrimidine;

1'-[3-(5,5-bis-p-tolyl-2,4-dioxoimidazolidin-3-yl)propyl]spiroxanthene-9,4'-piperidine;

1'-[3-(5,5-bis-p-tolyl-2,4-dioxoimidazolidin-3-yl)propyl]-2-chlorospiroxanthene-9,4'-piperidine;

1'-{3-[(4S)-(3,4-difluorophenyl)-2-oxooxazolidin-3-carbonylamino]propyl}-2-chlorospiroxanthene-9,4'-piperidine;

1,2,3,6-tetrahydro-1-[((2-chlorospiroxanthene-9,4'-piperidin)-1'-yl)propyl]aminocarbonyl-5-methoxycarbonyl-4-methoxymethyl-6(S)-(3,4-difluorophenyl)-2-oxopyrimidine;

1'-{3-[(4S)-(3,4-difluorophenyl)-2-oxooxazolidin-3-carbonylamino]propyl}-2,7-dichlorospiroxanthene-9,4'-piperidine;

1'-{3-[(4S)-(3,4-difluorophenyl)-2-oxooxazolidin-3-carbonylamino]propyl}-2,7-difluorospiroxanthene-9,4'-piperidine;

and pharmaceutically acceptable salts thereof.

A fourth embodiment of the present invention is a compound of Formula (VI):

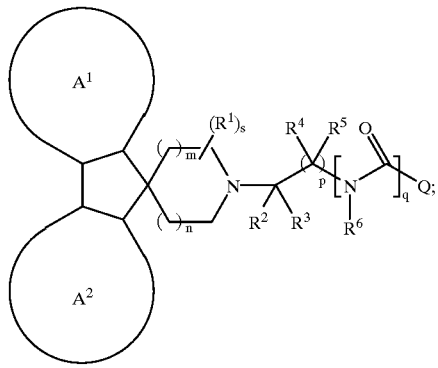

(VI)

wherein one of $A^1$ and $A^2$ is a benzene ring, substituted benzene ring, 6-membered heteroaryl, or substituted 6-membered heteroaryl; and the other of $A^1$ and $A^2$ is 6-membered heteroaryl or substituted 6-membered heteroaryl; wherein each heteroaryl ring has 1 or 2 nitrogen atoms and a balance of carbon atoms;

and all other variables are as defined in the first embodiment;

or a pharmaceutically acceptable salt thereof.

A third class of the present invention is a compound of Formula (VI), wherein Q is

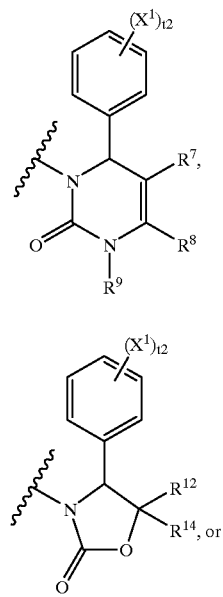

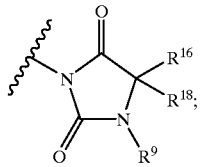

(vi)

and all other variables are as defined in the fourth embodiment;

or a pharmaceutically acceptable salt thereof.

A subclass of the preceding class is a compound of Formula (VII)

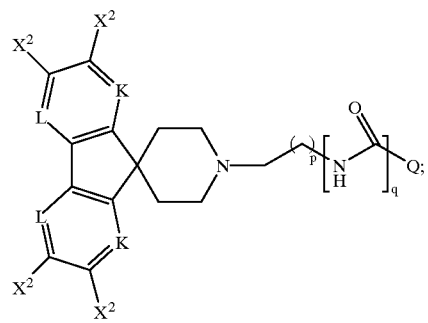

(VII)

wherein
K and L are each independently $CX^2$ or N, provided that at least one value K or L is N;

each $X^2$ is independently hydrogen, halogen, cyano, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalkyl;

$R^7$ and $R^8$ are each independently selected from hydrogen, halogen, cyano, $C_1$–$C_4$ alkyl, $C_1$–$C_4$ alkoxy, $(CH_2)_{0-4}CF_3$, $OCF_3$, $CO_2R^d$, $(CH_2)_{1-4}OCH_3$, and $(CH_2)_{1-4}OCF_3$;

$R^9$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl;

$R^{12}$ and $R^{14}$ are each independently selected from hydrogen, $C_1$–$C_4$ alkyl, $C_3$–$C_6$ cycloalkyl, $C_1$–$C_4$ alkoxy, $(CH_2)_{0-4}CF_3$, $OCF_3$, fluorinated $C_3$–$C_6$ cycloalkyl, $(CH_2)_{1-4}OCH_3$, $(CH_2)_{1-4}OCF_3$; or one of $R^{12}$ and $R^{14}$ is $CO_2R^d$ or $CON(R^e)_2$ and the other of $R^{12}$ and $R^{14}$ is as earlier defined; or $R^{12}$ and $R^{14}$ together with the carbon atom to which they are attached form $C_3$–$C_7$ cycloalkyl;

one of $R^{16}$ and $R^{18}$ is hydrogen, $C_1$–$C_4$ alkyl, phenyl, mono- or di- or tri-substituted phenyl, naphthyl, mono- or di- or tri-substituted naphthyl, heterocyclic, or mono- or di- or tri-substituted heterocyclic; the other of $R^{16}$ and $R^{18}$ is phenyl, mono- or di- or tri-substituted phenyl, naphthyl, mono- or di- or tri-substituted naphthyl, heterocyclic, or mono- or di- or tri-substituted heterocyclic; wherein each of the substituents on substituted phenyl or substituted naphthyl or substituted heterocyclic is independently halogen, $C_1$–$C_4$ alkyl, $(CH_2)_{0-4}CF_3$, $C_1$–$C_4$ alkoxy, $OCF_3$, $CO_2R^d$, $(CH_2)_{1-4}OCH_3$, and $(CH_2)_{1-4}OCF_3$;

$R^d$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl;

$R^e$ is hydrogen or $C_1$–$C_4$ alkyl;

p is an integer from 2 to 5;

and all other variables are as defined in the third class;

or a pharmaceutically acceptable salt thereof.

Exemplary of compounds of the fourth embodiment are compounds selected from the group consisting of 1'-{5-[(4(S)-(3,4-difluorophenyl)-2-oxooxazolidin)-3-yl]-pentyl}-(spiro-5H-indeno[1,2-b]pyridine)-5,4'-piperidine;

1'-{3-[(4S)-(3,4-difluorophenyl)-2-oxooxazolidin-3-carbonylamino]propyl}-(spiro-5H-indeno[1,2-b]pyridine)-5,4'-piperidine;

1,2,3,6-tetrahydro-1-[3-(spiro(5H-indeno[1,2-b]pyridine)-5,4'-piperidin)-1'-yl)propylaminocarbonyl]-5-methoxycarbonyl-4-methoxymethyl-6(S)-(3,4-difluorophenyl)-2-oxopyrimidine;

1'-{3-[(4S)-(3,4-difluorophenyl)-2-oxooxazolidin-3-carbonylamino]propyl}-(spiro-9H-indeno[2,1-b]pyridine)-9,4'-piperidine;

1,2,3,6-tetrahydro-1-[3-((spiro(9H-indeno[2,1-b]pyridine)-9,4'-piperidin)-1'-yl)propylaminocarbonyl]-5-methoxycarbonyl-4-methoxymethyl-6(S)-(3,4-difluorophenyl)-2-oxopyrimidine;

and pharmaceutically acceptable salts thereof.

A fifth embodiment of the present invention is a compound of Formula (VIII):

(VIII)

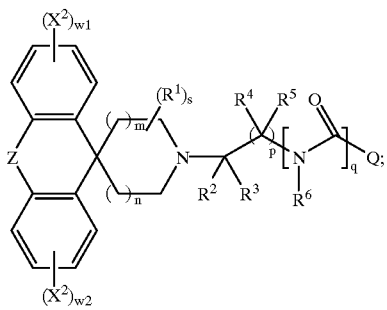

wherein

Z is $C(R^bR^c)$ or $C(R^bR^c)C(R^bR^c)$;

each $X^2$ is independently hydrogen, halogen, cyano, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalkyl;

w1 and w2 are each independently integers from 0 to 4;

and all other variables are as defined in the first embodiment;

or a pharmaceutically acceptable salt thereof.

A fourth class of the invention is a compound of Formula (VIII), wherein Q is (ii)

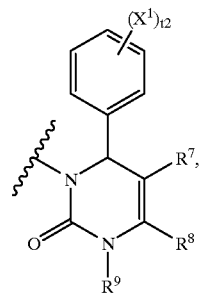

(iv)

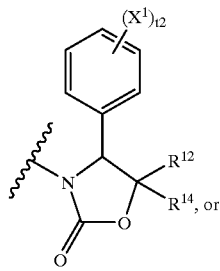

(vi)

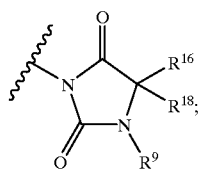

and all other variables are as defined in the fifth embodiment;

or a pharmaceutically acceptable salt thereof.

A subclass of the preceding class is a compound of Formula (IX):

(IX)

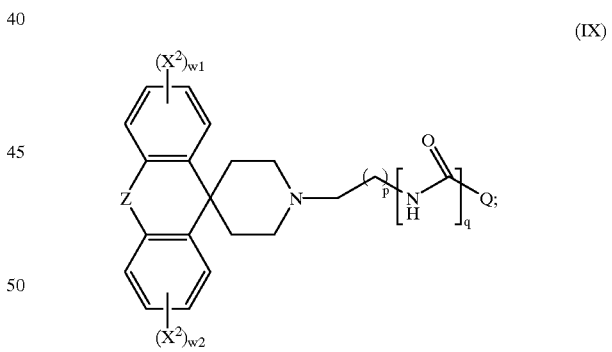

wherein

Z is $C(HR^b)$, $C(HR^b)C(HR^c)$, or $C(R^b)=C(R^c)$;

$R^7$ and $R^8$ are each independently selected from hydrogen, halogen, cyano, $C_1$–$C_4$ alkyl, $C_1$–$C_4$ alkoxy, $(CH_2)_{0-4}CF_3$, $OCF_3$, $CO_2R^d$, $(CH_2)_{1-4}OCH_3$, and $(CH_2)_{1-4}OCF_3$;

$R^9$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl;

$R^{12}$ and $R^{14}$ are each independently selected from hydrogen, $C_1$–$C_4$ alkyl, $C_3$–$C_6$ cycloalkyl, $C_1$–$C_4$ alkoxy, $(CH_2)_{0-4}CF_3$, $OCF_3$, fluorinated $C_3$–$C_6$ cycloalkyl, $(CH_2)_{1-4}OCH_3$, $(CH_2)_{1-4}OCF_3$; or one of $R^{12}$ and $R^{14}$ is $CO_2R^d$ or $CON(R^e)_2$ and the other of $R^{12}$ and $R^{14}$ is as earlier defined; or $R^{12}$ and $R^{14}$ together with the carbon atom to which they are attached form $C_3$–$C_7$ cycloalkyl;

one of $R^{16}$ and $R^{18}$ is hydrogen, $C_1$–$C_4$ alkyl, phenyl, mono- or di- or tri-substituted phenyl, naphthyl, mono- or di- or tri-substituted naphthyl, heterocyclic, or mono- or di- or tri-substituted heterocyclic; the other of $R^{16}$ and $R^{18}$ is phenyl, mono- or di- or tri-substituted phenyl, naphthyl, mono- or di- or tri-substituted naphthyl, heterocyclic, or mono- or di- or tri-substituted heterocyclic; wherein each of the substituents on substituted phenyl or substituted naphthyl or substituted heterocyclic is independently halogen, $C_1$–$C_4$ alkyl, $(CH_2)_{0-4}CF_3$, $C_1$–$C_4$ alkoxy, $OCF_3$, $CO_2R^d$, $(CH_2)_{1-4}OCH_3$, and $(CH_2)_{1-4}OCF_3$;

each $R^b$ and each $R^c$ is independently hydrogen, $C_1$–$C_4$ alkyl, $C_3$–$C_6$ cycloalkyl, $(CH_2)_{0-4}CF_3$, phenyl, or substituted phenyl, wherein each of the substituents on substituted phenyl is independently halogen, $C_1$–$C_4$ alkyl, $(CH_2)_{0-4}CF_3$, $C_1$–$C_4$ alkoxy, $OCF_3$, $CO_2R^d$, $(CH_2)_{0-4}OCH_3$, or $(CH_2)_{0-4}OCF_3$;

$R^d$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl;

$R^e$ is hydrogen or $C_1$–$C_4$ alkyl;

p is an integer from 2 to 5;

and all other variables are as defined in the fourth class; or a pharmaceutically acceptable salt thereof.

Exemplary compounds of the fifth embodiment are compounds selected from the group consisting of 1,2,3,6-tetrahydro-1-[3-((10,11-dihydrospiro-5H-dibenzo[a,d] cycloheptene-5,4'-piperidin)-1'-yl)propylaminocarbonyl]-5-methoxycarbonyl-4-methoxymethyl-6(S)-(3,4-difluorophenyl)-2-oxopyrimidine;

1'-{3-[4(S)-(3,4-difluorophenyl)-2-oxooxazolidin-3-carbonylamino]-propyl}-(10,11-dihydrospiro-5H-dibenzo[a,d] cycloheptene)-5,4'-piperidine;

1'-{5-[4(S)-(3,4-difluorophenyl)-2-oxooxazolidin-3-yl]-pentyl}-(10,11-dihydrospiro-5H-dibenzo[a,d] cycloheptene)-5,4'-piperidine;

and pharmaceutically acceptable salts thereof.

A preferred aspect of the present invention is 1,2,3,6-tetrahydro-1-[3-((spiro(9H-indeno[2,1-b]pyridine)-9,4'-piperidin)-1'-yl)-propylaminocarbonyl]-5-methoxycarbonyl-4-methoxymethyl-6(S)-(3,4-difluorophenyl)-2-oxopyrimidine (Example 53 below), or a pharmaceutically acceptable salt thereof.

The present invention also includes a pharmaceutical composition comprising a therapeutically effective amount of any of the compounds described above and a pharmaceutically acceptable carrier. In one embodiment is a pharmaceutical composition made by combining any of the compounds described above and a pharmaceutically acceptable carrier. The present invention further includes a process for making a pharmaceutical composition comprising combining any of the compounds described above and a pharmaceutically acceptable carrier.

The present invention further includes a pharmaceutical composition as described in the preceding paragraph further comprising a therapeutically effective amount of a testosterone 5-alpha reductase inhibitor. In one embodiment, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor), or a dual type 1 and type 2 testosterone 5-alpha reductase inhibitor. In another embodiment, the testosterone 5-alpha reductase inhibitor is a type 2 testosterone 5-alpha reductase inhibitor. The testosterone 5-alpha reductase inhibitor is suitably finasteride.

The present invention also includes a method of treating benign prostatic hyperplasia in a subject in need thereof which comprises administering to the subject a therapeutically effective amount of any of the compounds (or any of the compositions) described above. In one embodiment of the method of treating BPH, the compound (or composition) does not cause a fall in blood pressure at dosages effective to alleviate BPH. In another embodiment of the method of treating BPH, the compound is administered in combination with a testosterone 5-alpha reductase inhibitor. A suitable testosterone 5-alpha reductase inhibitor for use in the method is finasteride.

The present invention also includes a method of inhibiting contraction of prostate tissue or relaxing lower urinary tract tissue in a subject in need thereof which comprises administering to the subject a therapeutically effective amount of any of the compounds (or any of the compositions) described above. In one embodiment of the method of inhibiting contraction of prostate tissue or relaxing lower urinary tract tissue, the compound (or composition) additionally does not cause a fall in blood pressure at dosages effective to inhibit contraction of prostate tissue. In another embodiment, the compound is administered in combination with a therapeutically effective amount of a testosterone 5-alpha reductase inhibitor; the testosterone 5-alpha reductase inhibitor is suitably finasteride.

The present invention also includes a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see Vatz, *Headache* (1997), 37: 107–108) and cardiac arrhythmia.

The present invention also includes a method of preventing or treating prostatic cancer which comprises administering to a subject in need of prevention or treatment thereof a therapeutically effective amount of a combination comprising any of the compounds (or compositions) described above and a testosterone 5-alpha-reductase inhibitor. The testosterone 5-alpha reductase inhibitor is suitably finasteride.

The present invention also includes the use of any of the compounds described above in the preparation of a medicament for: a) treating benign prostatic hyperplasia; b) relaxing lower urinary tract tissue; or c) inhibiting contraction of prostate tissue; in a subject in need thereof.

The present invention further includes the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

As used herein, the term "$C_1$–$C_8$ alkyl" means linear or branched chain alkyl groups having from 1 to 8 carbon atoms and includes all of the octyl alkyl, heptyl alkyl, hexyl alkyl and pentyl alkyl isomers as well as n-, iso-, sec- and t-butyl, n- and isopropyl, ethyl and methyl. "$C_1$–$C_6$ alkyl" means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl.

The term "$C_1$–$C_6$ alkoxy" means an —O—alkyl group wherein alkyl is $C_1$–$C_6$ alkyl, as defined above. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy.

The term "$C_2$–$C_8$ alkoxyalkyl" means a linear or branched $C_1$–$C_6$ alkyl group as defined above having as a substituent a $C_1$–$C_6$ alkoxy group as defined above, wherein the alkoxyalkyl group has a total of from 2 to 8 carbon atoms. Representative examples of suitable alkoxyalkyl groups include, but are not limited to, the $C_1$–$C_6$ alkoxy-substituted methyl groups (methoxymethyl, ethoxymethyl, n-propoxymethyl, isopropoxymethyl, and the butyloxymethyl, pentyloxymethyl, and hexyloxymethyl isomers), and the $C_1$–$C_6$ alkoxy-substituted ethyl groups. Other suitable alkoxyalkyl groups include the series $(CH_2)_{1-6}OCH_3$, $(CH_2)_{1-4}OCH_3$, $(CH_2)_{1-6}OCH_2CH_3$, and $(CH_2)_{1-4}OCH_2CH_3$.

The term "$C_3$–$C_8$ cycloalkyl" means a cyclic ring of an alkane having three to eight total carbon atoms (i.e., cyclopropyl, cyclobutyl, cyclopentyl, cyclohexyl, cycloheptyl or cyclooctyl). "$C_3$–$C_7$ cycloalkyl" refers to a cyclic ring selected from cyclopropyl, cyclobutyl, cyclopentyl, cyclohexyl, and cycloheptyl. "$C_3$–$C_6$ cycloalkyl" refers to a cyclic ring selected from cyclopropyl, cyclobutyl, cyclopentyl, and cyclohexyl.

The term "$C_4$–$C_{20}$ alkylcycloalkyl" means a $C_3$–$C_8$ cycloalkyl as defined above substituted with one or more $C_1$–$C_8$ alkyl groups as defined above, wherein the total number of carbon atoms in the alkylcycloalkyl group is in the range of from 4 to 20. "$C_6$–$C_{14}$ alkylcycloalkyl" means a $C_3$–$C_6$ cycloalkyl as defined above substituted with one or more $C_1$–$C_4$ alkyl groups as defined above, wherein the total number of carbon atoms in the alkylcycloalkyl group is in the range of from 6 to 14. Representative examples include methylcyclohexyl (i.e., 2-, 3- and 4-methylcyclohexyl), ethylcyclohexyl, methylcyclopentyl, dimethylcyclohexyl (i.e., 2,3-, 2,4-, 2,5-, 2,6-, 3,4-, and 3,5-dimethylcyclohexyl), methylcyclobutyl, and so forth.

The term "$C_4$–$C_{20}$ cycloalkylalkyl" means a $C_1$–$C_8$ alkyl group as defined above substituted with one or more $C_3$–$C_8$ cycloalkyls as defined above, wherein the total number of carbon atoms in the cycloalkyl alkyl group is in the range of from 4 to 20. "$C_6$–$C_{14}$ cycloalkyl-alkyl" means a $C_1$–$C_4$ alkyl group as defined above substituted with one or more $C_3$–$C_6$ cycloalkyl groups as defined above, wherein the total number of carbon atoms in the alkylcycloalkyl group is in the range of from 5 to 14. Representative examples include cyclohexylmethyl, 1- and 2-cyclohexylethyl, cyclohexylisopropyl, 1- and 3-cyclohexyl-n-propyl, dicyclohexylmethyl, and so forth.

The term "halogen" (which may alternatively be referred to as "halo") refers to fluorine, chlorine, bromine and iodine (alternatively, fluoro, chloro, bromo, and iodo).

The term "fluorinated $C_1$–$C_8$ alkyl" (which may alternatively be referred to as "$C_1$–$C_8$ fluoroalkyl") means a $C_1$ to $C_8$ linear or branched alkyl group as defined above with one or more fluorine substituents. The terms "fluorinated $C_1$–$C_4$ alkyl" and "fluorinated $C_1$–$C_6$ alkyl" have analogous meanings. Representative examples of suitable fluoroalkyls include the series $(CH_2)_{0-4}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "fluorinated $C_3$–$C_8$ cycloalkyl" (which may alternatively be referred to as "$C_3$–$C_8$ fluorocycloalkyl") means a cycloalkyl group as defined above with one or more fluorine substituents. The terms "fluorinated $C_3$–$C_7$ cycloalkyl" and "fluorinated $C_3$–$C_6$ cycloalkyl" have analogous meanings. Representative examples of suitable fluorocycloalkyls include all isomers of fluorocyclohexyl (i.e., 1-, 2-, 3-, and 4-fluorocyclohexyl), difluorocyclohexyl (e.g., 2,4-difluorocyclohexyl, 3,4-difluorocyclohexyl, etc.), fluorocyclopentyl, and so forth.

The term "fluorinated $C_1$–$C_6$ alkoxy" (which may alternatively be referred to as "$C_1$–$C_6$ fluoroalkyl") means a $C_1$–$C_6$ alkoxy group as defined above wherein the alkyl moiety has one or more fluorine substituents. The term "fluorinated $C_1$–$C_4$ alkoxy" has an analogous meaning. Representative examples include the series $O(CH_2)_{0-4}CF_3$ (i.e., trifluoromethoxy, 2,2,2-trifluoroethoxy, 3,3,3-trifluoro-n-propoxy, etc.), 1,1,1,3,3,3-hexafluoroisopropoxy, and so forth.

The term "fluorinated $C_2$–$C_8$ alkoxyalkyl" means $C_2$–$C_8$ alkoxyalkyl as defined above, wherein either or both the alkoxy moiety and the alkyl moiety has one or more fluorine substituents. Representative examples of suitable fluorinated alkoxyalkyl groups include, but are not limited to, the $C_1$–$C_6$ fluoroalkoxy-substituted methyl groups (e.g., fluoromethoxymethyl, 2-fluoroethoxymethyl, and 3-fluoro-n-propoxymethyl), $C_1$–$C_6$ difluoroalkoxymethyl groups (e.g., difluoromethoxymethyl and 2,2-difluoroethoxymethyl), $C_1$–$C_6$ trifluoroalkoxy-substituted methyl groups (e.g., trifluoromethoxymethyl and 2,2,2-trifluoroethoxymethyl), $C_1$–$C_6$ alkoxy-substituted fluoromethyl groups (e.g., methoxy- or ethoxy-fluoromethyl), and $C_1$–$C_6$ alkoxy-substituted difluoromethyl groups (e.g., methoxy- or ethoxy-difluoromethyl). Other suitable fluorinated alkoxyalkyl groups include the series $(CH_2)_{1-6}OCF_3$, $(CH_2)_{1-4}OCF_3$, $(CH_2)_{1-6}OCH_2CF_3$, and $(CH_2)_{1-4}OCH_2CF_3$.

The term "heterocyclic" (which may alternatively be referred to as "heterocycle") refers to a stable 5- to 7-membered monocyclic ring system which may be saturated or unsaturated; which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any single heteroatom or carbon atom, or with respect to the definitions of $A^1$ and $A^2$ may be fused to another ring system by two adjacent ring carbon atoms, provided that attachment or fusion results in the creation of a stable structure. Suitable heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl, and triazolyl. Morpholino is the same as morpholinyl.

The term "thienyl," as used herein, refers to the group

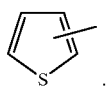

"Fused thienyl" refers to

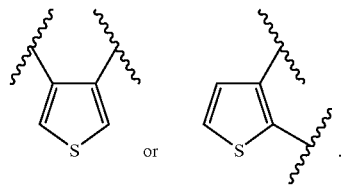

The term "substituted heterocyclic" refers to a heterocyclic group as defined above having one or more subsituents independently selected from halogen, cyano, $C_1$–$C_6$ alkyl, fluorinated $C_1$–$C_6$ alkyl, $C_1$–$C_6$ alkoxy, fluorinated $C_1$–$C_6$ alkoxy, $C_2$–$C_8$ alkoxyalkyl, fluorinated $C_2$–$C_8$ alkoxyalkyl, $C_3$–$C_8$ cycloalkyl, fluorinated $C_3$–$C_8$ cycloalkyl, amino, N—($C_1$–$C_6$ alkyl)amino, N,N-di-($C_1$–$C_6$ alkyl)amino, aryl (defined below), carboxy, $C_1$–$C_6$ alkoxycarbonyl, sulfonamido, sulfonyl, and the like.

The term "aryl" refers herein to aromatic mono- and poly-carbocyclic ring systems, wherein the carbocyclic rings in the polyring systems may be fused or attached via a single ring carbon. Suitable aryl groups include, but are not limited to, phenyl, naphthyl, and biphenylenyl.

"Substituted aryl" refers to aryl groups as defined above having one or more substituents independently selected from halogen, cyano, $C_1$–$C_6$ alkyl, fluorinated $C_1$–$C_6$ alkyl, $C_1$–$C_6$ alkoxy, fluorinated $C_1$–$C_6$ alkoxy, $C_2$–$C_8$ alkoxyalkyl, fluorinated $C_2$–$C_8$ alkoxyalkyl, $C_3$–$C_8$ cycloalkyl, fluorinated $C_3$–$C_8$ cycloalkyl, amino, N-$C_1$–$C_6$ alkylamino, N,N-di-($C_1$–$C_6$)alkylamino, aryl, carboxy, $C_1$–$C_6$ alkoxycarbonyl, sulfonamido, sulfonyl, and the like.

The term "heteroaryl" refers to the subset of heterocycles as heretofore defined which are aromatic heterocyclic ring systems, including, but not limited to, pyridyl, pyrazinyl, thienyl, thiazolyl, furanyl, imidazolyl, pyrazolyl, triazolyl, oxadiazolyl, oxazolyl, thiazolyl, and thiadiazolyl.

"Substituted heteroaryl" refers to heteroaryl groups as defined above having one or more substituents as defined above.

The term "substituted" includes mono- and poly-substitution by a named substituent to the extent such single and multiple substitution is chemically allowed.

The expression "Z is absent" means that Z is replaced by a bond; i.e., ring $A^1$ in Formula (I) is fused to a cyclopentyl moiety.

It is understood that the definition of a substituent (e.g., $CO_2R^d$) or variable (e.g., $R^d$) at a particular location in a molecule is independent of its definitions at other locations in that molecule. Thus, for example, when $R^7$ is $CO_2R^d$=$CO_2H$, and $R^8$ is $CO_2R^d$, it is understood that $R^8$ can be any one of $CO_2H$, $CO_2Me$, $CO_2Et$, $CO_2Pr$, etc. As another example, the moiety

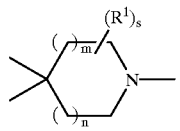

wherein $R^1$ is hydrogen or $C_1$–$C_4$ alkyl, m=1, n=1, and s=2, represents moieties such as

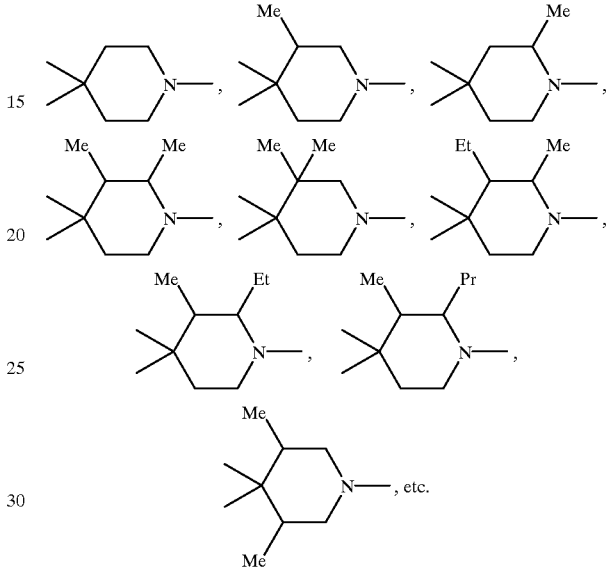

It is also understood that the definition of a substituent or variable at a particular location in a molecule is dependent of the definition of another occurrence of the same substituent or variable at the same location. Thus, $C(=O)N(R^e)_2$ represents groups such as —$C(=O)NH_2$, —$C(=O)NHCH_3$, —$C(=O)NHC_2H_5$, —$C(=O)N(CH_3)C_2H_5$, etc.

It is understood that substituents and substitution patterns on the compounds of the instant invention can be selected by one of ordinary skill in the aft to provide compounds that are chemically stable and that can be readily synthesized by the methods set forth below and, when viewed in the light of this disclosure, by techniques known in the art. Where multiple substituent moieties are disclosed or claimed, the substituted compound can be independently substituted by one or more of the disclosed or claimed substituent moieties, singly or plurally.

Representative embodiments for the variables and substituents set forth in Formula (I) include the following:

$A^1$ is a benzene ring (i.e., benzo), substituted benzene ring (i.e., substituted benzo), heteroaryl, or substituted heteroaryl, wherein the heteroaryl has from 1 to 2 heteroatoms selected from N, O and S; or $A^1$ is benzo or mono- or di- or tri-substituted benzo, wherein each of the substituents on substituted benzo is independently halogen, cyano, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalkyl; or $A^1$ is heteroaryl or substituted heteroaryl, wherein the heteroaryl has 1 to 2 N atoms and the remaining atoms in the heteroaryl ring are carbon atoms, and each of the substituents on substituted heteroaryl is as previously set forth in this paragraph for substituted benzo; or $A^1$ is 6-membered heteroaryl or substituted 6-membered heteroaryl, wherein each of the substituents on substituted heteroaryl is as set forth earlier in this paragraph for substituted benzo.

$A^2$ independently has the same definition as set forth for $A^1$. In one embodiment, one of $A^1$ and $A^2$ is benzo or substituted benzo, and the other of $A^1$ and $A^2$ is heteroaryl or substituted heteroaryl. In another embodiment, each of $A^1$ and $A^2$ is independently benzo or substituted benzo. In an aspect of the preceding embodiment, $A^1$ is

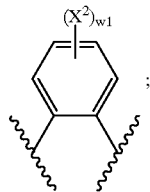

and $A^2$ is

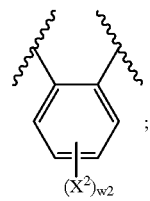

wherein each $X^2$ is independently hydrogen, halogen, cyano, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalkyl; and w1 and w2 are each independently integers from 0 to 4. In one aspect of this embodiment, each $X^2$ is independently hydrogen, halogen, $C_1$–$C_4$ alkyl, $(CH_2)_{0-4}CF_3$, $C_1$–$C_4$ alkoxy, $OCF_3$, $CO_2R^d$, $(CH_2)_{1-4}OCH_3$, or $(CH_2)_{1-4}CF_3$. In other aspects, w1 and w2 are each independently integers from 0 to 3; or from 0 to 2.

Z is absent, O, S, SO, $SO_2$, $NR^a$, $C(R^bR^c)$, $C(R^bR^c)C(R^bR^c)$, or $C(R^b)=C(R^c)$; or is absent, O, S, SO, $SO_2$, $NR^a$, $C(R^bR^c)$, or $C(R^bR^c)C(R^bR^c)$; or is absent, O, S, SO, $SO_2$, $CH_2$, or $CH_2CH_2$.

Each of $X^1$ and Y is independently hydrogen, halogen, cyano, $C_1$–$C_6$ alkyl, $C_1$–$C_4$ alkoxy, $C_3$–$C_7$ cycloalkyl, fluorinated $C_1$–$C_6$ alkyl, fluorinated $C_1$–$C_4$ alkoxy, fluorinated $C_3$–$C_7$ cycloalkyl, $C_2$–$C_8$ alkoxyalkyl, or fluorinated $C_2$–$C_8$ alkoxyalkyl; or is independently hydrogen, fluorine, chlorine, cyano, $C_1$–$C_4$ alkyl, $C_3$–$C_6$ cycloalkyl, fluorinated $C_1$–$C_6$ alkyl, fluorinated $C_3$–$C_6$ cycloalkyl, $(CH_2)_{0-4}OCH_3$, or $(CH_2)_{0-4}OCF_3$; or is hydrogen, fluorine, chlorine, cyano, methyl, ethyl, $OCF_3$, $CH_2CF_3$, $(CH_2)_{0-2}OCH_3$, and $(CH_2)_{0-2}OCF_3$; or is hydrogen, fluorine, chlorine, cyano, methyl, ethyl, $CF_3$, $CH_2CF_3$, $(CH_2)_{1-2}OCH_3$, and $(CH_2)_{1-2}OCF_3$.

each $R^1$ is a substituent connected to a ring atom other than the spiro subsituted carbon or the N and is independently hydrogen, methyl or ethyl.

$R^2$, $R^3$, $R^4$ and $R^5$ are each independently selected from hydrogen and $C_1$–$C_6$ alkyl. In one embodiment, one of $R^2$ and $R^3$ is hydrogen and the other of $R^2$ and $R^3$ is hydrogen, $C_1$–$C_6$ alkyl, or $C_3$–$C_8$ cycloalkyl; and one of $R^4$ and $R^5$ is hydrogen and the other of $R^4$ and $R^5$ is hydrogen, $C_1$–$C_6$ alkyl, or $C_3$–$C_8$ cycloalkyl. In another embodiment, $R^2$, $R^3$, $R^4$ and $R^5$ are all hydrogen.

$R^6$ is hydrogen, $C_1$–$C_4$ alkyl, or fluorinated $C_1$–$C_4$ alkyl; or is hydrogen.

$R^7$ and $R^8$ are each independently selected from hydrogen, halogen, cyano, $C_1$–$C_4$ alkyl, $C_1$–$C_4$ alkoxy, $(CH_2)_{0-4}CF_3$, $OCF_3$, $CO_2R^d$, $(CH_2)_{1-4}OCH_3$, and $(CH_2)_{1-4}OCF_3$.

$R^9$ and $R^{10}$ are each independently hydrogen, $C_1$–$C_4$ alkyl, $(CH_2)_{0-4}CF_3$, $C_3$–$C_6$ cycloalkyl, or fluorinated $C_3$–$C_6$ cycloalkyl.

$R^{12}$ and $R^{14}$ are each independently selected from hydrogen, $C_1$–$C_4$ alkyl, $C_3$–$C_6$ cycloalkyl, $C_1$–$C_4$ alkoxy, $(CH_2)_{0-4}CF_3$, $OCF_3$, fluorinated $C_3$–$C_6$ cycloalkyl, $(CH_2)_{1-4}OCH_3$,$(CH_2)_{1-4}OCF_3$; or one of $R^{12}$ and $R^{14}$ is $CO_2R^d$ or $CON(R^e)_2$ and the other of $R^{12}$ and $R^{14}$ is as earlier defined; or $R^{12}$ and $R^{14}$ together with the carbon atom to which they are attached form $C_3$–$C_7$ cycloalkyl.

One of $R^{16}$ and $R^{18}$ is hydrogen, $C_1$–$C_4$ alkyl, phenyl, mono-or di- or tri-substituted phenyl, naphthyl, mono- or di- or tri-substituted naphthyl, heterocyclic, or mono- or di- or tri-substituted heterocyclic; the other of $R^{16}$ and $R^{18}$ is phenyl, mono- or di- or tri-substituted phenyl, naphthyl, mono- or di- or tri-substituted naphthyl, heterocyclic, or mono- or di- or tri-substituted heterocyclic; wherein each of the substituents on substituted phenyl or substituted naphthyl or substituted heterocyclic is independently halogen, $C_1$–$C_4$ alkyl, $(CH_2)_{0-4}CF_3$, $C_1$–$C_4$ alkoxy, $OCF_3$, $CO_2R^d$, $(CH_2)_{1-4}OCH_3$, or $(CH_2)_{1-4}OCF_3$.

$R^a$ is hydrogen, $C_1$–$C_4$ alkyl, fluorinated $C_1$–$C_4$ alkyl, $C_3$–$C_6$ cycloalkyl, fluorinated $C_3$–$C_6$ cycloalkyl, $C_6$–$C_{14}$ alkylcycloalkyl, or $C_6$–$C_{14}$ cycloalkylalkyl; or is hydrogen, $C_1$–$C_4$ alkyl, or $(CH_2)_{0-4}CF_3$; or is hydrogen, methyl, ethyl, or $CF_3$; or is hydrogen.

One of $R^b$ and $R^c$ is hydrogen, and the other of $R^b$ and $R^c$ is hydrogen, $C_1$–$C_4$ alkyl, $C_3$–$C_6$ cycloalkyl, fluorinated $C_1$–$C_4$ alkyl, phenyl, or substituted phenyl, wherein each of the substituents on the substituted phenyl is independently halogen, $C_1$–$C_4$ alkyl, fluorinated $C_1$–$C_4$ alkyl, $C_1$–$C_4$ alkoxy, fluorinated $C_1$–$C_4$ alkoxy, $CO_2R^d$, $C_2$–$C_8$ alkoxyalkyl, or fluorinated $C_2$–$C_8$ alkoxyalkyl. In another embodiment, $R^b$ and $R^c$ are both hydrogen.

$R^d$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl; or is hydrogen, methyl, ethyl, or $(CH_2)_{0-2}CF_3$.

$R^e$ is hydrogen or $C_1$–$C_4$ alkyl; or is hydrogen, methyl, or ethyl; or is hydrogen.

$R^f$ is phenyl or substituted phenyl, wherein each of the substituents on substituted phenyl is halogen, cyano, $C_1$–$C_4$ alkyl, fluorinated $C_1$–$C_4$ alkyl, $C_1$–$C_4$ alkoxy, fluorinated $C_1$–$C_4$ alkoxy, $CO_2R^d$, $C_2$–$C_8$ alkoxyalkyl, or fluorinated $C_2$–$C_8$ alkoxyalkyl.

m and n are each integers from 0 to 3, provided that the sum of m and n is an integer less than or equal to 3. In another embodiment m and n are each independently integers from 0 to 1. In still another embodiment m and n are both 1.

p is an integer from 2 to 5; or from 2 to 4; or is 2; or is 3; or is 4.

s is an integer from 0 to 2; or is 1; or is 0.

t1 is an integer from 0 to 3; or from 0 to 2; or is 0 or 1.

t2 is an integer from 0 to 3; or from 0 to 2; or is 0 or 1.

The compounds of the present invention typically exhibit selectivity for the human alpha 1a adrenergic receptor. One implication of this selectivity is that these compounds display selectivity for lowering intraurethral pressure without substantially affecting diastolic blood pressure.

The compounds of this invention display submicromolar affinity for the human alpha 1a adrenergic receptor subtype while displaying lower affinity for the human alpha 1d and alpha 1b adrenergic receptor subtypes, and many other G-protein coupled human receptors. One class of the compounds of this invention exhibit nanomolar and subnanomolar affinity for the human alpha 1a adrenergic receptor subtype while displaying at least about 10 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors). In a subclass of the preceding class, the compounds of this invention exhibit nanomolar and subnanomolar affinity for the human alpha 1a adrenergic receptor subtype while displaying at least about 100 fold lower affinity for the human alpha 1d and alpha 1b adrenergic receptor subtypes, in addition to exhibiting selectivity over other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed; e.g., treatment of BPH. For use in medicine, the salts of the compounds of this invention refer to non-toxic "pharmaceutically acceptable salts." Other salts may, however, be useful in the preparation of the compounds according to the invention or in the prepartion of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, benzenesulfonate, benzoate, bicarbonate, bisulfate, bitartrate, borate, camsylate, carbonate, clavulanate, citrate, dihydrochloride, edetate, edisylate, estolate, esylate, fumarate, gluceptate, gluconate, glutamate, glycollylarsanilate, hexylresorcinate hydrobromide, hydrochloride, hydroxynaphthoate, hydroiodide, isothionate, lactate, lactobionate, laurate, malate, maleate, mandelate, mesylate, methylbromide, methylnitrate, methylsulfate, mucate, napsylate, nitrate, n-methylglucamine ammonium salt, oleate, palmitate, pantothenate, phosphate/diphosphate, polygalacturonate, salicylate, stearate, sulfate, subacetate, succinate, tannate, tartrate, tosylate and valerate.

Compounds of this invention are used to reduce the acute symptoms of BPH. Thus, compounds of this invention may be used alone or in combination with more long-term anti-BPH therapeutics, such as testosterone 5-a reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intraocular pressure, control of cardiac arrhythmias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "selective alpha 1a adrenergic receptor antagonist," as used herein, refers to an alpha 1a antagonist compound which exhibits selectivity (e.g., at least about ten fold selectivity) for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention includes pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" encompasses a product comprising the specified ingredients in the specified amounts, as well as any product which results, directly or indirectly, from combination of the specified ingredients in the specified amounts.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

The specificity of binding of compounds showing affinity for the alpha 1a receptor is shown by comparing affinity to membranes obtained from transfected cell lines that express the alpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO 94/08040, published Apr. 14, 1994 and WO 94121660, published Sep. 29, 1994. The cloned human alpha 1a receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g., PCT International Application Publication No. WO 94/10989, published May 26, 1994; U.S. Pat. No. 5,403,847, issued Apr. 4, 1995]. Compounds which are both selective amongst the various human alpha1 adrenergic receptor subtypes and which have low affinity for other receptors, such as the alpha 2 adrenergic receptors, the β-adrenergic receptors, the muscarinic receptors, the serotonin receptors, the histamine receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in which the novel compositions of the present invention may be incorporated for administration orally or by injection include aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin. Other dispersing agents which may be employed include glycerin and the like.

For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range; e.g., from about 0.01 to about 1000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to about 10 mg/kg of body weight per day, and especially from about 0.001 mg/kg to about 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this invention is administration of compounds of this invention and a human testosterone 5-a reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5-a reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5a-reductase inhibitors have been described in WO 93/23420, EP 0572166; WO 93/23050; WO 93/23038; WO 93/23048; WO 93/23041; WO 93/23040; WO 93/23039; WO 93/23376; WO 93/23419; EP 0572165; and WO 93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one embodiment of the present invention, a method of treating BPH is provided which comprises administering to a subject in need of treatment any of the compounds of the present invention in combination with finasteride effective to treat BPH. The dosage of finasteride administered to the subject is from about 0.01 mg per subject per day to about 50 mg per subject per day in combination with an alpha 1a antagonist. In one aspect, the dosage of finasteride in the combination is from about 0.2 mg per subject per day to about 10 mg per subject per day, and, in another aspect, from about 1 to about 7 mg per subject to day (e.g., about 5 mg per subject per day).

For the treatment of benign prostatic hyperplasia, compounds of this invention exhibiting alpha 1a adrenergic receptor blockade can be combined with a therapeutically effective amount of a 5a-reductase 2 inhibitor, such as finasteride, in addition to a 5a-reductase 1 inhibitor, such as 4,7β-dimethyl-4-aza-5a-cholestan-3-one, in a single oral, systemic, or parenteral pharmaceutical dosage formulation. Alternatively, a combined therapy can be employed wherein the alpha 1a adrenergic receptor antagonist and the 5a-reductase 1 or 2 inhibitor are administered in separate oral, systemic, or parenteral dosage formulations. See, e.g., U.S. Pat. Nos. 4,377,584 and 4,760,071 which describe dosages and formulations for 5a-reductase inhibitors.

Abbreviations used in the instant specification, particularly the Schemes and Examples, are as follows:

AcOH=acetic acid
Boc or BOC=t-butyloxycarbonyl
DBU=1,8-diazabicyclo[5.4.0]undec-7-ene
DHP=dihydropyrimidinone
DIBAH=diisobutyl aluminum hydride
DIEA=diisopropylethylamine
DMF=N,N-dimethylformamide
DMSO=dimethylsulfoxide
EDC=1-(3-dimethylaminopropyl)-3-ethylcarbodiimide hydrochloride
EDTA=ethylenediamine tetraacetic acid
Et=ethyl
Et₃N=triethylamine
Et₂O=diethyl ether
EtOAc=ethyl acetate
EtOCOCl=ethylcbloroformate
FAB MS=fast atom bombardment mass spectroscopy
HOBt=1-hydroxy benzotriazole hydrate
HPLC=high performance liquid chromatography
LDA=lithium diisopropyl amide
LHMDA=lithium hexamethyldisilyl amide (or lithium hexamethyldisilazide)
mCPBA=m-chloroperbenzoic acid
m.p.=melting point
Me=methyl
MeOH=methanol
NCS=N-chlorosuccinimide
NMR=nuclear magnetic resonance
OXA or Oxa=oxazolidinone
Ph=phenyl
(p-NO₂Ph)OCOCl=p-nitrophenylchloroformate
Pr=propyl
TFA=trifluoroacetic acid
THF=tetrahydrofuran
TLC=thin layer chromatography
TMS=trimethylsilyl The compounds of the present invention can be readily prepared according to the following reaction schemes and examples, or modifications thereof, using readily available starting materials, reagents and conventional synthetic procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Compounds of the present invention can be prepared by the coupling of a suitable spirotricyclic-substituted azacycloalkane (e.g., azetidine, pyrrolidine, piperidine, hexahydro-1H-azepine, etc.) or spriotricyclic-substituted N-(aminoalkyl)azacycloalkane (e.g., ω-(aminoalkyl) piperidine) with a suitable derivative or activated form of Q—H, as described more fully below.

Spirofluorene-based compounds of the present invention can be prepared in accordance with Scheme 1, wherein fluorene G1 is treated with a strong base (e.g., LHMDA, LDA, or sodium or potassium hydride) and then with N-Boc-bis-(2-chloroethyl)amine to form the Boc-protected spirofluorene piperidine G2, which is treated with acid (e.g., TFA in CH₂Cl₂ or HCl in cold EtOAc) to obtain spirofluorene piperidine G3. Other N-Boc-bis-(haloalkyl)amines can be used in place of N-Boc-bis(2-chloroethyl)amine to provide a wide range of other spirofluorene azacycloalkanes suitable for preparing compounds of the invention; i.e., Boc-protected amines of formula:

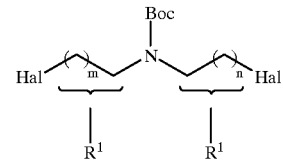

can be used to obtain spirofluorenes of formula:

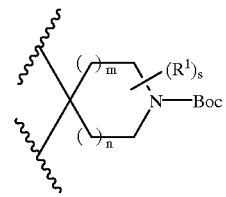

Compounds of formula Q'—H (Q'=Q other than the reverse dihydropyrimidinone (iii)) can be alkylated with a suitable dihaloalkyl compound to give haloalkylated Q' (e.g., N-haloalkyloxazolidinone), which can be coupled to G3 via N-alkylation to obtain G5. Alternatively, G3 can be alkylated with a Boc-protected haloalkylamine to afford G6, which can then be acylated with an activated version of Q'—H to obtain G7. The activated version of Q'—H (e.g., the p-nitrophenylchloroformate derivative of Q'—H) can be obtained by deprotonating Q'—H with a base such as LDA, LHMDA, NaH, KH, or butyllithium, and then reacting the deprotonated species with phosgene or a phosgene equivalent such as (p-NO$_2$Ph)OCOCl. As still another alternative, carboxylated derivative Q"—COOH (Q"=Q of structure (iii); i.e., reverse DHP) can be coupled with G6 via amidation to obtain G7'.

Scheme 2 provides a procedure for preparing spirothioxanthene, 1-oxospirothioxanthene, and 1,1-dioxospirothioxanthene compounds of the invention, wherein thioxanthone G8 is reduced to thioxanthene G9 which is spiroalkylated with NaH and N-methyl bis-(chloroethyl)amine in DMSO to form G10 which is demethylated by procedures known in the art (e.g., treatment with chloroformate) to form G11. N-Methyl bis-(chloroethyl)amine can be replaced with amines of formula:

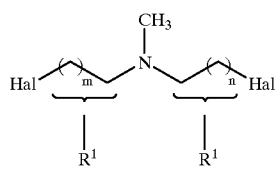

to obtain a wide range of spirothioxanthenes suitable for preparing compounds of the invention. G11 can be oxidized by treatment with 1 or with 2 equivalents of m-chloroperbenzoic acid to give the oxo or dioxo derivatives G12 or G13 respectively. The dioxo derivative G13 can alternatively be prepared directly from G11 by oxidizing G11 with H$_2$O$_2$-acetic acid. Saponification of G11, G12, or G13 with base provides the free amine G14, which can be coupled with a suitable derivative of Q—H to form compounds of the invention G15, G17, and G17' using procedures analogous to those set forth in the description of Scheme 1 above.

Examples of spirothioxanthenepiperidines and their S-oxides and S,S-dixoides suitable for use in preparing compounds of the invention are described in U.S. Pat. No. 4,001,418.

Spiroxanthene, spiroazafluorene, and spirodibenzocycloheptane compounds of the invention can be prepared via in accordance with the procedures set forth in Schemes 3–5 respectively. Reduction of a xanthone derivative, e.g., 77, as illustrated in Scheme 3, provides the xanthene, e.g., 78, which may be spiroalkylated and elaborated to final products as described in preceding schemes and illustrated in Scheme 3. The xanthone 77 may be obtained as described by Granoth and Pownall, *J. Org. Chem.* 1975, 40: 2088–2091. N-methyl-spiroxanthenepiperidine itself (55), obtained as described by Galt et al., *J. Med. Chem.* 1989, 32: 2357–2362, may be converted to the 4-chloro- or 4,7-dichloro derivative by successive treatment with a chlorinating reagent, such as, for example, N-chlorosuccinimide. The product may be elaborated to final products using the procedures already described.

Spiropiperidine derivatives of azafluorenes may be prepared from the corresponding fluorenones as illustrated in Scheme 4. Thus, reduction of the azafluorenones, e.g., 92, by, for example, the Wolff-Kishner procedure known in the art, provides the azafluorenes, e.g., 84 or 93, which may be elaborated to final products using the procedures described above. Azafluorenes and azafluorenones are prepared by procedures known in the art such as, for example, those described by Kloc et al., *J. Prakt. Chem.* 1977, 319: 959–967; DuPriest et al., J. Org. Chem. 1986, 51: 2021–2023; Mayor and Wentrup, *J. Am. Chem. Soc.* 1975, 97: 7467–7480; Fuson and Miller, *J. Am. Chem. Soc.* 1957, 79: 3477–3480; Urbina, *Syn. Comm.* 9: 245–250; Wentrup et al., *J. Org. Chem.* 1978, 43: 2037–2041; Jutz et al., *Liebigs Ann. Chem.* 1975, 874–900; Braven et al., *J. Het. Chem.* 1995, 32: 1051–1055; and Hobson et al., *J. Chem. Soc.,* 1924, 2365–2370; and references cited therein.

Spirodibenzocycloheptanepiperidine derivatives may be prepared as shown in Scheme 5. Thus, 5-cyano-5H-dibenzocycloheptanes such as 100 may be alkylated with, for example, N,N-dimethyl-2-chloroethane and strong base, such as lithium hexamethyldisilazide. The products may be reduced to aldehydes such as 102 with, for example, DIBAH. Examples of the alkylation of 5-cyano-5H-dibenzocycloheptanes and reduction to aldehydes are described by Ting et al., *Bioorg. Med. Chem. Lett.* 1995, 5: 2749–2754. The aldehydes may be condensed with 2-TMS-1,3-dithiane in the presence of base. With refluxing HCl/methanol, the thiane products are converted to thioate esters such as 104 which, upon reduction with, for example, LAH, afford hydroxyethyl derivatives such as 105. Conversion of the hydroxy group to halo by, for example, treatment with triphenylphosphine/carbon tetrachloride, and subsequent intramolecular alkylation to effect ring closure provides spirocyclic quaternary ammonium salts such as 106. Heating results in demethylation to tertiary amines such as 107, which may be again demethylated to the spiropiperidine and elaborated to final products using the procedures described above.

Q—H and derivatives suitable for use in the foregoing schemes can be prepared by procedures known to those of ordinary skill in the art. For example, unsubstituted, alkyl- and cycloalkyl-substituted oxazolidinones are prepared and activated in general by published and well developed chemistry, in particular, of Evans. See, e.g., Evans et al., "Stereoselective Aldol Condensations" in *Topics in Stereochemistry* (1982), 13: 1–115. The starting materials, in general, are natural and unnatural amino acids. For instance, some of the compounds are prepared from substituted phenyl glycine derivatives, which after reduction of the carboxylate and a phosgene equivalent mediated cyclization provides the substituted oxazolidinone ring system. Deprotonation with a strong base such as n-butyl lithium and addition to a phosgene or phosgene equivalent such as a THF solution of p-nitrophenylchloroformate produces the stable, isolable "activated" Oxa.

Oxazolidinones substituted with carboxylate, carboxamide, and alkoxyalkyl can be prepared by hydroxyamination of olefins to provide protected aminoalcohols, using procedures as described in G. Li et al., *Angew. Chem. Int. Ed. Engl.* (1996), 35: 2813–2817. Deprotection under standard conditions followed by a phosgene equivalent to mediate cyclization provides the substituted oxazolidinone ring system. Deprotonation with a strong base, for example, lithium bis(trimethylsilyl)amide, and addition to a THF solution of p-nitrophenylchloroformate (or other phosgene equivalent) produces the stable, isolable "activated" oxazolidinone.

Dihydropyrimidinones can be prepared by condensation reaction of the aldehyde, urea and a 1,3-acetoacetate type derivative catalyzed by a Lewis Acid, a copper (I) species and acetic acid. Activation can be accomplished by treatment with a strong base, for instance, LiN(TMS)$_2$, followed by addition to a THF solution of p-nitrophenylchloroformate.

Hydantoins can be prepared in two chemical steps from ketones as outlined in the literature. More specifically, hydantoins can be prepared according to known methodology, such as described in J. J. Edmunds et al., *J. Med. Chem.* 1995, 38: 3759–3771, in J. H. Poupaert et al., *J. Chem. Res. (S)* 1979, 174–175, and in *Chem. Rev.* 1950, 46: 403–457.

Saccharins can be prepared according to known methods; e.g., page 40 and Examples 21 and 22 of PCT International Application Publication No. WO 96/25934, published Aug. 29, 1996.

The dihydropyrimidinones, oxazolidinones and hydantoins can be synthesized independently in racemic form, separated utilizing preparative chiral HPLC or other conventional procedures for separating optical isomers (e.g., resolution of diastereomeric salts), and then activated and reacted with the suitable spirotricyclic azacycles.

A general procedure for preparing reverse DHP intermediates is set forth in Scheme 6, wherein the methylproprionate C1 is condensed with urea C2 and arylaldehyde C3, catalyzed by acetic acid, copper oxide and a Lewis acid (e.g., $BF_3.Et_2O$) to obtain the 4-aryl-1,2,3,4-tetrahydropyrimidin-2-one-5-carboxylic acid methyl ester C4, which is subsequently converted to the 5-carboxylic acid derivative C6 by basic hydrolysis. Alternatively, the methyl ester can first be treated with an alkyl or cycloalkyl halide (e.g., an iodide such as methyl iodide) to obtain the 3-alkyl or 3-cycloalkyl derivative C5, which is then hydrolyzed to the 5-carboxylic acid derivative C7.

Reverse DHP optical isomers can be resolved by using preparative chiral HPLC. They can also be resolved by reacting a mixture of methyl ester enantiomers with LDA and p-nitrophenylchloroformate, followed by treatment with R-(+) alpha methyl benzylamine to obtain the 3-(1-phenylethyl-carbamoyl) diastereomers, which are separated by conventional means known in the art. The enantiomers are then obtained from the separated diastereomers first by reaction with DBU to regenerate the methyl ester (e.g., enantiomer of C4), followed directly by basic hydrolysis to obtain the corresponding carboxylic acid enantiomer (e.g., enantiomer of C6), or followed by reaction with an alkyl or cycloalkyl halide (to provide, e.g., an enantiomer of C5) and then hydrolysis to obtain the corresponding carboxylic acid enantiomer (e.g., enantiomer of C7).

Scheme 1

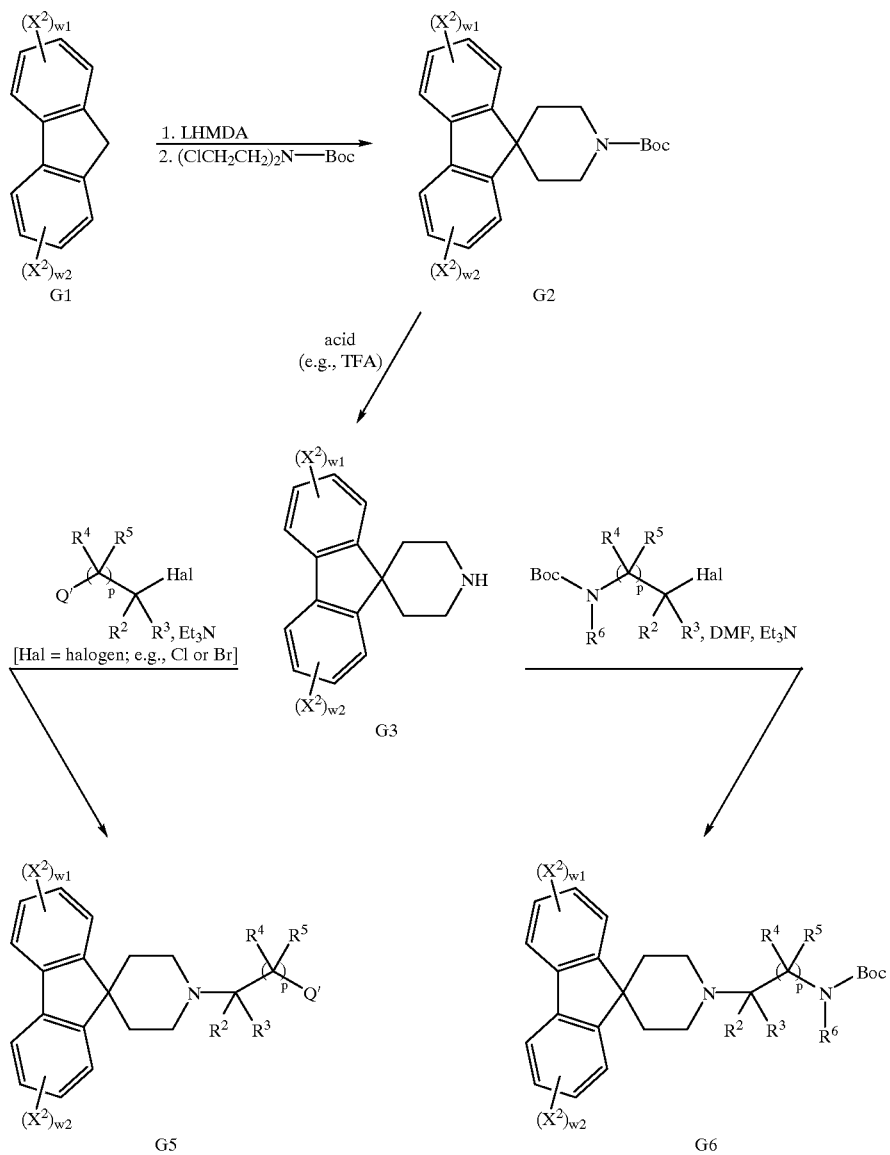

-continued
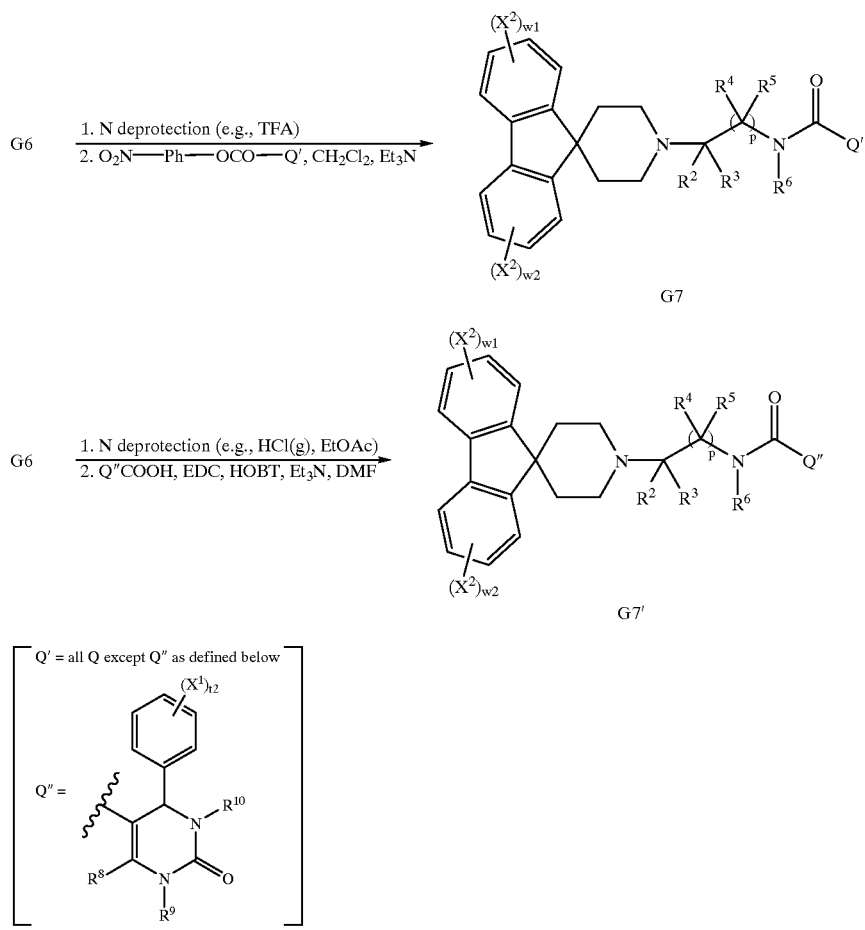
Scheme 2
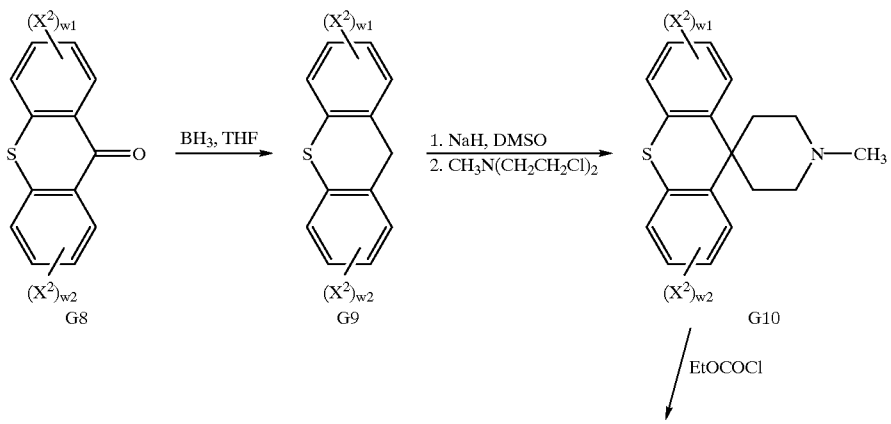

-continued
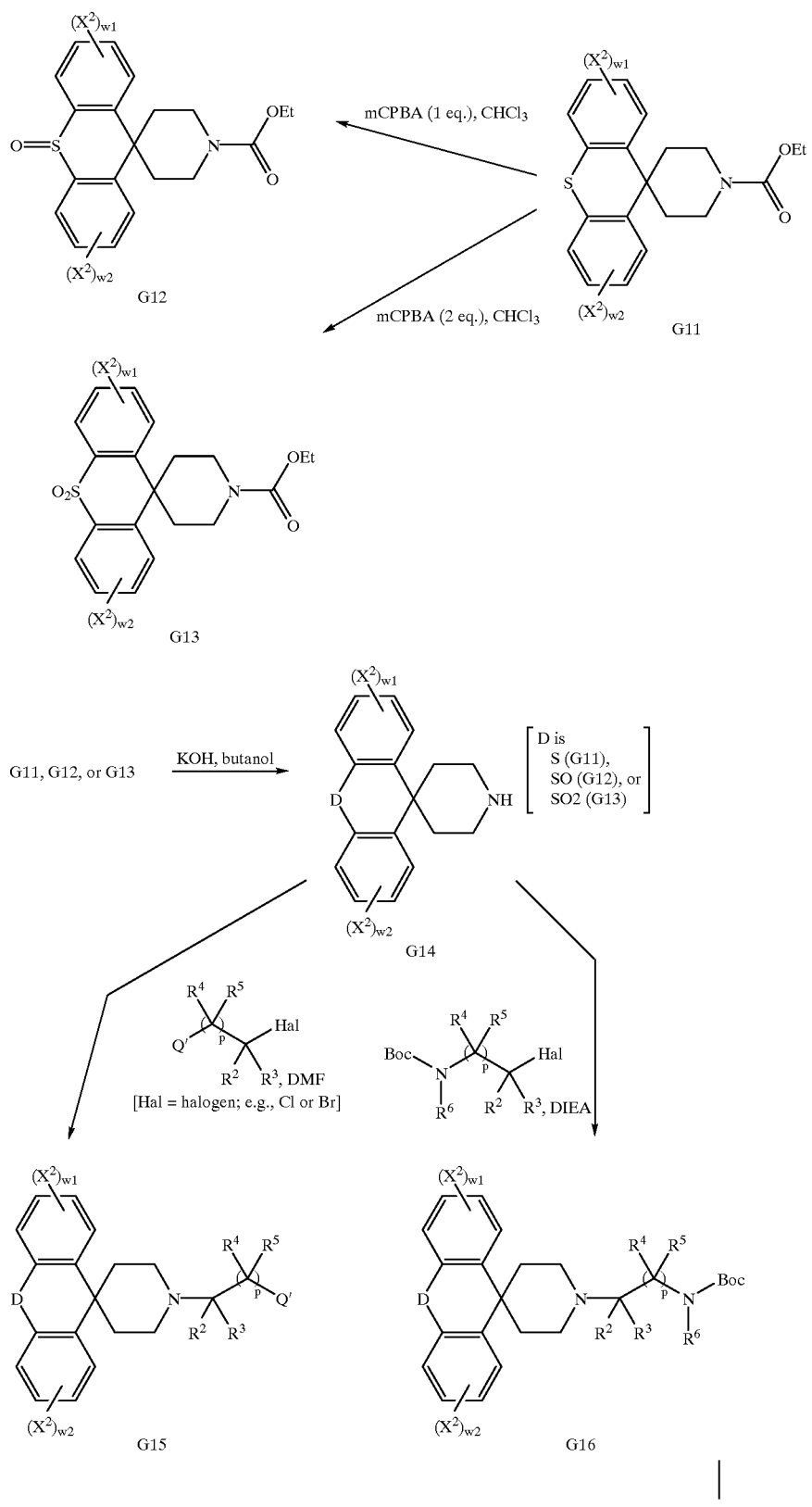

-continued
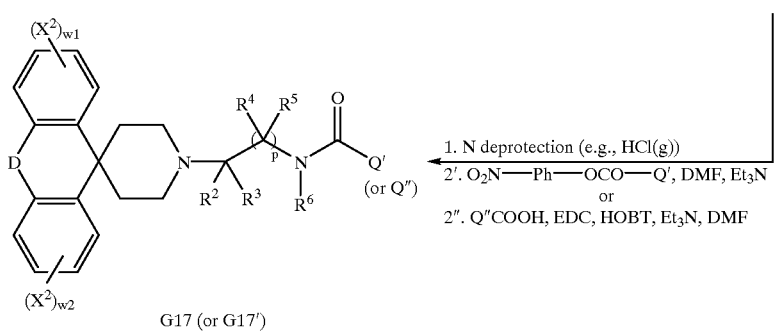
G17 (or G17')
[Q' and Q" are as defined in Scheme 1]
Scheme 3
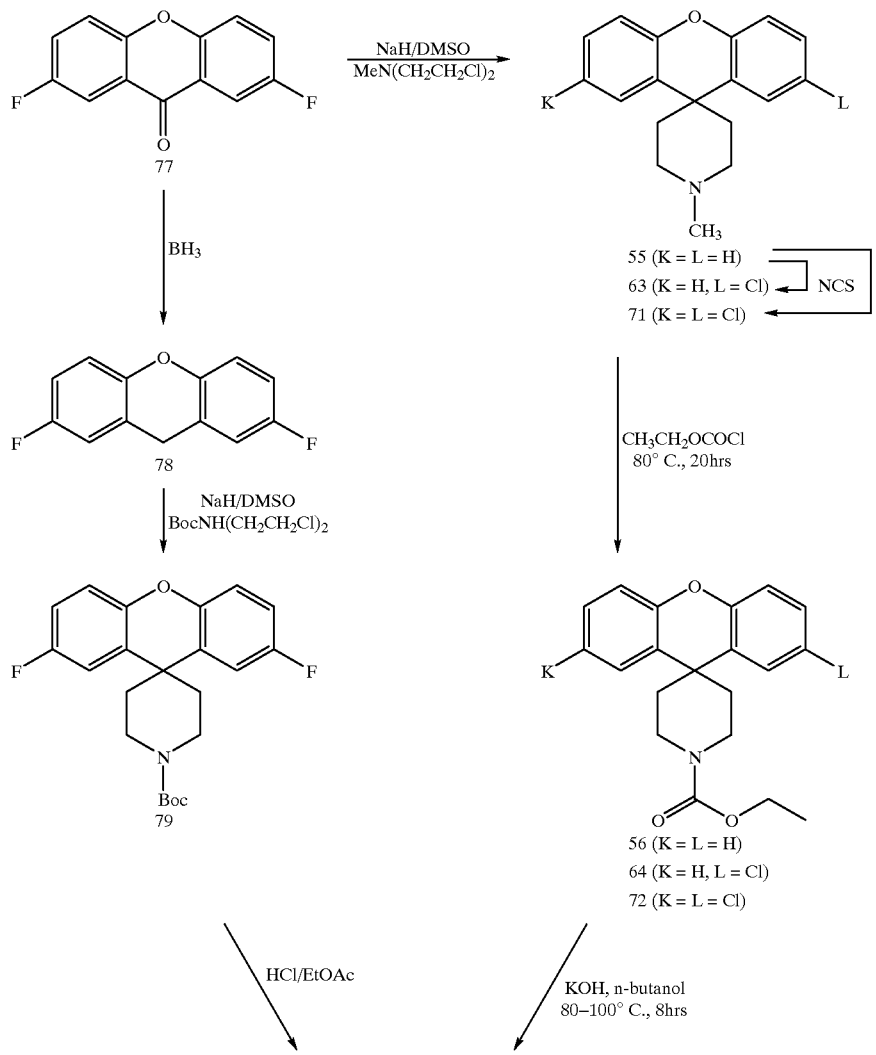

-continued
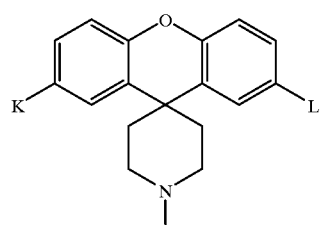
57 (K = L = H)
65 (K = H, L = Cl)
73 (K = L = Cl)
80 (K = L = F)
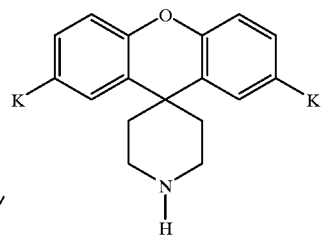
57 (K = L = H)
65 (K = H, L = Cl)
73 (K = L = Cl)
80 (K = L = F)
Et₃N
Br(CH₂)₃NHBOC
BrCH₂CH₂CH₂—Q″, DMF, Et₃N
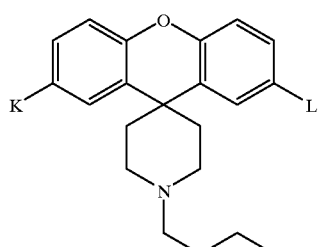
58 (K = L = H)
66 (K = H, L = Cl)
74 (K = L = Cl)
81 (K = L = F)
TFA/CH₂Cl₂
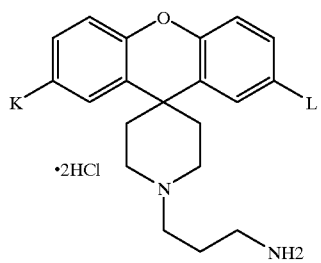
59 (K = L = H)
67 (K = H, L = Cl)
75 (K = L = Cl)
82 (K = L = F)
O₂N—Ph—OCO—Q′
CH₂Cl₂
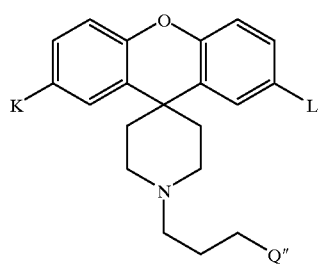
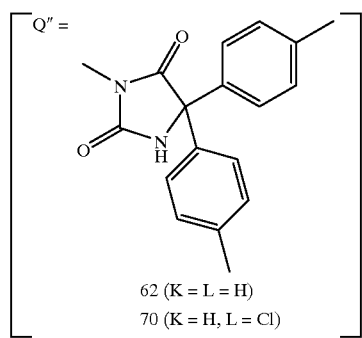
62 (K = L = H)
70 (K = H, L = Cl)

-continued
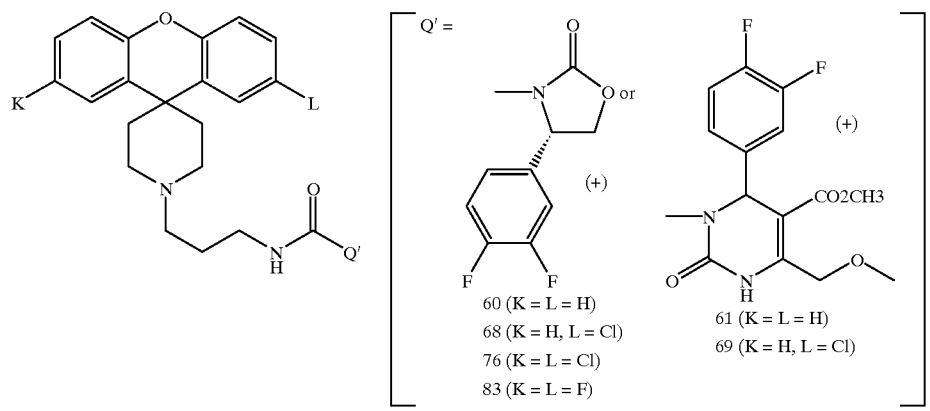
Scheme 4
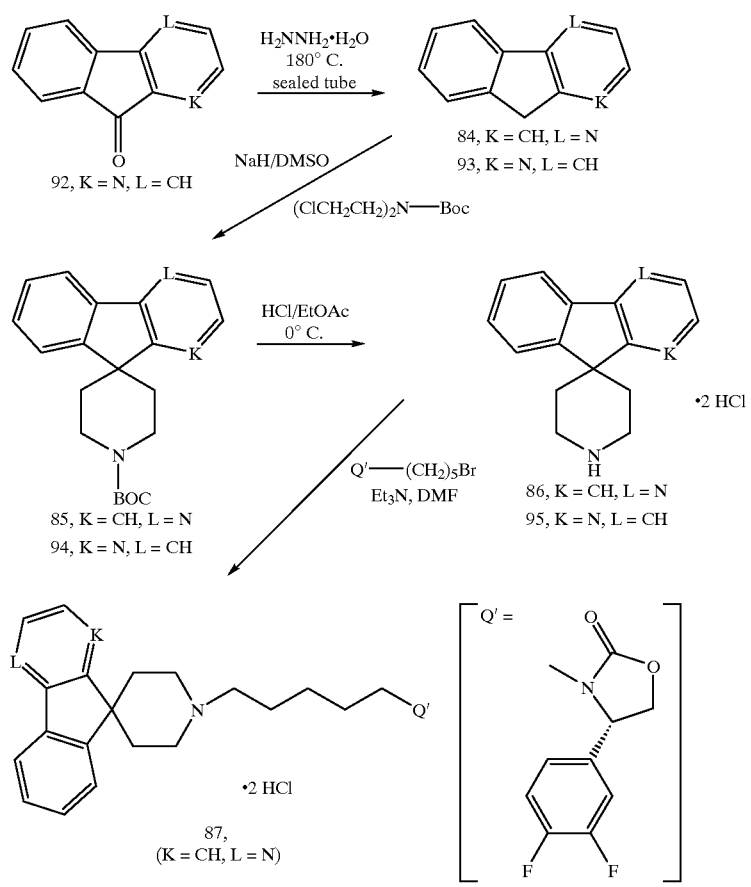

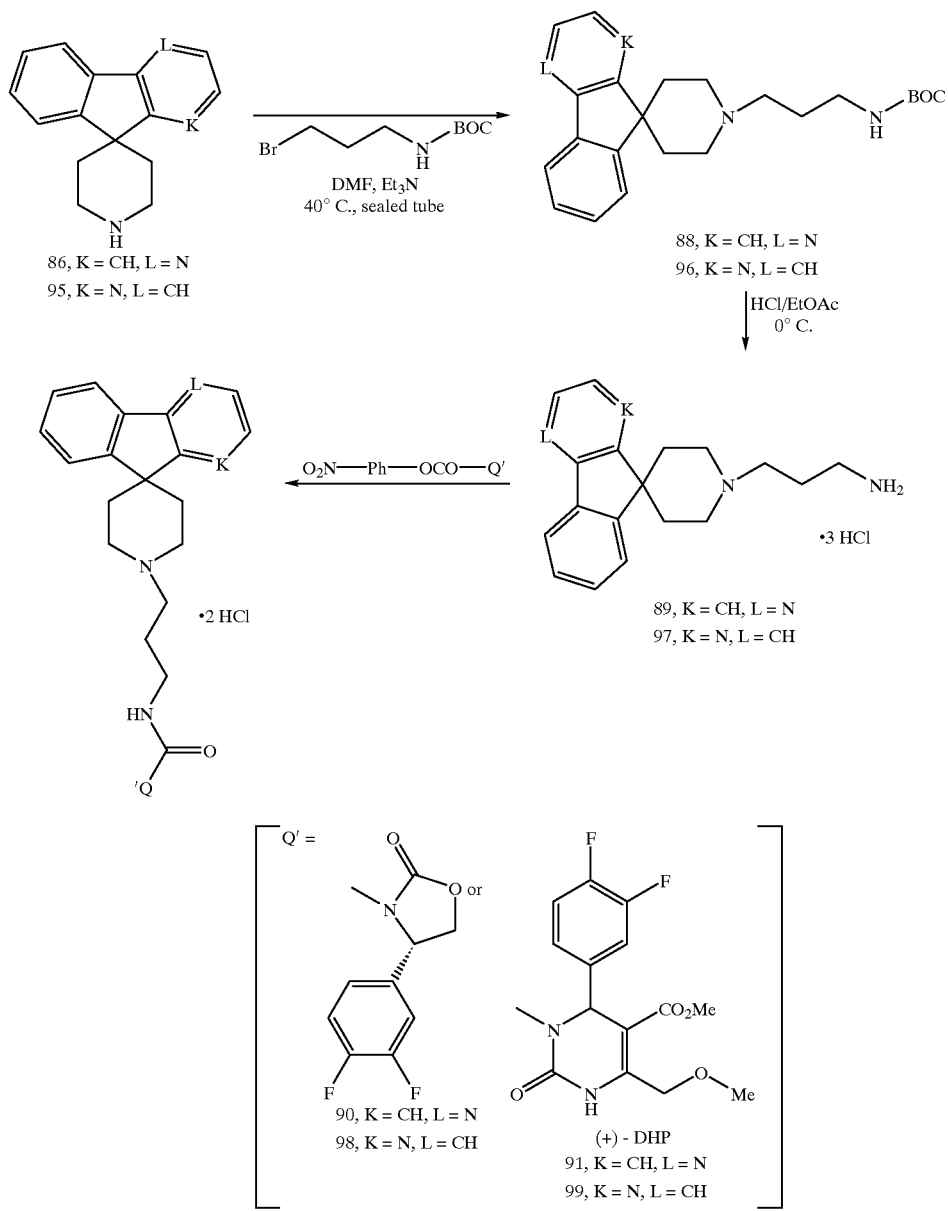
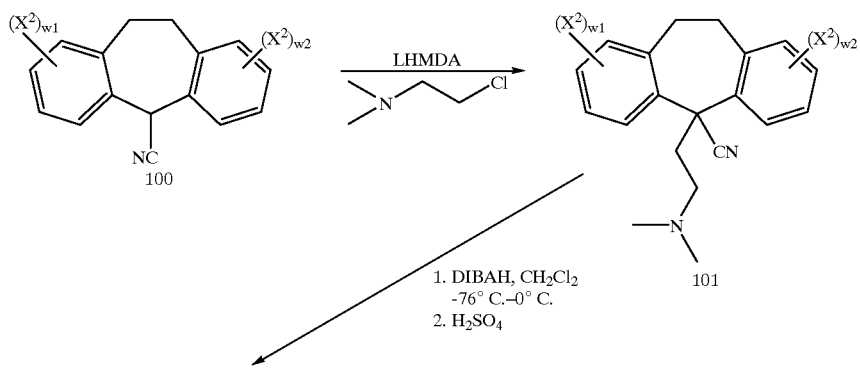
Scheme 5

-continued
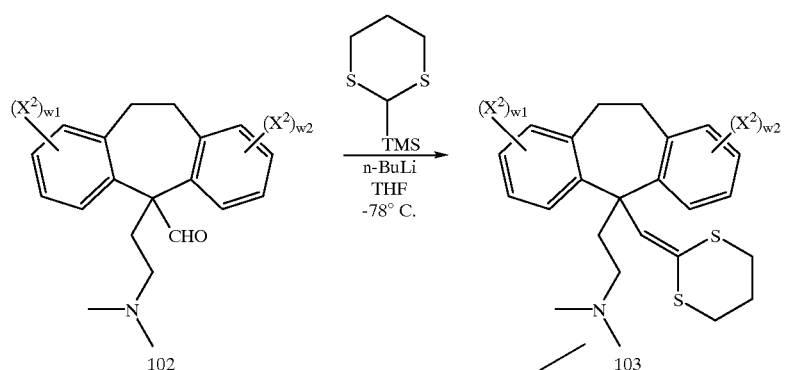
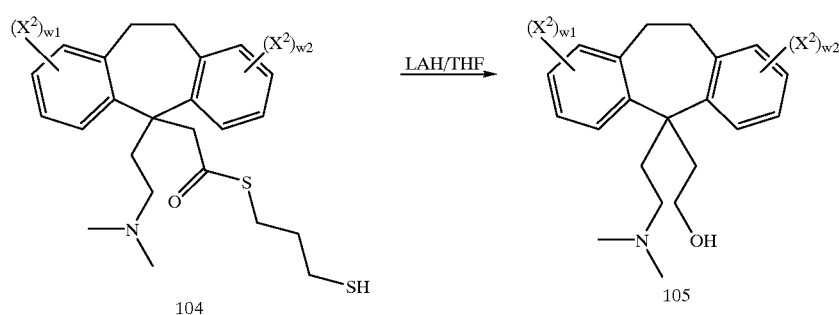
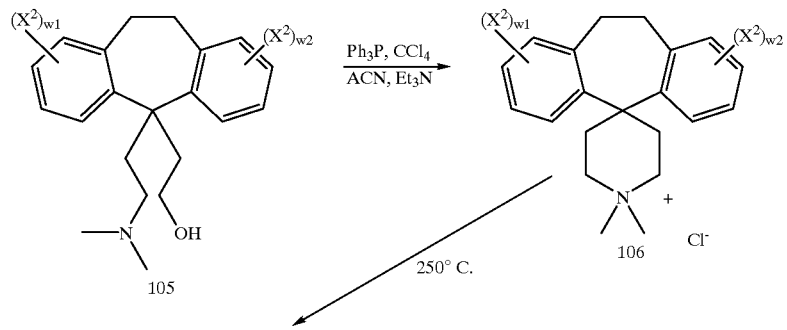
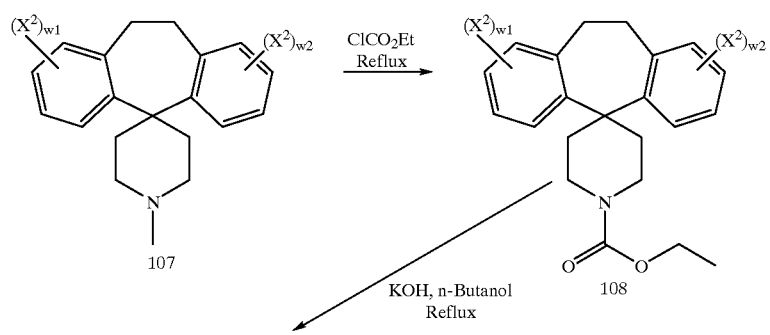

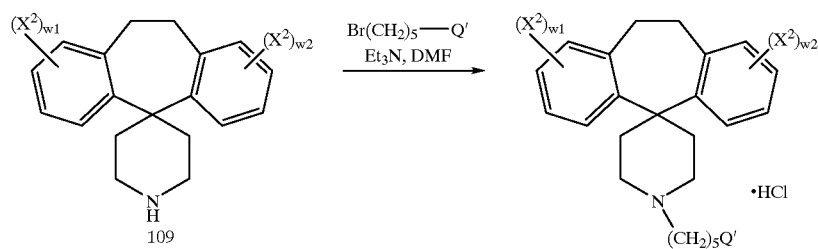
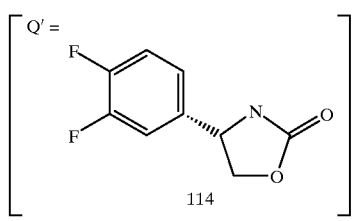
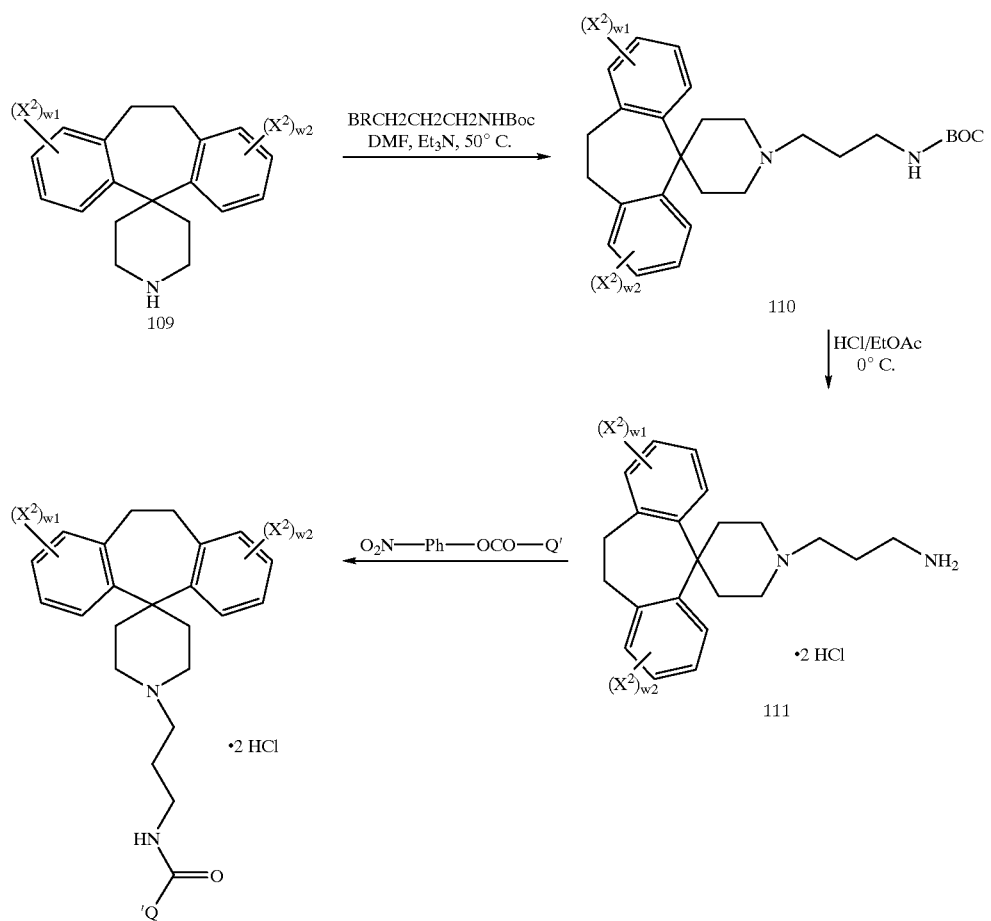

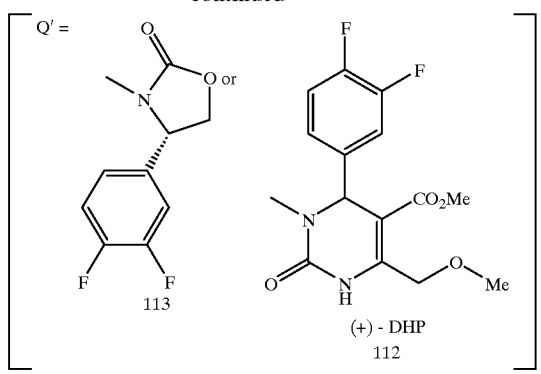

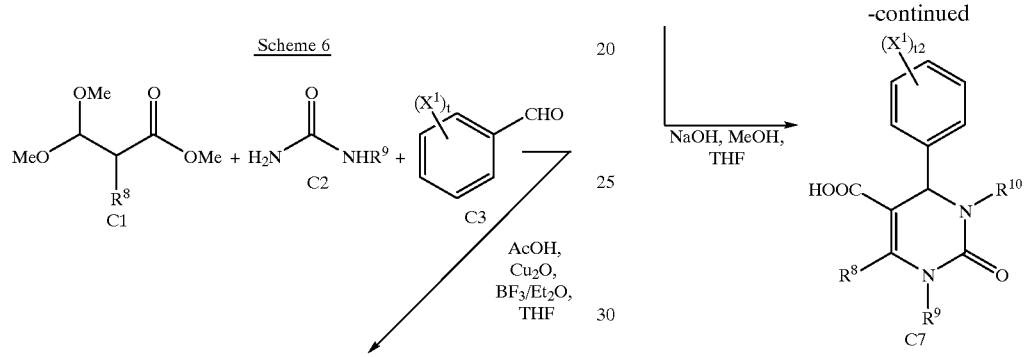

The following Examples further describe and illustrate the invention and its practice and are not to be construed as limiting the scope or spirit of the invention.

EXAMPLE 1

Spirofluorene-9,4'-piperidine (3)

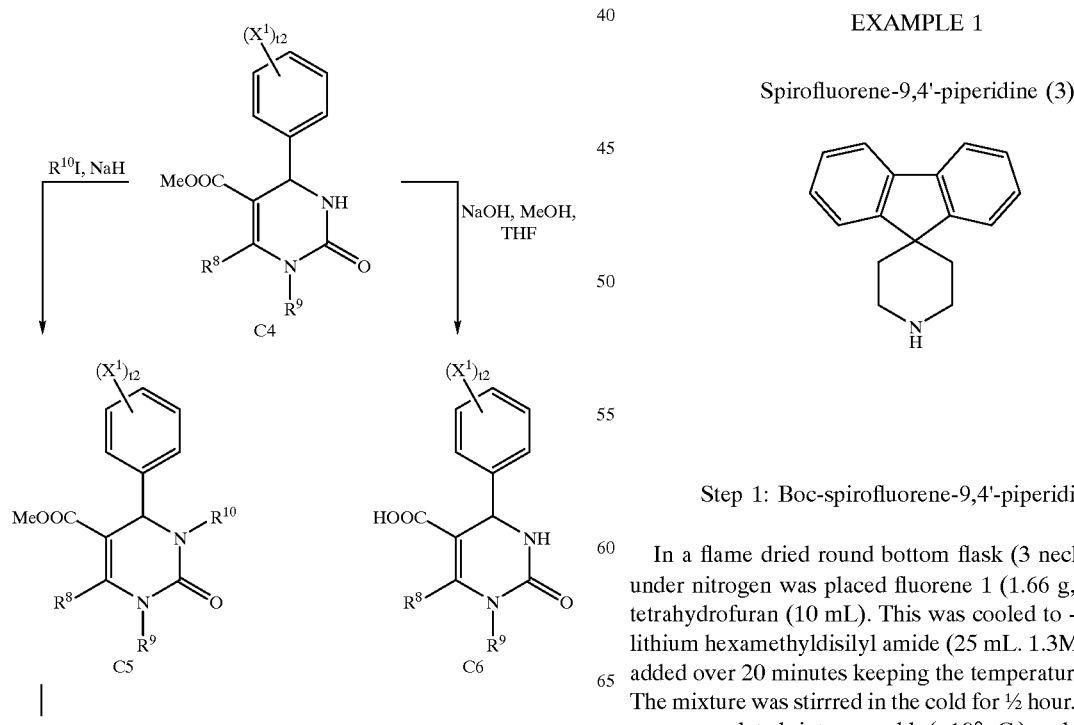

Step 1: Boc-spirofluorene-9,4'-piperidine (2)

In a flame dried round bottom flask (3 necked, 250 mL) under nitrogen was placed fluorene 1 (1.66 g, 10 mmol) in tetrahydrofuran (10 mL). This was cooled to −5° C. by and lithium hexamethyldisilyl amide (25 mL. 1.3M in THF) was added over 20 minutes keeping the temperature below 0° C. The mixture was stirrred in the cold for ½ hour. This solution was cannulated into a cold (−10° C.) solution of N-t- butoxycarbonyl-bis-(2-chloroethyl)amine (3.65 gms, 0.015 m) in tetrahydrofuran (10 mL) stirred in a flame dried round bottom flask (3 necked, 250 mL) under nitrogen. The resulting solution was stirred at 0° C. for 2 hours. The ice bath was removed and the mixture stirred ½ hour at room temperature. Ether (100 mL) was added and the mixture washed with sat. aq. NaHCO$_3$, H$_2$O, 10%KHSO$_4$, and brine. The solution was dried over Na$_2$SO$_4$, filtered, and concentrated under reduce pressure. Hexane was added and the mixture filtered to yield the title compound as a solid.

NMR: consistent with structure

PLC: 100% at 215 nm and 254 nm

Step 2: Spirofluorene-9,4'-piperidine (3)

To a solution of Boc-spirofluorene-9,4'-piperidine 2 (1.5 g, 4.5 mmol) in methylene chloride (25 mL) was added trifluoroacetic acid (2 mL). The mixture was stirred at room temperature for 48 hours. The solvent was removed under reduce pressure. Ethyl acetate was added and the organic layer was washed with a combined solution of sat. aq. NaHCO$_3$, and sat. aq. Na$_2$CO$_3$, followed by brine. The organic layer was dried over Na$_2$SO$_4$, filtered, and concentrate to yield the title compound.

NMR: consistent with structure

FAB MS: M+H @ m/e=236.11

Anal. cal'd for C17H17N.0.25 H$_2$O.0.1 TFA: C, 82.22; H, 7.06; N, 5.58. Found: C, 82.14; H, 6.95; N, 5.64.

EXAMPLE 2

(+)-1'-{5-[((4(S)-(3,4-difluorophenyl)-2-oxo-oxazolidin)-3-yl)]-pentyl}-spirofluorene-9,4'-piperidine (4)

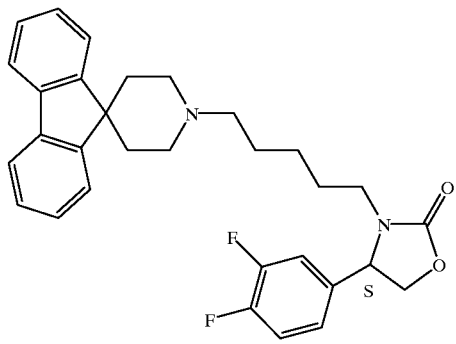

To a stirred solution of spirofluorene-9,4'-piperidine 3 (33.7 mg, 0.14 mmol) in DMF (1 mL) was added a solution of 3-(5-bromopentyl)-4-(S)-(3,4-difluorophenyl)-oxazolidin-2-one (50 mg, 0.14 mmol) in DMF (1 mL). Triethylamine(200 μL) was added and the reaction stirred overnight. The solvent was removed under reduced pressure to give a gum which was dissolved in ethyl acetate and washed with sat. aquous sodium bicarbonate and brine. The solution was dried over sodium sulfate, filtered, and concentrated to a gum. Purification by chromatography on silica gel eluted with 4% methanol/methylene chloride gave the title compound as a white foam.

HPLC: 100% @ 215 nm and 254 nm

FAB MS: M+H @ m/e=503.11

Anal. cal'd for C31H32F2N2O2: C, 74.08; H, 6.42; N, 5.57. Found: C, 73.89; H, 6.77; N, 5.44.

EXAMPLE 3

1'-{5-[((4-(3,4-difluorophenyl)-2-oxo-oxazolidin)-3-yl)]-pentyl}-spirofluorene-9,4'-piperidine (Racemate of compound (4)

This compound was prepared using the procedure of Example 2 substituting racemic 3-(5-bromopentyl)-4-(3,4-difluorophenyl)-oxazolidin-2-one for the (S) compound.

HPLC: 99.78% @ 215 nm, 100% @ 254 nm

FAB MS: M+H @ m/e=503.26

Anal. cal'd for C31H32F2N2O2.0.3 H2O: C, 73.29; H, 6.47; N, 5.51. Found: C, 73.31; H, 6.44; N, 5.54.

EXAMPLE 4

1'-[3-(5,5-Bis-p-tolyl-2,4-dioxoimidazolidin-3-yl)propyl]spirofluorene-9,4'-piperidine (5)

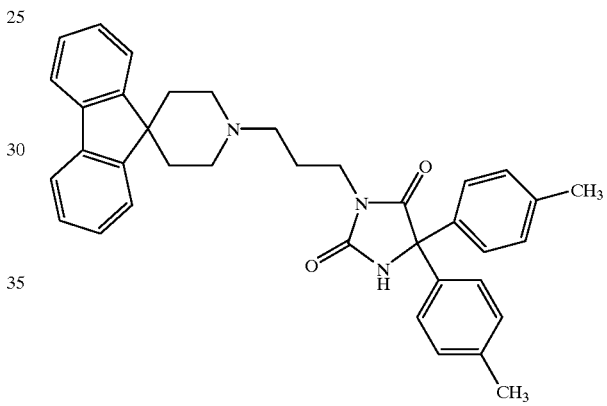

In a round bottom flask (25 mL) under an atmosphere of nitrogen was placed spirofluorene-9,4'-piperidine 3 (46 mg, 0.195 mol) and 3-(3-bromopropyl)-5,5-di-p-tolylhydantoin (80 mg, 0.19 mmol). DMF (1 mL) was added, followed by triethylamine (150 mL). The reaction was stirred overnight at room temperature, then heated at 50° C. for 2 hours. The DMF was removed under reduced pressure to give a gum that was dissolved in ethyl acetate. The organic material was washed with a combination of aqueous saturated sodium carbonate and sodium bicarbonate followed by brine. After drying over sodium sulfate, the ethyl acetate layer was filtered and concentrated to an oil which was chromatgtaphed on silica gel with 4% methanol-methylene chloride elution. Removal of the solvent gave the title compound as a white foam.

HPLC: 98.88% at 215 nm and 99.09% at 254 nm.

NMR: consistent with the structure.

FAB MS: M+H @ m/e=556.21

Anal. cal'd for C37H37N3O2.0.15 Et$_2$O: C, 79.67; H, 6.85; N, 7.41. Found: C, 79.69; H, 7.12; N, 7.02.

EXAMPLE 5

1'-{6-[((4S)-(3,4-Difluorophenyl)-2-oxooxazolidin)-3-yl]hexyl}-spirofluorene-9,4'-piperidine (6)

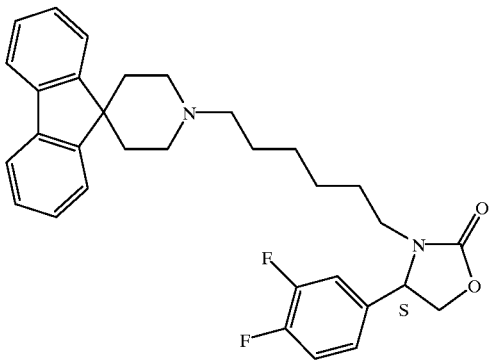

In a round bottom flask (25 mL) under nitrogen was placed spirofluorene-9,4'-piperidine 3 (46 mg, 2 mmol), 3-(6-bromohexyl)-4-(S)-(3,4-difluorophenyl)-oxazolidin-2-one (72 mg, 2 mmol) and DMF (1 mL). Triethylamine (150 mL) was added and the mixture was stirred overnight at room temperature. The DMF was removed under reduced pressure and the resulting gum was dissolved in ethyl acetate and washed with a combination of aqueous saturated sodium carbonate and sodium bicarbonate followed by a brine. The organic layer was dried over sodium sulfate, filtered and concentrated. Purification was achieved by chromatography on silica eluted with 4% methanol-methylene chloride. The product fractions were collected and concentrated to yield the title compound as a white foam.

FAB MS: M+H @ m/e=517.33

HPLC: 100% at 215 nm and 254 nm

Anal. cal'd for C32H34F2N2O2.0.6 H2O: C, 72.86; H, 6.73; N, 5.31. Found: C, 72.82; H, 6.61; N, 5.41.

EXAMPLE 6

1'-{3-[(4S)-(3,4-Difluorophenyl)-2-oxooxazolidin-3-carbonylamino]propyl}spirofluorene-9,4'-piperidine (9)

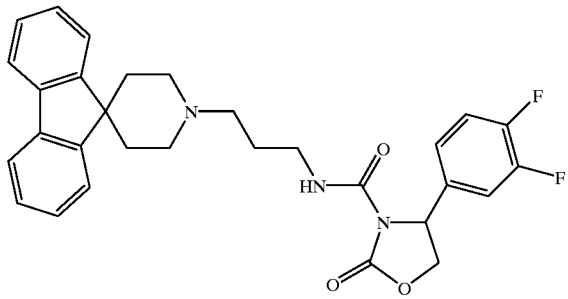

Step 1: 1'-(Boc-3-aminopropyl)spirofluorene-9,4'-piperidine 7

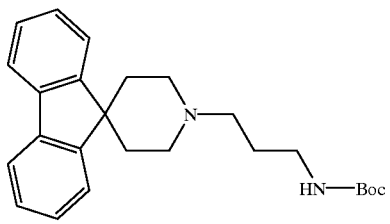

In a round bottom flask (25 mL) under nitrogen was placed spirofluorene-9,4'-piperidine 3 (705 mg, 3 mmol) and t-Boc-3-bromopropylamine (714 mg, 3 mmol). DMF (3 mL) was added followed by triethylamine (700 mL), and the reaction was allowed to stir 18 hours. Triethylamine (100 mL) was added and the reaction was heated at 50 C. for 1.5 hours. The DMF was removed under reduced pressure to give a gum which was dissolved in ethyl acetate. The organic layer was washed with sodium bicarbonate(aq. sat.)/sodium carbonate (aq. sat.) and brine, dried over sodium sulfate, filtered and concentrated to a gum. Purification was accomplished by column chromatography on silica with 4% methanol/methylene chloride elution. The solvent was removed under vacuum to give the title compound.

Step 2: 1'-(3-Aminopropyl)spirofluorene-9,4'-piperidine (8)

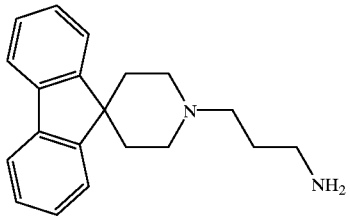

1'-(Boc-3-aminopropyl)spirofluorene-9,4'-piperidine 7 was dissolved in methylene chloride (20 mL) under a nitrogen atmosphere. Trifluoroacetic acid (2.5 mL) was added and the reaction was stirred overnight. The mixture was washed with sodium bicarbonate/sodium carbonate (aq. sat.) solution, followed by brine, dried over sodium sulfate, filtered and concentrated to give the title compound.

Step 3: 1'-{3-[(4S)-(3,4-Difluorophenyl)-2-oxooxazolidin-3-carbonylamino]propyl}spirofluorene-9,4'-piperidine (9)

Under an atmosphere of nitrogen in a round bottom flask (25 mL), 1'-(3-aminopropyl)spirofluorene-9,4'-piperidine, 8 (87 mg, 0.3 mmol) was dissolved in methylene chloride(4 mL). 3-(p-Nitrophenoxycarbonyl)-4-(S)-(3,4-difluorophenyl)-oxazolidin-2-one (109 mg, 0.3 mmol) was added, followed by triethylamine (200 mL), and the reaction was stirred 18 hours. The solvent was removed under reduce pressure. The resulting gum was dissolved in ethyl acetate and washed four times with potassium carbonate (10% aqueous).The ethyl acetate was then washed with brine, dried over sodium sulfate filtered and concentrated. The residue was treated with ether/hexane and evaporated in vacuo to give the title compound as a white foam.

FAB MS: M+H @ m/e=518.28

HPLC: 98.53% at 214 nm and 99.22% at 254 nm $^1$H NMR (CDCl$_3$): consistent with structure Anal. cal'd for C30H29F2N3O3.0.25 Et$_2$O.0.1 H$_2$O: C, 69.21; H, 5.94; N, 7.81. Found: C, 69.20; H, 6.09; N, 7.86.

EXAMPLE 7

1'-{3-[(2S)-(3,4-Difluorophenyl)-4-oxothiazolidin-3-carbonylamino]propyl}spirofluorene-9,4'-piperidine (10)

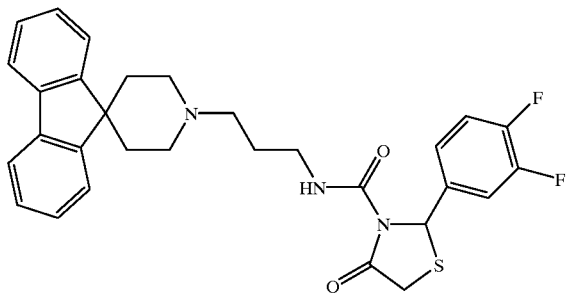

Under an atmosphere of nitrogen in a round bottom flask (25 mL), 1'-(3-aminopropyl)spirofluorene-9,4'-piperidine, 8 (75 mg, 0.256 mmol) was dissolved in methylene chloride(4 mL). 3-(p-Nitrophenoxy-carbonyl)-2-(S)-(3,4-difluorophenyl)-thiazolidin-4-one (96 mg, 0.256 mmol) was added, followed by triethylamine (200 mL), and the reaction was stirred 18 hours. The solvent was removed under reduced pressure, and the resulting gum was dissolved in ethyl acetate washed four times with potassium carbonate (10% aqueous), then with brine, dried over sodium sulfate filtered and concentrated. Silica gel chromatography with 4% methanol/methylene chloride elution provided the title compound.

FAB MS: M+H @ m/e=534.20

HPLC: 98.12% at 215 nm and 97.95% at 254 nm $^1$H NMR: consistent with structure Anal. cal'd for C30H29F2N3O2S.0.2 H$_2$O: C, 67.06; H, 5.52; N, 7.82. Found: C, 67.08; H, 5.60; N, 7.62.

EXAMPLE 8

1,2,3,6-tetrahydro-1-[(spirofluorene-9,4'-piperidin-1'-yl)propyl]aminocarbonyl-5-methoxycarbonyl-4-methoxymethyl-6(S)-(3,4-difluorophenyl)-2-oxopyrimidine (11)

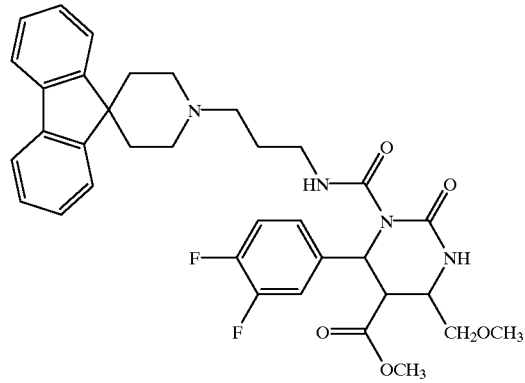

Under a nitrogen atmosphere, 1'-(3-aminopropyl)-spirofluorene-9,4'-piperidine 8 (87 mg, 0.3 mmol) was dissolved in methylene chloride (4 mL). 5-Methoxycarbonyl-4-methoxymethyl-1,2,3,6-tetrahydro-2-oxo-6(S)-(3,4-difluorophenyl)-1-(4-nitrophenyloxy-carbonyl)pyrimidine (139 mg, 0.3 mmol) was added, followed by triethylamine (200 mL). The mixture was stirred for 18 hours, the solvent was removed under reduced pressure, and the resulting gum was dissolved in ethyl acetate. The solution was washed four times with 10% aqueous potassium carbonate(10%), then with brine, dried over sodium sulfate, filtered, and concentrated in vacuo. The residue was twice treated with ether/hexane and evaporated under reduced pressure to give the title compound as a white foam.

FAB MS: M+H @ m/e=631.28

HPLC: 96.54% at 214 nm and 97.47% at 254 nm

Anal. cal'd for C35H36F2N4O5.0.25 Et$_2$O: C, 66.60; H, 5.98; N, 8.63. Found: C, 66.75; H, 6.25; N, 8.64.

EXAMPLE 9

2-Bromospirofluorene-9,4'-piperidine (14)

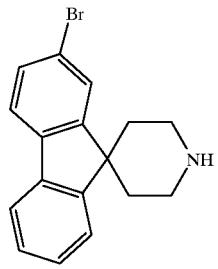

Step 1: Boc-2-bromospirofluorene-9,4'-piperidine 13

This compound was prepared using the procedure of Example 1, step 1, starting with 2-bromofluorene, 12 (2.45 g, 0.01 mol) in place of fluorene, 1. The crude product was purified by silica gel chromatography with 20% ethyl acetate/hexane elution. The product fractions were concentrated to give the title compound as a white solid.

HPLC: 100% at 214 nm and 100% at 254 nm.

NMR: consistent with structure.

FAB MS: M+H @ m/e=415.06.

Step 2: 2-Bromospirofluorene-9,4'-piperidine (14)

This compound was prepared using the procedure of Example 1, step 2 (compound 3), starting with Boc-2-bromospirofluorene-9,4'-piperidine 13 (1.5 g, 3.6 mmol) in place of Boc-spirofluorene-9,4'-piperidine 2.

FAB MS: M+H @ m/e=314.04

HPLC: 98.53% at 214 nm and 98.84% at 254 nm $^1$H NMR (CDCl$_3$): consistent wioth structure Anal. cal'd for C17H16BrN.0.1 CH$_2$Cl$_2$: C, 61.57; H, 5.26; N, 4.20. Found: C, 61.60; H, 4.86; N, 4.15.

EXAMPLE 10

1'-[3-(5,5-Bis-p-tolyl-2,4-dioxoimidazolidin-3-yl) propyl]-2-bromospirofluorene-9,4'-piperidine (15)

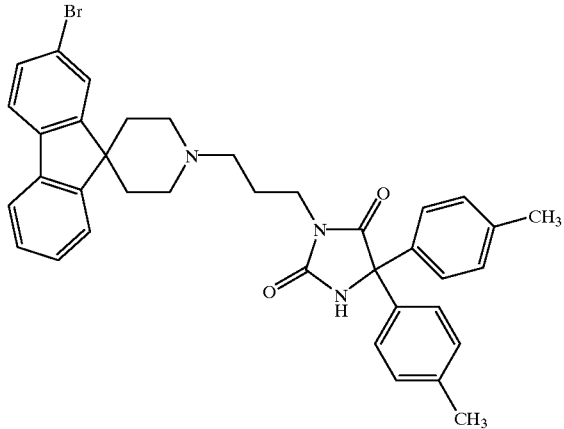

This compound was prepared using the procedure of Example 4, starting with 2-bromospirofluorene-9,4'-piperidine 14(47 mg, 0.15 mmol) in place of spirofluorene-9,4'-piperidine, 3.

FAB MS: M+H @ m/e=636.11

HPLC: 98.42% at 214 nm and 100% at 254 nm

Anal. cal'd for C37H36BrN3O2.0.3 H$_2$O: C, 70.03; H, 5.72; N, 6.62. Found: C, 70.03; H, 6.09; N, 6.64.

EXAMPLE 11

1,2,3,6-tetrahydro-1-[((2-bromospirofluorene-9,4'-piperidin)-1'-yl)propyl]aminocarbonyl-5-methoxycarbonyl-4-methoxymethyl-6(S)-(3,4-difluorophenyl)-2-oxopyrimidine (18)

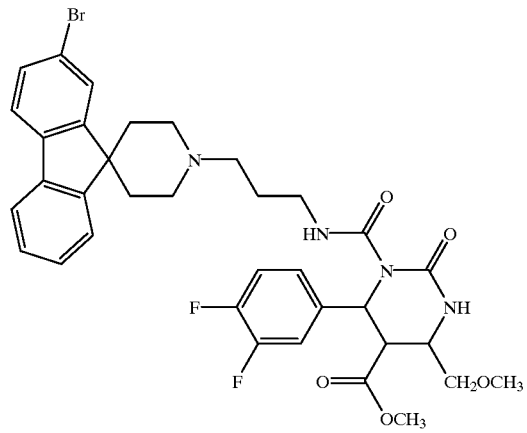

Step 1: 1'-(Boc-3-aminopropyl)-2-bromospirofluorene-9,4'-piperidine (16)

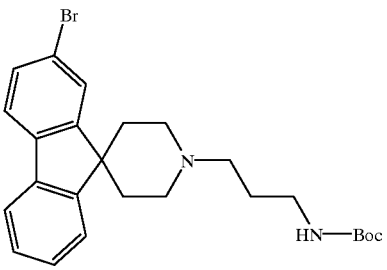

This compound was prepared using the procedure of preparation 1, step 1, starting with 2-bromospirofluorene-9, 4'-piperidine 14 in place of spirofluorene-9,4'-piperidine 3.

Step 2: 1'-(3-Aminopropyl)-2-bromospirofluorene-9, 4'-piperidine (17)

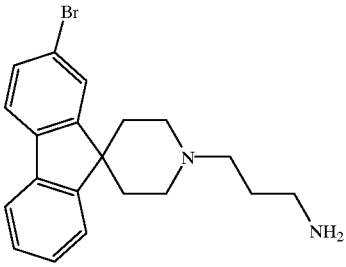

This compound was prepared using the procedure of preparation 1, step 2, starting with 1'-(Boc-3-aminopropyl)-2-bromospirofluorene-9,4'-piperidine 16 in place of 1'-(Boc-3-aminopropyl)spirofluorene-9,4'-piperidine 7.

Step 3: 1,2,3,6-tetrahydro-1-[((2-bromospirofluorene-9,4'-piperidin)-1'-yl)propyl]aminocarbonyl-5-methoxycarbonyl-4-methoxymethyl-6(S)-(3,4-difluorophenyl)-2-oxopyrimidine (18)

This compound was prepared using the procedure of Example 8, starting with 1'-(3-aminopropyl)-2-bromospirofluorene-9,4'-piperidine 17 in place of 1'-(3-aminopropyl)spirofluorene-9,4'-piperidine, 8. The title compound was obtained as a white foam.

FAB MS: M+H @ m/e=711.3

HPLC: 93.72% at 214 nm and 94.85% at 254 nm $^1$H NMR (CDCl$_3$): consistent with structure Anal. cal'd for C35H35BrF2N4O5.0.05 H2O.0.45 Et$_2$O: C, 59.42; H, 5.37; N, 7.53. Found: C, 59.42; H, 5.20; N, 7.47.

EXAMPLE 12

1'-{3-[(4S)-(3,4-Difluorophenyl)-2-oxooxazolidin-3-carbonylamino]propyl}-(2-bromospirofluorene-9,4'-piperidine) (19)

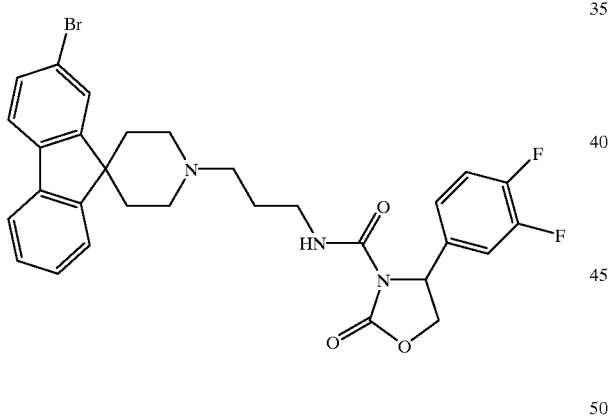

This compound was prepared using the procedure of Example 6, starting with 1'-(3-aminopropyl)-2-bromospirofluorene-9,4'-piperidine, 17 in place of 1'-(3-aminopropyl)spirofluorene-9,4'-piperidine, 8. The title compound, 19, was obtained as a white foam after adding ether/hexane and removing these solvents under reduced pressure.

FAB MS: M+H @ m/e=596.08

HPLC: 96.52% at 214 nm and 100% at 254 nm

Anal. cal'd for C30H28BrF2N3O3: C, 60.41; H, 4.73; N, 7.04. Found: C, 60.28; H, 4.85; N, 6.73.

EXAMPLE 13

2-Fluorospirofluorene-9,4'-piperidine(23)

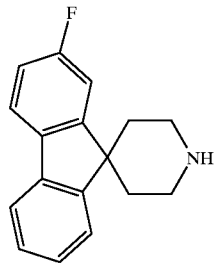

Step 1: 2-Fluorofluorene (21)

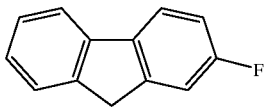

2-Fluoro-9-fluorenone, 20 (1.78 gms, 8.9 mmol) was dissolved in ethylene glycol(60 mL) under a nitrogen atmosphere. Hydrazine hydrate(1.8 mL) was added and the mixture was heated at 180° C. for two hours. The mixture was then cooled and poured into water. The aqueous layer was extracted with ethyl acetate and the organic layer was washed with brine, dried over sodium sulfate, filtered, and concentrated to yield the title compound.

HPLC: 97.85% at 215 nm and 98.76% at 254 nm.

NMR: consistent with structure.

Step 2: Boc-2-fluorospirofluorene-9,4'-piperidine (22)

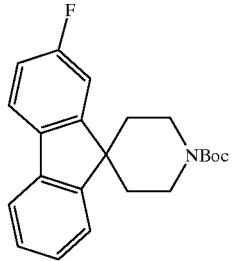

This compound was prepared using the procedure of Example 1, step 1, starting with 2-fluoroflourene, 21 in place of fluorene, 1.

$^1$H NMR (CDCl$_3$): consistent with structure.

Step 3: 2-Fluorospirofluorene-9,4'-piperidine(23)

This compound was prepared using the procedure of Example 1, step 2 starting with Boc-2-fluorospirofluorene-9,4'-piperidine, 22 in place of Boc-spirofluorene-9,4'-piperidine, 2.

FAB MS: M+H @ m/e=254.09

HPLC: 98.87% at 215 nm and 100% at 254 nm

Anal. cal'd for C17H16FN.0.85 H2O.0.35 TFA: C, 68.90; H, 5.90; N, 4,54. Found: C, 68.87; H, 5.92; N, 4.61.

EXAMPLE 14

1,2,3,6-tetrahydro-1-[((2-fluorospirofluorene-9,4'-piperidin)-1'-yl)propyl]aminocarbonyl-5-methoxycarbonyl-4-methoxymethyl-6(S)-(3,4-difluorophenyl)-2-oxopyrimidine (26)

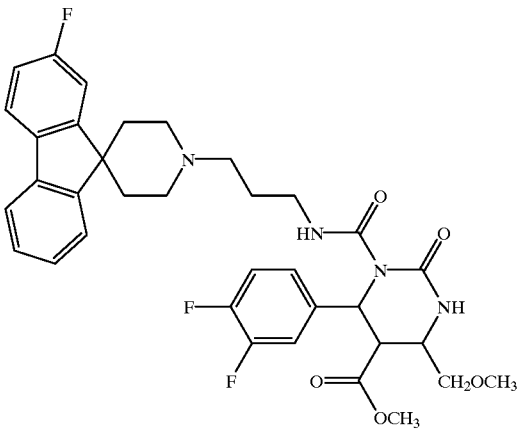

Step 1: 1'-(Boc-3-aminopropyl)-2-fluorospirofluorene-9,4'-piperidine (24)

This compound was prepared using the procedure of Example 6, step 1, starting with 2-fluorospirofluorene-9,4'-piperidine 23 in place of spirofluorene-9,4'-piperidine 3.

Step 2: 1'-(3-Aminopropyl)-2-fluorospirofluorene-9,4'-piperidine (25)

This compound was prepared using the procedure of Example 6, step 2, starting with 1'-(Boc-3-aminopropyl)-2-fluorospirofluorene-9,4'-piperidine 24 in place of 1'-(Boc-3-aminopropyl)spirofluorene-9,4'-piperidine, 7.

Step 3: 1,2,3,6-tetrahydro-1-[((2-fluorospirofluorene-9,4'-piperidin)-1'-yl)propyl]aminocarbonyl-5-methoxycarbonyl-4-methoxymethyl-6(S)-(3,4-difluorophenyl)-2-oxopyrimidine (26)

This compound was prepared using the procedure of Example 8, starting with 1'-(3-aminopropyl)-2-fluorospirofluorene-9,4'-piperidine (25) in place of 1'-(3-aminopropyl)spirofluorene-9,4'-piperidine, 8. The title compound was obtained as a solid.

FAB MS: M+H @ m/e=649.12

HPLC: 94.79% at 214 nm and 95.67% at 254 nm

Anal. cal'd for C35H35F3N4O5: C, 64.81; H, 5.44; N, 8.64. Found: C, 64.60; H, 5.35; N, 8.42.

EXAMPLE 15

1'-{3-[(4S)-(3,4-Difluorophenyl)-2-oxooxazolidin-3-carbonylamino]propyl}-(2-fluorospirofluorene-9,4'-piperidine) (27)

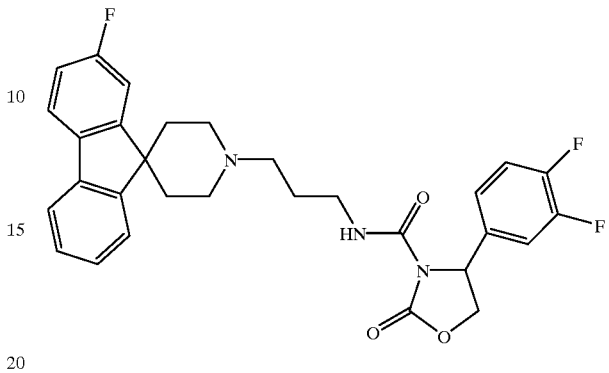

This compound was prepared using the procedure of Example 6, starting with 1'-(3-aminopropyl)-2-fluorospirofluorene-9,4'-piperidine 25 in place of 1'-(3-aminopropyl)spirofluorene-9,4'-piperidine 8. The title compound was obtained as a white foam after adding ether/hexane and removing the solvents under reduced pressure.

FAB MS: M+H @ m/e=536.10

HPLC: 98.72% at 215 nm and 98.77% at 254 nm

Anal. cal'd for C30H28F3N3O3: C, 67.28; H, 5.27; N, 7.85. Found: C, 67.13; H, 5.47; N, 7.61.

EXAMPLE 16

1'-Methyl-spirothioxanthene-9,4'-piperidine (30)

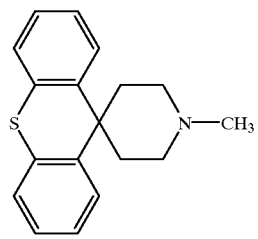

Step 1: Thioxanthene (29)

Thioxanthen-9-one, 28 (14.0 g, 66.0 mmol) was dissolved in THF (186 mL). While under argon, the solution was treated dropwise with 1.0M borane in THF (50 mL, 50.0 mmol) and refluxed (3 hrs). The reaction mixture was cooled, poured into ice (300 g) and extracted with ethyl acetate (3×350 mL). The extracts were combined, washed with brine (1×), dried over $Na_2SO_4$, filtered and concentrated to dryness in vacuo. Treatment of the resulting oil with methanol gave the title compound as a white solid.

$^1$H NMR (CDCl$_3$): δ7.46–7.42 (m, 2H), 7.33–7.30 (m, 2H), 7.23–7.15 (m,4H), 3.86 (s, 2H).

Step 2: 1'-Methyl-spirothioxanthene-9,4'-piperidine (30)

Dry DMSO (80 mL) was added to a flask containing a 60% oil dispersion of NaH (4.8 g, 120 mmol) and the suspension heated to 65° C. for 3 hrs. After cooling to ambient temperature, a DMSO solution (70 mL) of thioxanthene 29 (5.94 g, 30.0 mmol) was added and the resulting red/brown solution stirred for 0.5 hr at ambient temperature. The reaction was cooled to 0° C. and a DMSO solution (60 mL) of mechlorethamine hydrochloride (8.4 g, 44.0 mmol) was added with vigorous stirring for 0.5 hrs. The reaction was quenched in ice/water (500 g) and extracted with ethyl acetate (5×250 mL). The extracts were combined, dried over $Na_2SO_4$, filtered and stripped to dryness in vacuo. Flash chromatography of the crude oil on silica gel (8–10%MeOH in $CH_2Cl_2$) gave the title compound as a solid.

m.p.: 102–3° C., from methanol.

FAB MS: M+H=282.03

HPLC: 100% at 215 nm and 254 nm $^1$H NMR (CDCl$_3$): δ7.54–7.46 (m, 4H), 7.29–7.23 (m, 2H), 7.18–7.13 (m,2H), 2.54 (br s, 8H), 2.28 (s, 3H).

TLC: Silica GF (5% MeOH in $CH_2Cl_2$), $R_f$=0.22, single spot

CHN: Calc'd for: C18H19NS.0.05H$_2$O: C, 76.57; H, 6.82; N, 4.96. Found: C, 76.37; H, 6.65, N, 4.89.

EXAMPLE 17

Spirothioxanthene-9,4'-piperidine (32), .HCl

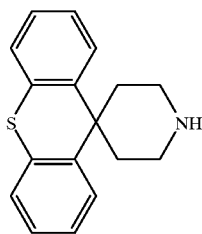

Step 1: 1'-Ethoxycarbonyl-spirothioxanthene-9,4'-piperidine (31)

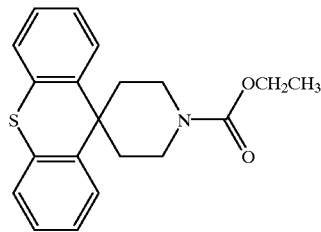

1'-Methyl-spirothioxanthene-9,4'-piperidine, 30 (1.08 g, 3.84 mmol) was treated with ethyl chloroformate (100 mL) and refluxed 16 hrs. Excess ethyl chloroformate was removed in vacuo and the ioly residue was treated with water and extracted with ethyl acetate (3×). The extracts were combined, washed with brine (1×), dried over $Na_2SO_4$, filtered and concentrated to dryness in vacuo. Flash chromatography of the crude oil on silica gel (1%MeOH in $CH_2Cl_2$) gave the title compound as a colorless oil.

TLC: Silica GF ($CH_2Cl_2$), $R_f$=0.34, single spot $^1$H NMR (CDCl$_3$): δ7.51–7.45 (m, 4H), 7.29–7.24 (m, 2H), 7.21–7.15 (m,2H), 4.08–4.04 (q, 4H), 1.26–1.22 (t, 3H).

Step 2: Spirothioxanthene-9,4'-piperidine (32), .HCl

1'-Ethoxycarbonyl-spirothioxanthene-9,4'-piperidine, 31 (742 mg, 2.19 mmol) was dissolved in tert-butanol (25 mL), potassium hydroxide pellets (3.5 g) added and the mixture heated to reflux for 1.5 hrs. The reaction was cooled, the solvent removed in vacuo, the residue treated with water and extracted with ethyl acetate (3×). The extracts were combined, washed with brine (1×), dried over $Na_2SO_4$, filtered and concentrated to dryness in vacuo. Flash chromatography of the crude oil on silica gel (115/10/1 of $CH_2Cl_2$/MeOH/conc. NH$_4$OH) gave a colorless oil. An HCl salt was prepared by dissolving the free base (170 mg, 0.64 mmol) in ethyl acetate (2 mL), treating the solution with 1.0M HCl in ether (0.70 mL, 0.70 mmol), and filtering to collect the HCl salt of the title compound as a fine white solid.

m.p.: >300° C.

FAB MS: M+H=268.15

HPLC: 100% at 215 nm and 254 nm $^1$H NMR (CD$_3$OD): δ7.60–7.54 (m, 4H), 7.41–7.36 (m, 2H), 7.30–7.24 (m, 2H), 3.26–3.23 (m, 4H), 2.63–2.66 (m, 4H).

TLC: Silica GF (80/10/1 of $CH_2Cl_2$/MeOH/conc. NH$_4$OH), $R_f$=0.26, single spot CHN: Calc'd for: C17H17NS.HCl: C, 67.20; H, 5.97; N, 4.61. Found: C, 66.81; H, 5.89; N, 4.51.

EXAMPLE 18

4-(S)-(+)-(3,4-Difluorophenyl)-3-[4-(spirothioxanthen-9,4'-piperidin-1'-yl)-butyl]-oxazolidin-2-one (37)

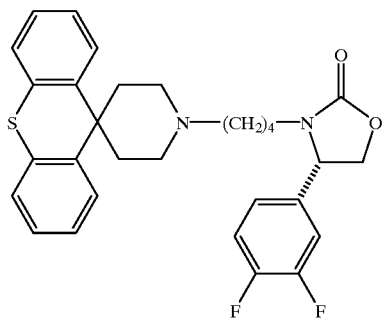

3-(4-bromobutyl)-4-(S)-(3,4-difluorophenyl)-oxazolidin-2-one (50.8 mg, 0.152 mmol) was dissolved in DMF (2 mL), treated with a solution of spirothioxanthene-9,4'-piperidine (32) .HCl (40 mg, 0.132 mmol) and triethylamine (39.6 μl, 0.132 mmol) in DMF and the reaction stirred 42 hrs at ambient temperature. The solvent was removed in vacuo, the residue treated with dilute NaHCO$_3$ (aq) and extracted with ethyl acetate (3×). The extracts were combined, washed with brine (1×), dried over $Na_2SO_4$, filtered and concentrated to dryness in vacuo. Chromatography of the crude oil on silica gel (266/10/1 of $CH_2Cl_2$/MeOH/conc. NH$_4$OH) gave the title compound as a colorless oil (50 mg, 72.8% yield). An HCl salt was prepared by dissolving the free base (50 mg, 0.096 mmol) in ethyl acetate (1 mL), treating the solution with 1.0M HCl in ether (90 μl, 0.09 mmol), and filtering to collect the HCl salt of the title compound as an amorphous white solid.

m.p.: 97–132° C., sinters).

FAB MS: M+H=521.14

HPLC: 100% at 215 nm and 254 nm $^1$H NMR (CD$_3$OD): Consistent with structure plus water and ether TLC: Silica GF (160/10/1 of CH$_2$Cl$_2$/MeOH/conc. NH$_4$OH), R$_f$=0.34, single spot [α]$_D^{20}$=+35.4° in MeOH (conc.=1.13 mg/mL)

CHN: Calc'd for: C30H30F2N2O2S.HCl.H$_2$O.0.15C4H10O: C, 62.69; H, 5.93; N, 4.78. Found: C, 62.35; H, 5.93; N, 4.73.

EXAMPLE 19

4-(S)-(3,4-Difluorophenyl)-3-[5-(spirothioxanthen-9, 4'-piperidin-1'-yl)-pentyl]-oxazolidin-2-one (38), .HCl

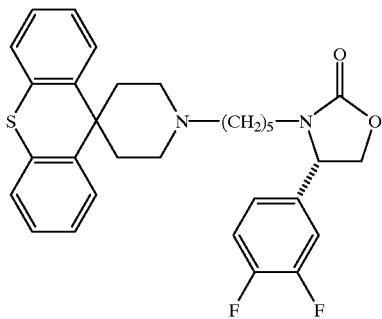

The title compound was prepared as in Example 18 except 3-(5-bromopentyl)-4-(S)-(3,4-difluorophenyl)-oxazolidin-2-one (52.9 mg, 0.152 mmol) was used in place of 3-(4-bromobutyl)-4-(S)-(3,4-difluorophenyl)-oxazolidin-2-one to give the title compound as the HCl salt.

m.p.: 90–130° C., sinters

FAB MS: M+H=535.28

HPLC: 100% at 215 nm and 254 nm $^1$H NMR (CD$_3$OD): Consistent with structure plus water and ether TLC: Silica GF (160/10/1 of CH$_2$Cl$_2$/MeOH/conc. NH$_4$OH), R$_f$=0.34, single spot [α]$_D^{20}$=+33.1° in MeOH (conc.=1.27 mg/mL)

CHN: Calc'd for: C31H32F2N2O2S.HCl.0.5H$_2$O. 0.20C$_4$H$_{10}$O: C, 64.19; H, 6.10; N, 4.71. Found: C, 63.97; H, 6.27; N, 4.85.

EXAMPLE 20

4-(S)-(3,4-Difluorophenyl)-3-[6-(spirothioxanthen-9, 4'-piperidin-1'-yl)-hexyl]-oxazolidin-2-one (39)

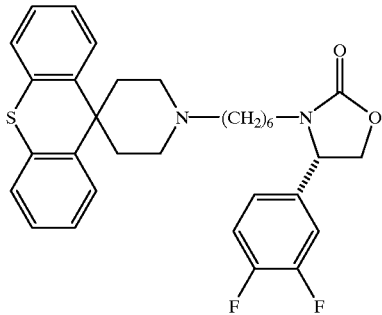

The title compound was prepared as in Example 18 except 3-(6-bromohexyl)-4-(S)-(3,4-difluorophenyl)-oxazolidin-2-one (55.0 mg, 0.152 mmol) was used in place of 3-(4-bromobutyl)-4-(S)-(3,4-difluorophenyl)-oxazolidin-2-one to give the title compound as the HCl salt.

m.p.: 90–130° C., sinters).

FAB MS: M+H=549.30

HPLC: 100% at 215 nm and 254 nm $^1$H NMR (CD$_3$OD): Consistent with structure plus water and ether TLC: Silica GF (160/10/1 of CH$_2$Cl$_2$/MeOH/conc. NH$_4$OH), R$_f$=0.37, single spot [α]$_D^{20}$=+33.80° in MeOH (conc.=1.69 mg/mL)

CHN: Calc'd for C32H34F2N2O2S.HCl.0.6H$_2$O. 0.1C4H10O: C, 64.49; H, 6.21; N, 4.64. Found: C, 64.28; H, 6.28; N, 4.70.

EXAMPLE 21

1'-(3-Aminopropyl)-spirothioxanthene-9,4'-piperidine (34), .2HCl

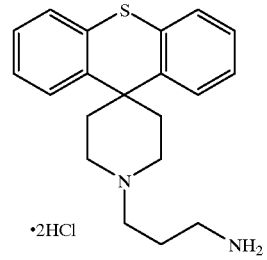

Step 1: 1'-(3-Boc-aminopropyl)-spirothioxanthene-9,4'-piperidine (33)

Spirothioxanthene-9,4'-piperidine, 32 (400 mg, 1.5 mmol) was dissolved in DMF (4 mL), treated with diisopropylethylamine (261 μl, 1.5 mmol) followed by a DMF solution (5 mL) of 3-Boc-aminopropyl bromide (479 mg, 2.01 mmol) and the solution stirred at 45° C. for 18 hrs. The solvent was removed in vacuo, the residue treated with dilute NaHCO$_3$ (aq) and extracted with ethyl acetate (3×). The extracts were combined, washed with brine (1×), dried over Na$_2$SO$_4$, filtered and concentrated to dryness in vacuo. Flash chromatography of the crude oil on silica gel (4% MeOH in CH$_2$Cl$_2$) gave the title compound as a colorless oil.

FAB MS: M+H=425.14

$^1$H NMR (CDCl$_3$): δ7.45–7.45 (m, 4H), 7.28–7.22 (m, 2H), 7.18–7.13 (m, 2H), 5.65–5.61 (br s, NH), 3.21–3.17 (m, 2H) 2.60–2.48 (m, 8H), 2.42–2.37 (t, 2H), 1.68–1.61 (m, 2H) 1.42 (s, 9H).

TLC: Silica GF (4% MeOH in CH$_2$Cl$_2$), R$_f$=0.30, single spot

Step 2: 1'-(3-Aminopropyl)-spirothioxanthene-9,4'-piperidine (34), .2HCl

1'-(3-Boc-aminopropyl)-spirothioxanthene-9,4'-piperidine, 33 (540 mg, 1.27 mmol) was dissolved in ethyl acetate (5 mL) and HCl(g) was bubbled into the solution until saturated. After stirring 1 hr at room temperature, the solvent was removed in vacuo, the residue triturated with ether and filtered to give the title compound as a fine white solid.

m.p.: 270–7° C.

FAB MS: M+H=325.16

HPLC: 100% at 215 nm and 254 nm $^1$H NMR (CD$_3$OD): δ7.60–7.45 (m, 4H), 7.42–7.36 (m, 2H), 7.30–7.25 (m, 2H), 3.23–3.15 (m, 2H), 3.06–3.00 (t, 2H), 2.18–2.06 (m, 2H).

TLC: Silica GF (80/10/1 of CH$_2$Cl$_2$/MeOH/conc. NH$_4$OH), R$_f$=0.21, single spot CHN: Calc'd for: C20H24N2S.2HCl.0.75H$_2$O: C, 58.46; H, 6.75; N, 4.82. Found: C, 58.25; H, 6.59; N, 4.80.

EXAMPLE 22

1'-{3-[(4S)-(3,4-Difluorophenyl)-2-oxooxazolidin-3-carbonylamino]propyl}-(spirothioxanthene-9,4'-piperidine) (35), .HCl

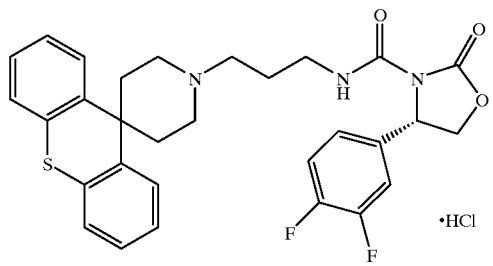

1'-(3-Aminopropyl)-spirothioxanthene-9,4'-piperidine, 34, .2HCl (50 mg, 0.126 mmol) was dissolved in DMF (2 mL), treated with triethylamine (36.9 μL, 0.265 mmol) followed by a DMF (1 mL) solution of 3-(p-nitrophenoxycarbonyl)-4-(S)-(3,4-difluorophenyl)-oxazolidin-2-one (50.3 mg, 0.138 mmol) and stirred 1 hr at room temperature. The solvent was removed in vacuo, the residue treated with ethyl acetate, washed with 0.5N NaOH (aq) (3×) and brine (1×). The organic layer was then dried over Na$_2$SO$_4$, filtered and concentrated to dryness in vacuo. Flash chromatography of the crude oil on silica gel (3%MeOH in CH$_2$Cl$_2$) gave the title compound as a colorless oi. An HCl salt was prepared by dissolving the free base (60 mg, 0.109 mmol) in ethyl acetate (1 mL), treating the solution with 1.0M HCl in ether (120 μL, 0.12 mmol), diluting with ether and filtering to give the HCl salt of the title compound as an amorphous white solid.

m.p.: 140–176° C., sinters.

FAB MS: M+H=549.96

HPLC: 99.5% at 215 nm and 100% at 254 nm $^1$H NMR (CD$_3$OD): Consistent with structure plus water and ether TLC: Silica GF (160/10/1 of CH$_2$Cl$_2$/MeOH/conc. NH$_4$OH), R$_f$=0.31, single spot [α]$_D^{20}$=+41.7° in MeOH (conc.=1.56 mg/mL)

CHN: Calc'd for: C30H29F2N3O3S.HCl.0.45H$_2$O. 0.15C4H10O: C, 60.71; H, 5.40; N, 6.94. Found: C, 60.47; H, 5.60; N, 6.75.

EXAMPLE 23

1,2,3,6-tetrahydro-1-[(spirothioxanthene-9,4'-piperidin-1'-yl)propyl]aminocarbonyl-5-methoxycarbonyl-4-methoxymethyl-6(S)-(3,4-difluorophenyl)-2-oxopyrimidine (36), .HCl

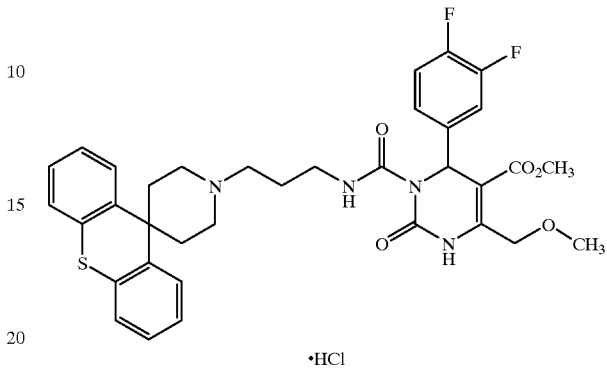

The title compound was prepared using the procedure described in Example 22 except 5-methoxycarbonyl-4-methoxymethyl-1,2,3,6-tetrahydro-2-oxo-6(S)-(3,4-difluorophenyl)-1-(4-nitrophenyloxycarbonyl)pyrimidine (65.9 mg, 0.138 mmol) was used in place of 3-(p-nitrophenoxycarbonyl)-4-(S)-(3,4-difluorophenyl)-oxazolidin-2-one. Flash chromatography on silica gel (2% MeOH in CH$_2$Cl$_2$) gave a colorless oil. The HCl salt was prepared as in Example 22.

m.p.: 140–170° C.

FAB MS: M+H=663.12

HPLC: 99.4% at 215 nm and 100% at 254 nm $^1$H NMR (CD$_3$OD): Consistent with structure plus water and ether TLC: Silica GF (160/10/1 of CH$_2$Cl$_2$/MeOH/conc. NH$_4$OH), R$_f$=0.47, single spot [α]$_D^{20}$=+107.20° in MeOH (conc.=1.60 mg/mL)

CHN: Calc'd for: C35H36F2N4O5S.HCl.1.45H$_2$O. 1.0C4H10O: C, 58.02; H, 5.63; N, 7.65. Found: C, 57.86; H, 5.24; N, 7.35.

EXAMPLE 24

1'-Ethoxycarbonyl-10-oxo-spirothioxanthene-9,4'-piperidine (40)

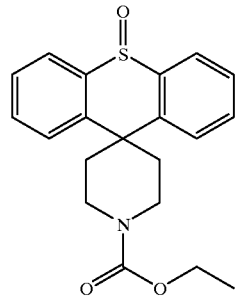

1'-Ethoxycarbonyl-spirothioxanthene-9,4'-piperidine, 31 (230 mg, 0.678 mmol) was dissolved in CHCl$_3$ (1 mL), treated dropwise with a solution of m-chloroperbenzoic acid (137 mg, 0.678 mmol) in CHCl$_3$ (2 mL) and stirred for 1 hr at room temperature. The reaction mixture was chromatographed on silica gel (2%MeOH in CH$_2$Cl$_2$) to give a colorless oil. The title compound was obtained as a crystalline solid from ether.

m.p.=164–5° C. from ether.

FAB MS: M+H=356.12

HPLC: 100% at 215 nm and 254 nm $^1$H NMR (CDCl$_3$): δ8.06–8.01 (m, 2H), 7.56–7.50 (m, 2H), 7.48–7.743 (m, 4H), 4.18–4.09 (m, 4H), 3.26–3.21 (m, 2H), 2.71–2.66 (m, 2H), 1.90–1.86 (m, 2H), 1.30–1.20 (br t, 3H).

TLC: Silica GF (3% MeOH in CH$_2$Cl$_2$), R$_f$=0.30, single spot

CHN: Calc'd for: C20H21NO3S.0.1H$_2$O: C, 67.23; H, 5.98; N, 3.92. Found: C, 66.94; H, 5.96; N, 3.72.

EXAMPLE 25

10-Oxo-spirothioxanthene-9,4'-piperidine (41)

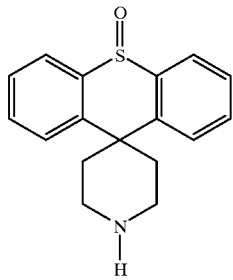

1'-Ethoxycarbonyl-10-oxo-spirothioxanthene-9,4'-piperidine, 40 (205 mg, 0.577 mmol) was dissolved in tert-butanol (8 mL), potassium hydroxide pellets (900 mg) added and the mixture heated to reflux for 1.5 hrs. The reaction was cooled, the solvent removed in vacuo, the residue treated with water and extracted with ethyl acetate (3×). The extracts were combined, washed with brine (1×), dried over Na$_2$SO$_4$, filtered and concentrated to dryness in vacuo to give a crude oil. The title compound was obtained as a crystalline solid from ether.

m.p.: 210–4° C. from ether.

FAB MS: M+H=284.1

HPLC: 100% at 215 nm and 254 nm $^1$H NMR (CDCl$_3$): δ8.06–8.01 (m, 2H), 7.60–7.55 (m, 2H), 7.48–7.740 (m, 4H), 3.56–3.49 (m, 2H), 2.69–2.60 (m, 4H), 1.90–1.85 (m, 2H).

TLC: Silica GF (80/10/1 of CH$_2$Cl$_2$/MeOH/conc. NH$_4$OH), R$_f$=0.35, single spot CHN: Calc'd for: C$_{17}$H$_{17}$NOS.0.2H$_2$O: C, 71.14; H, 6.11; N, 4.88. Found: C, 71.30; H, 6.30; N, 4.58.

EXAMPLE 26

1'-{3-[(4S)-(3,4-Difluorophenyl)-2-oxooxazolidin-3-carbonylamino]propyl}-(10-oxo-spirothioxanthene-9,4'-piperidine) (44), .HCl

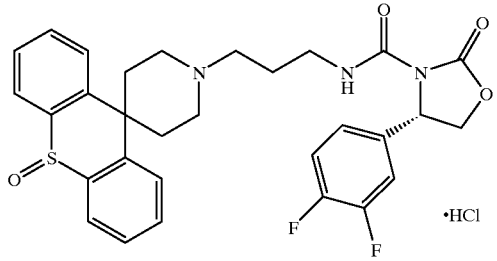

Step 1: 1'-(3-Boc-aminopropyl)-10-oxo-spirothioxanthene-9,4'-piperidine (42)

10-Oxo-spirothioxanthene-9,4'-piperidine, 41 (70.6 mg, 0.249 mmol) was dissolved in DMF (1 mL), treated with diisopropylethylamine (69.5 μl, 0.399 mmol) followed by a DMF solution (1 mL) of 3-Boc-aminopropyl bromide (95.0 mg, 0.399 mmol) and the solution stirred at 45° C. for 18 hrs. The solvent was removed in vacuo, the residue treated with dilute NaHCO$_3$ (aq) and extracted with ethyl acetate (3×). The extracts were combined, washed with brine (1×), dried over Na$_2$SO$_4$, filtered and concentrated to dryness in vacuo. Flash chromatography of the crude oil on silica gel (200/10/1 of CH$_2$Cl$_2$/MeOH/conc. NH$_4$OH) gave the title compound as a colorless oil.

$^1$H NMR (CDCl$_3$): δ8.03–8.00 (m, 2H), 7.57–7.53 (m, 2H), 7.45–7.41 (m, 4H), 5.45 (br s, NH), 3.22–3.18 (m, 2H), 3.08–3.03 (m, 2H), 2.78–2.72 (m, 2H), 2.44–2.40 (t, 2H), 2.24–2.18 (br m, 2H), 1.98–1.92 (m, 2H), 1.68–1.64 (m, 2H).

Step 2: 1'-(3-Aminopropyl)-10-oxo-spirothioxanthene-9,4'-piperidine (43), .2HCl

1'-(3-Boc-aminopropyl)-10-oxo-spirothioxanthene-9,4'-piperidine, 42 (90 mg, 0.204 mmol) was dissolved in ethyl acetate (1 mL) and HCl(g) was bubbled into the solution until saturated. After stirring 0.5 hr at room temperature, the solvent was removed in vacuo, the residue triturated with ether and filtered to give the dihydrochloride of the title compound as a fine white solid.

m.p.: 270–7° C.

TLC: Silica GF (80/10/1 of CH$_2$Cl$_2$/MeOH/conc. NH$_4$OH), R$_f$=0.16, single spot Step 3: 1'-{3-[(4S)-(3,4-Difluorophenyl)-2-oxooxazolidin-3-carbonylamino]propyl}-(10-oxo-spirothioxanthene-9,4'-piperidine) (44), .HCl 1'-(3-Aminopropyl)-10-oxo-spirothioxanthene-9,4'-piperidine (43).2HCl (38 mg, 0.092 mmol) was dissolved in DMF (1 mL), treated with triethylamine (27.0 μL, 0.193 mmol) followed by a DMF (1 mL) solution of 3-(p-nitrophenoxy-carbonyl)-4-(S)-(3,4-difluorophenyl)-oxazolidin-2-one (36.8 mg, 0.101 mmol) and stirred 1 hr at room temperature. The solvent was removed in vacuo, the residue treated with ethyl acetate, washed with 0.5N NaOH (aq) (3×) and brine (1×). The organic layer was then dried over Na$_2$SO$_4$, filtered and concentrated to dryness in vacuo. Flash chromatography of the crude oil on silica gel (266/

EXAMPLE 27

1,2,3,6-tetrahydro-1-[(10-oxo-spirothioxanthene-9,4'-piperidin-1'-yl)propyl]aminocarbonyl-5-methoxycarbonyl-4-methoxymethyl-6(S)-(3,4-difluorophenyl)-2-oxopyrimidine (45), .HCl

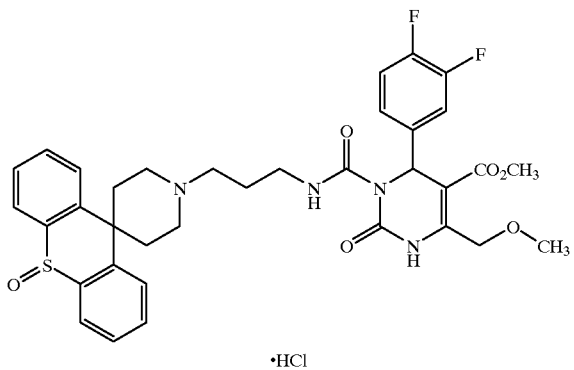

·HCl

The title compound was prepared as the HCl salt using the procedure described in Example 26, Step 3 except 5-methoxycarbonyl-4-methoxymethyl-1,2,3,6-tetrahydro-2-oxo-6(S)-(3,4-difluorophenyl)-1-(4-nitrophenyloxycarbonyl)-pyrimidine was used in place of 3-(p-nitrophenoxy-carbonyl)-4-(S)-(3,4-difluorophenyl)-oxazolidin-2-one. Chromatography on silica gel (266/10/1 of CH$_2$Cl$_2$/MeOH/conc. NH$_4$OH) gave a colorless oil from which the HCl salt was prepared.

m.p.: 185–196° C., foam

FAB MS: M+H=679.07

HPLC: 96.7% at 215 nm and 95.0% at 254 nm $^1$H NMR (CD$_3$OD): Consistent with structure plus water TLC: Silica GF (266/10/1 of CH$_2$Cl$_2$/MeOH/conc. NH$_4$OH), R$_f$=0.20, single spot [α]$_D^{20}$=+116.40° in MeOH (conc.=1.34 mg/mL)

CHN: Calc'd for: C$_{35}$H$_{36}$F$_2$N$_4$O$_6$S.HCl.0.5H$_2$O: C, 58.04; H, 5.29; N, 7.74. Found: C, 57.80; H, 5.52; N, 7.48.

10/1 of CH$_2$Cl$_2$/MeOH/conc. NH$_4$OH) gave a colorless oil. An HCl salt was prepared by dissolving the free base in ethyl acetate, treating the solution with 1.0M HCl in ether, diluting with ether and filtering to give the HCl salt of the title compound as an amorphous white solid.

m.p.: 184–193° C., foam.

FAB MS: M+H=566.06

HPLC: 94.8% at 215 nm and 92.0% at 254 nm $^1$H NMR (CD$_3$OD): Consistent with structure plus water TLC: Silica GF (266/10/1 of CH$_2$Cl$_2$/MeOH/conc. NH$_4$OH), R$_f$=0.19, single spot [α]$_D^{20}$=+42.20° in MeOH (conc.=1.19 mg/mL)

CHN: Calc'd for: C$_{30}$H$_{29}$F$_2$N$_3$O$_4$S.HCl.0.15H$_2$O: C, 59.57; H, 5.05; N, 6.94. Found: C, 59.30; H, 5.43; N, 6.96.

EXAMPLE 28

1'-Methyl-10,10-dioxo-spirothioxanthene-9,4'-piperidine (47)

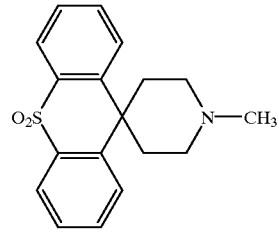

Step 1: 10,10-Dioxo-thioxanthene (46)

Thioxanthene, 29 (2.9 g, 14.6 mmol) was dissolved in glacial acetic acid (90 mL). While under argon, the solution was treated with hydrogen peroxide (6.12 mL, 62.9 mmol of a 35% by wt water solution) and the reaction stirred at 100° C. for 1.5 hr. The reaction was cooled to room temperature, poured into water (250 mL), stirred 0.5 hrs and filtered to give a white solid. The solid was dissolved in CH$_2$Cl$_2$, washed with 5% sodium bisulfite (aq), dried over Na$_2$SO$_4$, filtered and concentrated to dryness in vacuo. Treatment of the resulting oil with methanol gave the title compound as a white solid.

FAB MS: M+H=230.99

$^1$H NMR (CDCl$_3$): δ8.12–8.08 (m, 2H), 7.54–7.44 (m, 6H), 4.27 (s, 2H).

Step 2: 1'-Methyl-10,10-dioxo-spirothioxanthene-9,4'-piperidine (47)

Dry DMSO (34 mL) was added to a flask containing a 60% oil dispersion of NaH (2.03 g, 50.8 mmol) and the suspension heated to 65° C. for 3 hrs. After cooling to room temperature, a DMSO/THF (21/5 mL) solution of 10,10-dioxo-spirothioxanthene, 46 (2.92 g, 12.7 mmol) was added and the resulting red/brown solution stirred for 0.5 hr at room temperature. The reaction was cooled to 0° C. and a DMSO solution (21 mL) of mechlorethamine hydrochloride (3.06 g, 15.9 mmol) was added with stirring at 0° C. for 0.5 hrs, then at room temperature for 16 hrs. The reaction was quenched in ice/water (500 g) and extracted with ethyl acetate (5×250 mL). The extracts were combined, dried over Na$_2$SO$_4$, filtered and stripped to dryness in vacuo. Flash chromatography of the crude oil on silica gel (7% MeOH in CH$_2$Cl$_2$) gave the title compound as a solid.

m.p.: 185–186° C., from acetonitrile.

FAB MS: M+H=314.1

HPLC: 97.22% at 215 nm and 99.0% at 254 nm $^1$H NMR (CDCl$_3$): δ8.22–8.18 (m, 2H), 7.78–7.74 (m, 2H), 7.58–7.48 (m, 4H), 2.78–2.70 (m, 4H), 2.66–2.61(m, 4H), 2.32 (s, 3H).

TLC: Silica GF (80/10/1 of CH$_2$Cl$_2$/MeOH/conc. NH$_4$OH), R$_f$=0.48, single spot CHN: Calc'd for: C$_{18}$H$_{19}$NO$_2$S: C, 68.98; H, 6.11; N, 4.47.

Found: C, 68.65; H, 6.34; N, 4.73.

EXAMPLE 29

1'-Boc-spirothioxanthene-9,4'-piperidine (48)

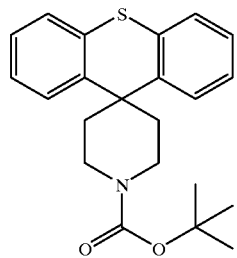

Dry DMSO (40 mL) was added to a flask containing a 60% oil dispersion of NaH (2.22 g, 55.4 mmol) and the suspension heated to 65° C. for 3 hrs. After cooling to room temperature, a DMSO/THF (25/20 mL) solution of thioxanthene, 29 (5.0 g, 25.2 mmol) was added and the resulting red/brown solution stirred for 0.5 hr at room temperature. The reaction was cooled to 0° C. and a DMSO solution (30 mL) of Boc-bis-(2-chloroethyl)amine (7.62 g, 31.5 mmol) was added with stirring at 0° C. for 0.5 hrs, then at room temperature for 4 hrs. The reaction was quenched in ice/water (300 g) and extracted with ethyl acetate (4×250 mL). The extracts were combined, dried over $Na_2SO_4$, filtered and stripped to dryness in vacuo. Chromatography of the crude oil on silica gel (1% MeOH in $CH_2Cl_2$) gave the title compound as a solid.

m.p.: 151–154° C., from acetonitrile.

FAB MS: M+H=368.2

HPLC: 100% at 215 nm and 254 nm $^1$H NMR (CDCl$_3$): δ7.50–7.45 (m, 4H), 7.30–7.24 (m, 2H), 7.20–7.15 (m, 2H), (br s, 4H), 2.42 (br s, 4H), 1.44 (s, 9H).

TLC: Silica GF (10% EtOAc in Hexane), R$_f$=0.30, single spot

CHN: Calc'd for: $C_{22}H_{25}NO_2S$: C, 71.90; H, 6.86; N, 3.81. Found: C, 71.87; H, 6.89; N, 4.00.

EXAMPLE 30

10,10-Dioxo-spirothioxanthene-9,4'-piperidine (50), .HCl

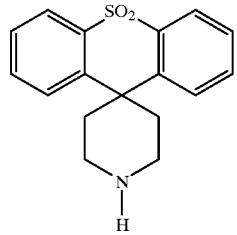

Step 1: 1'-Boc-10,10-dioxo-spirothioxanthene-9,4'-piperidine (49)

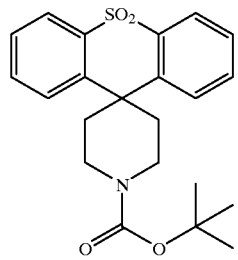

1'-Boc-spirothioxanthene-9,4'-piperidine, 48 (100 mg, 0.272 mmol) was dissolved in CHCl$_3$ (1 mL), cooled to 0° C., treated dropwise with a solution of m-chloroperbenzoic acid (116 mg, 0.571 mmol) in CHCl$_3$ (1 mL) and stirred for 1.5 hrs at room temperature. The reaction mixture was chromatographed on silica gel (1% MeOH in $CH_2Cl_2$) to give a colorless oil.

$^1$H NMR (CDCl$_3$): δ8.24–8.20 (m, 2H), 7.23–7.69 (m, 2H), 7.60–7.74 (m, 4H), 3.80–3.40 (br m, 4H), 2.66–2.58 (br m, 4H), 1.46 (s, 9H).

TLC: Silica GF (1% MeOH in $CH_2Cl_2$), R$_f$=0.24, single spot

Step 2: 10,10-Dioxo-spirothioxanthene-9,4'-piperidine (50), hydrochloride

1'-Boc-10,10-dioxo-spirothioxanthene-9,4'-piperidine, 49 (318 mg, 0.796 mmol) was dissolved in ethyl acetate, treated with a saturated solution of HCl(g) in ethyl acetate (8 mL) and stirred 0.5 hrs at room temperature. The solvent was removed in vacuo, the residue triturated with ethyl acetate and filtered to give the title compound as the HCl salt.

m.p.: 92–194° C.).

FAB MS: M+H=300.08.

HPLC: 100% at 215 nm and 254 nm $^1$H NMR (CD$_3$OD): δ7.60–7.54 (m, 4H), 7.41–7.36 (m, 2H), 7.30–7.24 (m, 2H), 3.26–3.23 (m, 4H), 2.63–2.66 (m, 4H).

TLC: Silica GF (80/10/1 of $CH_2Cl_2$/MeOH/conc. NH$_4$OH), R$_f$=0.29, single spot CHN: Calc'd for: C17H17NO2S.HCl: C, 60.80; H, 5.40; N, 4.17. Found: C, 60.68; H, 5.16; N, 4.05.

EXAMPLE 31

1'-(3-Aminopropyl)-10,10-dioxo-spirothioxanthene-9,4'-piperidine (52),

·2HCl

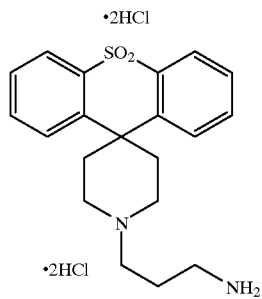

Step 1: 1'-(3-Boc-aminopropyl)-10,10-dioxo-spirothioxanthene-9,4'-piperidine (51)

10,10-Dioxo-spirothioxanthene-9,4'-piperidine, 50 (205 mg, 0.685 mmol) was dissolved in DMF (2 mL), treated with diisopropylethylamine (179 μl, 1.03 mmol) followed by a DMF solution (2 mL) of 3-Boc-aminopropyl bromide (245 mg, 1.03 mmol) and the solution stirred at 45° C. for 18 hrs. The solvent was removed in vacuo, the residue treated with dilute $NaHCO_3$ (aq) and extracted with ethyl acetate (3×). The extracts were combined, washed with brine (1×), dried over $Na_2SO_4$, filtered and concentrated to dryness in vacuo. Chromatography of the crude oil on silica gel (4% MeOH in $CH_2Cl_2$) gave the title compound as a colorless oil.

FAB MS: M+H=457.12

$^1$H NMR ($CDCl_3$): δ8.22–8.18 (m, 2H), 7.78–7.73 (m, 2H), 7.56–7.45 (m, 2H), 5.52–5.48 (br s, NH), 3.24–3.16 (m,2H) 2.73–2.64 (br m, 8H), 2.47–2.42 (t, 2H), 1.70–1.63 (m, 2H) 1.43 (s, 9H).

TLC: Silica GF (4% MeOH in $CH_2Cl_2$), $R_f$=0.32, single spot

Step 2: 1'-(3-Aminopropyl)-10,10-dioxo-spirothioxanthene-9,4'-piperidine (52) .2HCl 1'-(3-Boc-aminopropyl)-10,10-dioxo-spirothioxanthene-9,4'-piperidine, 51 (235 mg, 0.515 mmol) was dissolved in ethyl acetate (5 mL) and treated with a saturated solution of HCl(g) in ethyl acetate (10 mL). After stirring 1 hr at room temperature, the solvent was removed in vacuo, the residue triturated with ether and filtered to give the dihydrochloride of the title compound as a fine white solid.

m.p.: 126–130° C., foam.

FAB MS: M+H=357.13

HPLC: 98.8% at 215 nm and 100% at 254 nm $^1$H NMR ($CD_3OD$): Consistent with structure plus water and ether TLC: Silica GF (80/10/1 of $CH_2Cl_2$/MeOH/conc. $NH_4OH$), $R_f$=0.16, single spot CHN: Calc'd for: C20H24N2O2S.2HCl.H2O.0.3C4H10O: C, 53.73; H, 6.47; N, 5.91. Found: C, 53.51; H, 6.49; N, 5.52.

EXAMPLE 32

1'-{3-[(4S)-(3,4-Difluorophenyl)-2-oxooxazolidin-3-carbonylamino]propyl}-(10,10-dioxo-spirothioxanthene-9,4'-piperidine) (53), .HCl

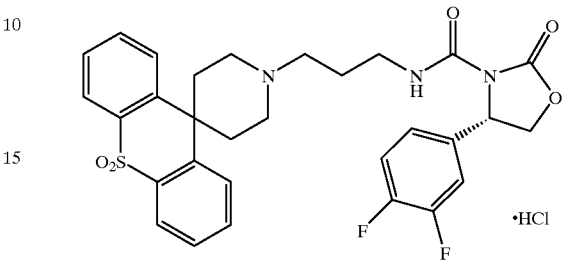

1'-(3-Aminopropyl)-10,10-dioxo-spirothioxanthene-9,4'-piperidine, 52 .2HCl (50 mg, 0.116 mmol) was dissolved in DMF (2 mL), treated with triethylamine (34.0 μL, 0.244 mmol) followed by a DMF (1 mL) solution of 3-(p-nitrophenoxy-carbonyl)-4-(S)-(3,4-difluorophenyl)-oxazolidin-2-one (46.5 mg, 0.128 mmol) and stirred 1 hr at room temperature. The solvent was removed in vacuo, the residue treated with ethyl acetate, washed with 0.5N NaOH (aq) (3×) and brine (1×). The organic layer was then dried over $Na_2SO_4$, filtered and concentrated to dryness in vacuo. Chromatography of the crude oil on silica gel (3%MeOH in $CH_2Cl_2$) gave the title compound as a colorless oil (60 mg, 88.9% yield). An HCl salt was prepared by dissolving the free base (60 mg, 0.103 mmol) in ethyl acetate (1 mL), treating the solution with 1.0M HCl in ether (115 μL, 0.115 mmol), diluting with ether and filtering to give the HCl salt of the title compound as an amorphous white solid.

m.p.: 158–187° C., sinters.

FAB MS: M+H=582.14

HPLC: 100% at 215 nm and 254 nm $^1$H NMR ($CD_3OD$): Consistent with structure plus water and ether TLC: Silica GF (266/10/1 of $CH_2Cl_2$/MeOH/conc. $NH_4OH$), $R_f$=0.20, single spot $[α]D^{20}$=+41.7° in MeOH (conc.=1.20 mg/mL)

CHN: Calc'd as: C30H29F2N3O5S.HCl.0.35H2O.0.25C4H10O: C, 57.91; H, 5.21; N, 6.54. Found: C, 57.61; H, 5.10; N, 6.56.

EXAMPLE 33

1,2,3,6-tetrahydro-1-[(10,10-dioxo-spirothioxanthene-9,4'-piperidin-1'-yl)propyl]aminocarbonyl-5-methoxycarbonyl-4-methoxymethyl-6(S)-(3,4-difluorophenyl)-2-oxopyrimidine (54), .HCl

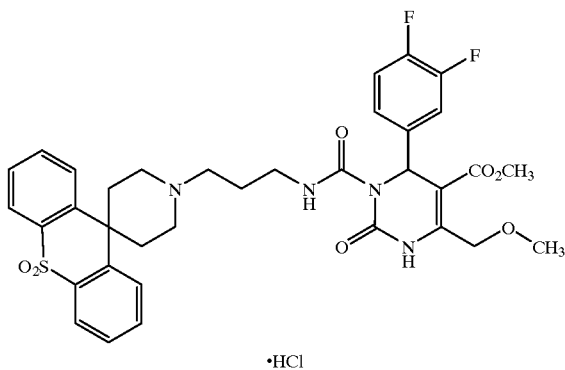

·HCl

The title compound was prepared using the procedure described in Example 32 except 5-methoxycarbonyl-4-methoxymethyl-1,2,3,6-tetrahydro-2-oxo-6(S)-(3,4-difluorophenyl)-1-(4-nitrophenyloxycarbonyl)-pyrimidine (61.1 mg, 0.128 mmol) was used in place of 3-(p-nitrophenoxy-carbonyl)-4-(S)-(3,4-difluorophenyl)-oxazolidin-2-one. Chromatography on silica gel (2% MeOH in $CH_2Cl_2$) gave the title compound as a colorless oil. The HCl salt was prepared as in Example 32.

m.p.: 158–196° C., sinters.

FAB MS: M+H=695.18

HPLC: 100% at 215 nm and 254 nm $^1$H NMR (CD$_3$OD): Consistent with structure plus water and ether TLC: Silica GF (266/10/1 of $CH_2Cl_2$/MeOH/conc. NH$_4$OH), $R_f$=0.26, single spot $[\alpha]D^{20}$=+108.8° in MeOH (conc.=1.37 mg/mL)

CHN: Calc'd for: C35H36F2N4O7S.HCl.0.8H$_2$O.0.15C4H10O: C, 56.50; H, 5.34; N, 7.40. Found: C, 56.22; H, 5.33; N, 7.24.

Scheme 3 shows the preparative procedures employed in Examples 34–44 and the structures of the compounds so prepared.

EXAMPLE 34

Spiroxanthene-9,4'-piperidine (57)

Step 1: 1'-Ethoxycarbonylspiroxanthene-9,4'-piperidine, (56)

1'-Methyl spiroxanthene-9,4'-piperidine, 55 (719 mg, 2.7 mmol), which was prepared as described in J.Med.Chem. 32,2357 (1989), was added to ethyl chloroformate (5 mL) and heated at 80° C. for 20 hours. The cooled reaction was diluted with diethyl ether and washed with 10% aq. HCl. The ethereal layer was dried (Na$_2$SO$_4$) and the solvent evaporated to give 1'-ethoxycarbonylspiroxanthene-9,4'-piperidine, 56 as a viscous oil.

Step 2: Spiroxanthene-9,4'-piperidine (57)

1'-Ethoxycarbonylspiroxanthene-9,4'-piperidine, (56) was dissolved in n-butyl alcohol (8 mL). Potassium hydroxide pellets (1.7 g) were added and this mixture was heated at 85 to 100° C. for 8 hours. Upon cooling this reaction, water was added and the aqueous solution repeatedly extracted with diethyl ether. The ether extract was dried (Na$_2$SO$_4$) and concentrated under vacuum. The residue was triturated with diethyl ether/hexane to give solid product. The mother liquors were treated with HCl saturated ethyl acetate to give additional product as the HCl salt.

m.p.: 242–243° C.

Analysis calc'd for C17H17NO.HCl: C, 70.95; H,6.30; N, 4.87 Found: C, 70.57; H,6.18; N, 4.90.

EXAMPLE 35

1'-{3-[(4S)-(3,4-Difluorophenyl)-2-oxooxazolidin-3-carbonylamino]propyl}spiroxanthene-9,4'-piperidine (60)

Step 1: 1'(3-t-Butoxycarbonylaminopropyl)spiroxanthene-9,4'-piperidine, (58)

A partial suspension of spiroxanthene-9,4'-piperidine, 57 (192 mg, 0.77 mmol) and N-t-butoxycarbonyl-3-bromopropylamine (221 mg, 0.93 mmol) in anhydrous dimethylformamide (2.5 mL) containing triethylamine (0.14 mL, 1 mmol) was warmed at 50° C. for four hours. The reaction mixture was cooled to room temperature, diluted with water and the product was extracted into ethyl acetate. This extract was dried and the solvent evaporated to give the title compound as an oil which was used as is.

Step 2: 1'-(3-Aminopropyl)spiroxanthene-9,4'-piperidine, (59)

Compound 58 from step 1 was dissolved in methylene chloride (6 mL) containing trifluoroacetic acid (2.5 mL) and stirred at room temperature for 15 hours. The solvent was removed under vacuum and the residue was dissolved in chloroform. The chloroform solution was washed with aqeous sodium carbonate, then aqueous sodium hydroxide, dried and filtered through a plug of charcoal and evaporated to give the title compound as an oil.

Step 3: 1'-{3-[(4S)-(3,4-Difluorophenyl)-2-oxooxazolidin-3-carbonylamino]propyl}spiroxanthene-9,4'-piperidine (60)

3-(p-Nitrophenoxycarbonyl)-(4S)-(3,4-difluorophenyl)-oxazolidin-2-one (108 mg, 0.3 mmol) was added to a solution of 1'-(3-aminopropyl)spiroxanthene-9,4'-piperidine, 59 (88 mg, 0.29 mmol) in methylene chloride (5 mL) and stirred for two hours. The reaction was diluted with ethyl acetate, washed with aqueous sodium carbonate and water. The ethyl acetate extract was evaporated and the residue was chromatograghed on silica gel eluting with a 30–100% ethyl acetate/hexane solvent gradient. The isolated material was triturated with diethyl ether/hexane to give the title compound as a flocculent white solid.

m.p.: 138–139° C.

Analysis calc'd for C30H29F2N3O4: C, 67.53; H,5.48; N, 7.88 Found: C, 67.46; H,5.49; N, 7.84.

EXAMPLE 36

1,2,3,6-tetrahydro-1-[(spiroxanthene-9,4'-piperidin-1'-yl)propyl]aminocarbonyl-5-methoxycarbonyl-4-methoxymethyl-6(S)-(3,4-difluorophenyl)-2-oxopyrimidine (61)

5-methoxycarbonyl-4-methoxymethyl-1,2,3,6-tetrahydro-2-oxo-6(S)-(3,4-difluorophenyl)-1-(4- nitrophenyloxycarbonyl)-pyrimidine (142 mg, 0.3 mmol) was added to a solution of 1'-(3-aminopropyl)spiroxanthene-9,4'-piperidine, 59 (89 mg, 0.29 mmol) in methylene chloride (5 mL) and stirred at r.t. for two hours. The reaction was diluted ethyl acetate and washed wtih aq. sodium carbonate and water. This ethyl acetate solution was dried, filtered through a plug of charcoal and evaporated. The residue was chromatographed on silica gel eluting with a 30–100% ethyl acetate/hexane solvent gradient. The purified product was dissolved in chloroform and treated with trifluoroacetic acid to give the trifluoroacetate salt which was isolated as a glass upon evaporation of the solvent.

Analysis calc'd for C35H36F2N4O6.1.15TFA: C,57.59; H,4.81; N, 7.20 Found: C,57.85; H,5.06; N, 6.82.

EXAMPLE 37

1'-[3-(5,5-Bis-p-tolyl-2,4-dioxoimidazolidin-3-yl) propyl]spiroxanthene-9,4'-piperidine (62)

Step 1: Bis-5,5-(4-Methylphenyl)-2,4-imidazolindione

A solution of bis(4-methylphenyl)ketone (1.05 g., 5.0 mmol) in dimethylformamide (10 mL) and water (0.5 mL) containing potassium cyanide (405 mg., 6.2 mmol) and ammonium carbonate (1.6 g., 16.7 mmol) was sealed in a screwed-top glass tubular vessel and heated at 130° C. for 24 hours. The cooled reaction vessel was opened and the contents poured into water and acidified with conc. HCl. The resulting precipitate was collected by filtration, rinsed with water and dried. This solid was digested in ethyl acetate to give purified title product.

mp: >260° C.

Step 2: 3-Bromopropyl-5,5-bis(4-methylphenyl)-2, 4-imidazolindione

Bis-5,5-(4-Methylphenyl)-2,4-imidazolindione (560 mg., 2.0 mmol) was dissolved in dry dimethylforamide (6 mL) and 60% sodium hydride in mineral oil (99 mg., 2.5 mmol) was added. The mixture was warmed at 50° C. for 10 minutes to give a thick precipitate and then 1,3-dibromopropane (1.1 mL, 10.9 mmol) was added. The reaction mixture was warmed at 50° C. for 3 hours. The cooled reaction mixture was diluted with ethyl acetate and the organic solution was washed with aq. NaHCO3 and water (3×). The dried extract was evaporated and chromatographed on silica gel using a 10–30% ethyl acetate/hexane gradient. The appropriate fractions were combined and evaporated and the residue was triturated with hexane/ether to give the title product as a white solid mp: 105–106° C.

Step 3: 1'-[3-(5,5-Bis-p-tolyl-2,4-dioxoimidazolidin-3-yl)propyl]-spiroxanthene-9,4'-piperidine (62)

A solution of spiroxanthene-9,4'-piperidine, 57 (47 mg, 0.187 mmol) and and 3-(3-bromopropyl)-5,5-di-p-tolylhydantoin (80 mg, 0.20 mmol) in dry dimethylformamide (1.5 mL) containing triethylamine (0.04 mL, 0.29 mmol) was warmed at 50° C. for two hours. This reaction was diluted with ethyl acetate, washed with aqueous sodium carbonate, dried and then evaporated. The residue was chromatographed on silica gel eluting with a 25–85% ethyl acetate/hexane solvent gradient. The isolated material was triturated with diethyl ether to give the title compound.

m.p.:172–173° C.

Analysis calc'd for C31H37N3O3.0.25 H2O: C,77.12; H,6.56; N, 7.29 Found: C,77.10; H,6.18; N,7.06.

EXAMPLE 38

2-Chloro-spiroxanthene-9,4'-piperidine (65)

Step 1: 1'-Methyl-2-chloro-spiroxanthene-9,4'-piperidine (63)

A solution of 1'-methyl-spiroxanthene-9,4'-piperidine (55) hydrochloride, (768 mg, 2.54 mmol) and N-chlorosuccinimide (402 mg, 3.0 mmol) in methylene chloride (15 mL) was refluxed for 18 hours. The reaction was diluted with more methylene chloride and washed with aqueous sodium carbonate. This solution was dried,the solvent evaporated and the residue chromatographed on silica gel eluting with a 0.25–0.75% methanol/chloroform solvent gradient to give the title compound.

Step 2: 2-Chloro-spiroxanthene-9,4'-piperidine (65)

The title compund was prepared according to the procedure described in Example 34, Steps 1 and 2, with 1'-methyl-2-chloro-spiroxanthene-9,4'-piperidine (63) used in place of 1'-methyl-spiroxanthene-9,4'-piperidine, 55. m.p.: 136–138° C. The HCl salt was obtained by treatment with HCl saturated ethyl acetate.

m.p.:227–228° C.

Analysis calc'd for C17H16ClNO.HCl.0.15 H2O: C,62.83; H,5.37; N,4.31 Found: C,62.82; H,5.32; N,4.31.

EXAMPLE 39

1'-[3-(5,5-Bis-p-tolyl-2,4-dioxoimidazolidin-3-yl) propyl]-2-chlorospiroxanthene-9,4'-piperidine (70)

The title compound was prepared according to the procedure described in Example 37 wherein 2-chloro-spiroxanthene-9,4'-piperidine, 65 was substituted for spiroxanthene-9,4'-piperidine, 57.

m.p.:204–206° C.

Analysis calc'd for C37H36ClN3O3: C,73.31; H,5.99; N,6.93 Found: C,73.29; H,6.27; N,7.07.

EXAMPLE 40

1'-{3-[(4S)-(3,4-Difluorophenyl)-2-oxooxazolidin-3-carbonylamino]propyl}-2-chlorospiroxanthene-9,4'-piperidine (68)

Step 1: 1'-(3-Aminopropyl)-2-chlorospiroxanthene-9,4'-piperidine (67)

The title compound was prepared in two steps according to the procedures described in Example 35, steps 1 and 2, wherein 2-chlorospiroxanthene-9,4'-piperidine, 65 was substituted for spiroxanthene-9,4'-piperidine, 57. The material was used as is.

Step 2: 1'-{3-[(4S)-(3,4-Difluorophenyl)-2-oxooxazolidin-3-carbonylamino]propyl}-2-chlorospiroxanthene-9,4'-piperidine (68)

The title compound was prepared according to the procedure described in Example 35, step 3, wherein 1'-(3-aminopropyl)-2-chlorospiroxanthene-9,4'-piperidine, 67 was substituted for 1'-(3-aminopropyl)spiroxanthene-9,4'-piperidine, 59.

Analysis calc'd for C30H28ClF2N3O4.0.45 H2O: C,58.82; H,4.92; N,6.86 Found: C,58.81; H,5.04; N,6.61.

EXAMPLE 41

1,2,3,6-tetrahydro-1-[((2-chlorospiroxanthene-9,4'-piperidin)-1'-yl)propyl]aminocarbonyl-5-methoxycarbonyl-4-methoxymethyl-6(S)-(3,4-difluorophenyl)-2-oxopyrimidine (69)

The title compound was prepared according to the procedure described in Example 36, wherein 1'-(3-aminopropyl)-2-chlorospiroxanthene-9,4'-piperidine, 67 was substituted for 1'-(3-aminopropyl)spiroxanthene-9,4'-piperidine, 59. The title compound was obtained as an amorphorous HCl salt Analysis calc'd for C35H35ClF2N4O6.HCl.0.80 H2O: C,57.42; H,5.18; N,7.65 Found: C,57.39; H,4.87; N,7.89.

EXAMPLE 42

1'-{3-[(4S)-(3,4-Difluorophenyl)-2-oxooxazolidin-3-carbonylamino]propyl}-2,7-dichlorospiroxanthene-9,4'-piperidine (76)

Step 1: 1'-Methyl-2,7-dichlorospiroxanthene-9,4'-piperidine, (71)

A solution of 1'-methyl spiroxanthene-9,4'-piperidine hydrochloride, 55 (388 mg, 1.28 mmol) and N-chlorosuccinimide (376 mg, 2.81 mmol) in methylene chloride (10 mL) was refluxed for 20 hours. More N-chlorosuccinimide (187 mg, 1.4 mmol) was added and the reaction was refluxed for another 20 hours. The cooled reaction was diluted with more methylene chloride and washed with aqueous sodium carbonate. This solution was dried, the solvent evaporated, and the residue chromatographed on silica gel eluted with a 0.3% methanol/chloroform saturated with ammonia to give the title compound as an oil which was used as is.

Step 2: 2,7-Dichloro-spiroxanthene-9,4'-piperidine (73)

1'-Methyl-2,7-dichlorospiroxanthene-9,4'-piperidine, (71) was treated according to the procedure described in Example 34, Steps 1 and 2 to give the title compound as an oil which was used as is.

Step 3: 1'-(3-Aminopropyl)-2,7-dichlorospiroxanthene-9,4'-piperidine (75)

The title compound was prepared in two steps according to the procedures described in Example 35, steps 1 and 2, wherein 2,7-dichlorospiroxanthene-9,4'-piperidine, 73 was substituted for spiroxanthene-9,4'-piperidine, 57. The oily material was used as is.

Step 4: 1'-{3-[(4S)-(3,4-Difluorophenyl)-2-oxooxazolidin-3-carbonylamino]propyl}-2,7-dichlorospiroxanthene-9,4'-piperidine (76)

The title compound was prepared according to the procedure described in Example 35, step 3, wherein 1'-(3-aminopropyl)-2,7-dichlorospiroxanthene-9,4'-piperidine, 75 was substituted for 1'-(3-aminopropyl)spiroxanthene-9,4'-piperidine, 59. The title compound was obtained as an amorphorous HCl salt.

Analysis calc'd for C30H27Cl2F2N3O4.HCl.0.35 H2O: C,55.84; H,4.48; N,6.51 Found: C,55.86; H,4.67; N,6.40.

EXAMPLE 43

2,7-Difluorospiroxanthene-9,4'-piperidine (80)

Step 1: 2,7-Difluoroxanthene (78)

A solution of 2,7-difluoroxanthone, 77 (1.18 g, 5.08 mmol) (obtained according to the preparation described in J. Org. Chem. 40, 2088 (1975)) in tetrahydrofuran (12 mL) containing 1 M borane in THF (3.6 mL, 3.6 mmol) was refluxed for five hours. Methanol was carefully added to the cooled mixture to quench the reaction. Water was then added and the product extracted into diethyl ether. The ethereal solution was dried, filtered through a plug of charcoal, and the solvent removed under vacuum. The residue was triturated with hexane/methanol to give the title compound.

m.p.: 117–118° C.

Step 2: 1'-t-Butoxycarbonyl-2,7-difluorospiroxanthene-9,4'-piperidine (79)

Sodium hydride in mineral oil (60%, 413 mg, 10.3 mmol) was dissolved in dry dimethyl sulfoxide (10 mL) by heating at 60° C. for two hours. This solution was cooled to room temperature and a solution of 2,7-difluoroxanthene, 78 (936 mg, 4.29 mmol) in tetrahydrofuran (8 mL) was added dropwise to give a deep red solution. After cooling this mixture in an ice bath, a solution of N-t-butoxycarbonyl-bis-(2-chloroethyl)amine (1.25 g, 5.16 mmol) in tetrahydrofuran (8 mL) was added dropwise as the red coloration dissipated. The reaction was allowed to warm to room temperature over two hours. After addition of water, the crude product was extracted into diethyl ether and the ethereal solution washed with water, 10% aqueous HCl, and the solution dried and filtered through a plug of charcoal. Removal of the solvent under vacuum afforded a residue which was chromatographed on silica gel eluting with a 2–9% ethyl acetate/hexane solvent gradient to give the title compound as a crystalline solid upon trituration with hexane.

m.p.: 90–92° C.

Step 3: 2,7-Difluorospiroxanthene-9,4'-piperidine (80) hydrochloride 1'-t-Butoxycarbonyl-2,7-Difluorospiroxanthene-9,4'-piperidine, 79 (966 mg, 2.5 mmol) was dissolved in ethyl acetate (3 mL) and ethyl acetate saturated with HCl gas (5 mL) was added. Upon stirring, the crystalline HCl salt of the title compound precipitated.

m.p.: >260° C.

Analysis calc'd for C17H15F2NO.HCl: C,63.06; H,4.98; N,4.33 Found: C,62.97; H,5.01; N,4.21.

EXAMPLE 44

1'-{3-[(4S)-(3,4-Difluorophenyl)-2-oxooxazolidin-3-carbonylamino]propyl}-2,7-difluorospiroxanthene-9,4'-piperidine (83)

The title compound was prepared according to the procedures described in Example 35, Steps 1–3, with 2,7-difluorospiroxanthene-9,4'-piperidine, 80 substituted for spiroxanthene-9,4'-piperidine, 57. The title compound was obtained as an amorphorous HCl salt.

Analysis calc'd for C30H27F4N3O4.HCl.0.45 H2O: C,58.67; H,4.74; N,6.84 Found: C,58.67; H,4.55; N,6.73.

Scheme 4 shows the preparative procedures employed in Examples 45–53 and the structures of the compounds so prepared.

EXAMPLE 45

Spiro-5H-indeno[1,2-b]pyridine-5,4'-piperidine (86)

Step 1: 1'-(t-Butoxycarbonyl)-(spiro-5H-indeno[1,2-b]pyridine)-5,4'-piperidine (85)

To a three-neck round bottom flask, equipped with a septum, addition funnel, and condenser, was added sodium hydride (60% in mineral oil, 112 mg, 2.8 mmol) under an atmosphere of nitrogen. Dimethylsulfoxide (3 mL) was added and the slurry warmed to 60° C. After one hour the greenish solution was cooled to 0° C. and THF (1 mL) was added. Once cool, 5H-indeno[1,2-b]pyridine, 84 (J. Org. Chem. 51, 2021 (1986)) (233 mg, 1.39 mmol, dissolved in THF/DMSO (4 mL)) was added dropwise yielding a red solution. This solution was stirred 15 minutes and t-Boc-bis (2-chloroethyl)amine (337 mg, 1.39 mmol) in 2 mL of THF was added dropwise. The mixture was warmed to ambient temperature and stirred for 3 hours, then diluted with ethyl acetate and quenched with saturated aqueous sodium bicarbonate. The layers were separated and the organic layer washed with saturated aqueous sodium bicarbonate (3×) and brine (1×). The organic layer was dried over sodium sulfate, filtered, and evaporated to dryness. The resulting oil was purified by chromatography on silica gel eluted with 30% ethyl acetate/hexane. The product fractions were evaporated to dryness to yield the title compound as an oil.

Step 2: Spiro-5H-indeno[1,2-b]pridine-5,4'-piperidine (86)

1'-(t-Butoxycarbonyl)-(spiro-5H-indeno[1,2-b]pyridine)-5,4'-piperidine, 85 (120 mg, 0.36 mmol) was dissolved in 2 mL of ethyl acetate and cooled in an ice bath. The solution was treated with 5 mL of sat'd HCl/ethyl acetate solution and allowed to stir for 30 minutes. The mixture was evaporated in vacuo and the residue partitioned between ethyl acetate and saturated aqueous sodium bicarbonate. The phases were separated and the water layer was extracted with ethyl acetate (2×). The organic layers were combined, washed with brine, dried over sodium sulfate, filtered, and evaporated to dryness. The resulting oil was purified by chromatography on silica gel eluted with 93:7:0.7 of methylene chloride: methanol: ammonium hydroxide. The product fractions were evaporated to dryness to yield the title compound as a white solid.

m.p.: 115–119° C.

NMR: consistent with structure

HPLC: 97% pure

FAB MS: M+H @ m/e=237.08

Anal. cal'd for C16H16N2.0.10 H2O: C, 80.70; H, 6.86; N, 11.77. Found: C, 80.83; H, 6.78; N, 11.74.

EXAMPLE 46

1'-{5-[(4(S)-(3,4-difluorophenyl)-2-oxooxazolidin)-3-yl]-pentyl}-(spiro-5H-indeno[1,2-b]pyridine)-5,4'-piperidine (87), dihydrochloride Spiro-5H-indeno[1,2-b]pyridine-5,4'-piperidine, 86 (54 mg, 0.23 mmol), 3-(5-bromopentyl)-4(S)-(3,4-difluorophenyl)-oxazolidin-2-one (85 mg, 0.24 mmol), and triethylamine (45 µL, 0.32 mmol) were combined in 3 mL of DMF and stirred at 40° C. for 18 hours. The reaction was concentrated in vacuo, and the resulting residue was partitioned between ethyl acetate and saturated aqueous sodium bicarbonate. The phases were separated and the organic phase was washed with saturated aqueous sodium bicarbonate and brine. The organic layer was dried over sodium sulfate, filtered, and evaporated to dryness. The resulting oil was purified by chromatography on silica gel eluted with 96:4:0.4 of methylene chloride:methanol:ammonium hydroxide. The product fractions were evaporated to dryness and the resulting residue was treated with HCl/ethyl acetate. The mixture was evaporated to dryness and the residue was reconcentrated from ethyl ether, then triturated with ethyl ether and filtered to give the dihydrochloride of the title compound as a white solid.

m.p.: 149–170° C.

NMR: consistent with structure

HPLC: 100% pure

FAB MS: M+H @ m/e=504.31

Anal. cal'd for C30H31F2N3O2.2HCl.0.75 H2O: C, 61.06; H, 5.89; N, 7.12. Found: C, 61.06; H, 5.98; N, 7.09.

EXAMPLE 47

1'-(3-aminopropyl)-(spiro-5H-indeno[1,2-b]pyridine)-5,4'-piperidine (89), trihydrochloride)

Step 1: 1'-(3-(t-butoxycarbonylamino)propyl-(spiro-5H-indeno[1,2-b]pyridine)-5,4'-piperidine (88)

Spiro-5H-indeno[1,2-b]pyridine-5,4'-piperidine, 86 (232 mg, 0.98 mmol) and N-t-butoxycarbonyl-3-bromopropylamine (253 mg, 1.06 mmol) were combined in DMF. The reaction mixture was treated with triethylamine (185 mL, 1.32 mmol) and warmed to 50° C. for 16 hours. The reaction solution was evaporated to dryness and the resulting residue was partitioned between ethyl acetate and saturated aqueous sodium bicarbonate. The phases were separated and the organic phase was washed with saturated aqueous sodium bicarbonate and brine. The organic layer was dried over sodium sulfate, filtered, and evaporated to dryness. The resulting oil was purified by chromatography on silica gel eluted with 96:4 of methylene chloride:methanol. The product fractions were evaporated to dryness to yield the title product as a white foam.

Step 2: 1'-(3-aminopropyl)-(spiro-5H-indeno[1,2-b]pyridine)-5,4'-piperidine (89) trihydrochloride 1'-(3-(t-butoxycarbonylamino)propyl-(spiro-5H-indeno[1,2-b]pyridine)-5,4'-piperidine, 88 (360 mg, 0.91 mmol) was dissolved in 2 mL of ethyl acetate and cooled in an ice bath. The solution was treated with 5 mL of saturated HCl/ethyl acetate solution and allowed to stir for 30 minutes. The mixture was evaporated in vacuo and the resulting residue was partitioned between methylene chloride and saturated aqueous sodium carbonate. The phases were separated and the water layer was extracted with methylene chloride (2×). The oraganic phases were combined and washed with brine, dried over sodium sulfate, filtered, and evaporated to dryness. The resulting residue was treated with HCl/ethyl acetate, evaporated to dryness, and the residue crystallized from methanol to yield the trihydrochloride of the title compound as a white solid.

m.p.: 255–280° C.

NMR: consistent with structure

HPLC: 100% pure

FAB MS: M+H @ m/e=294.28

Anal. cal'd for C19H23N3.3HCl.0.55 H2O: C, 55.29; H, 6.62; N, 10.18. Found: C, 55.35; H, 6.44; N, 10.12.

EXAMPLE 48

1'-{3-[(4S)-(3,4-Difluorophenyl)-2-oxooxazolidin-3-carbonylamino]propyl}-(spiro-5H-indeno[1,2-b]pyridine)-5,4'-piperidine (90), dihydrochloride 1'-(3-Aminopropyl)-(spiro-5H-indeno[1,2-b]pyridine)-5,4'-piperidine (89) trihydrochloride (60 mg, 0.20 mmol), 3-(p-nitrophenoxycarbonyl)-4-(S)-(3,4-difluorophenyl)- oxazolidin-2-one (76 mg, 0.21 mmol), and triethylamine (35 mL, 0.25 mmol) were combined in 4 mL of THF. The yellow mixture was stirred at ambient temperature for 18 hours, then concentrated in vacuo. The resulting oil was purified by chromatography on silica gel eluted with ethyl acetate followed by methylene chloride, 99:1, 98:2, and 95:5 of methylene chloride:methanol. The product fractions were evaporated to dryness and the resulting residue was treated with HCl/ethyl acetate, evaporated to dryness. The residue was reconcentrated from ethyl ether, then triturated with ethyl ether and filtered to give the title compound.

m.p.: 182–195° C.

NMR: consistent with structure

HPLC: 100% pure

FAB MS: M+H @ m/e=519.33

Anal. cal'd for $C_{29}H_{28}F_2N_4O_3 \cdot 2HCl \cdot 0.60\ H_2O$: C, 57.83; H, 5.22; N, 9.30. Found: C, 57.84; H, 5.21; N, 9.21.

EXAMPLE 49

1,2,3,6-tetrahydro-1-[3-(spiro(5H-indeno[1,2-b] pyridine)-5,4'-piperidin)-1'-yl) propylaminocarbonyl]-5-methoxycarbonyl-4-methoxymethyl-6(S)-(3,4-difluorophenyl)-2-oxopyrimidine (91) dihydrochloride The title compound was prepared according to the procedure of Example 36 with 1'-(3-aminopropyl)-(spiro-5H-indeno[1,2-b]pyridine)-5,4'-piperidine (89) used in place of 1'-(3-aminopropyl)spiroxanthene-9,4'-piperidine, 59. In place of the TFA salt, the crude product was converted to a dihydrochloride salt by treatment with HCl/ethyl acetate, evaporation to dryness, and trituration with ether.

m.p.: 157–180° C.

NMR: consistent with structure

HPLC: 100% pure

FAB MS: M+H @ m/e=632.41

Anal. cal'd for $C_{34}H_{35}F_2N_5O_5 \cdot 2HCl \cdot 0.60\ H_2O$: C, 57.08; H, 5.38; N, 9.79. Found: C, 57.09; H, 5.47; N, 9.83.

EXAMPLE 50

Spiro-9H-indeno[2,1-b]pyridine-9,4'-piperidine (95), dihydrochloride

Step 1: 9H-indeno[2,1-b]pyridine (93)

Indeno[2,1-b]pyridin-9-one (525 mg, 2.90 mmol), 92 (J. Org. Chem. 51, 2021 (1986)) and 4.5 mL of hydrazine hydrate were combined in a sealed tube and warmed to 180° C. for 16 hours. The resulting mixture was diluted with chloroform and the layers seperated. The organics were dried over sodium sulfate, filtered, and evaporated to dryness. The resulting oil was purified by chromatography on silica gel eluted with 95:5, 93:7, and 90:10 of methylene chloride:ethyl ether. The product fractions were evaporated to dryness to yield the title compound as a yellow solid.

Step 2: 1'-(t-butoxycarbonyl)-(spiro-9H-indeno[2,1-b]pyridine)-9,4'-piperidine (94)

The title compound was prepared by the procedure of Example 45, Step 1 with 9H-indeno[2,1-b]pyridine, 93 used in place of 5H-indeno[1,2-b]pyridine, 84.

Step 3: Spiro-9H-indeno[2,1-b]pyridine-9,4'-piperidine (95), dihydrochloride

1'-(t-Butoxycarbonyl)-(spiro-9H-indeno[2,1-b]pyridine)-9,4'-piperidine, 94 (130 mg, 0.39 mmol) was dissolved in 2 mL of ethyl acetate and cooled in an ice bath. The solution was treated with 5 mL of saturated HCl/ethyl acetate solution and allowed to stir for 30 minutes. The reaction mixture was evaporated in vacuo to yield the dihydrochloride of the title compound as a yellow solid.

m.p.: 238–245° C.

NMR: consistent with structure

HPLC: 100% pure

FAB MS: M+H @ m/e=237.08

Anal. cal'd for $C_{16}H_{16}N_2 \cdot 2HCl \cdot 0.10\ EtOAc \cdot 0.20\ H_2O$: C, 61.23; H, 6.02; N, 8.71. Found: C, 61.21; H, 6.23; N, 8.60.

EXAMPLE 51

1'-(3-aminopropyl)-(spiro-9H-indeno[2,1-b] pyridine)-9,4'-piperidine (97) trihydrochloride Step 1: 1'-(3-t-butoxycarbonylaminopropyl)-(spiro-9H-indeno[2,1-b]pyridine)-9,4'-piperidine (96)

The title compound was prepared by the procedure of Example 47, Step 1 with spiro-9H-indeno[2,1-b]pyridine-9, 4'-piperidine (95) used in place of spiro-5H-indeno[1,2-b] pyridine-5,4'-piperidine, 86

Step 2: 1'-(3-aminopropyl)-(spiro-9H-indeno[2,1-b] pyridine)-9,4'-piperidine (97) trihydrochloride The title compound was prepared by the procedure of Example 47, Step 2 with 1'-(3-t-butoxycarbonylaminopropyl)-(spiro-9H-indeno[2,1-b] pyridine)-9,4'-piperidine (96) used in place of 1'-(3-t-butoxycarbonylaminopropyl)-(spiro-5H-indeno[1,2-b] pyridine)-5,4'-piperidine (88)

EXAMPLE 52

1'-{3-[(4S)-(3,4-Difluorophenyl)-2-oxooxazolidin-3-carbonylamino]propyl}-(spiro-9H-indeno[2,1-b] pyridine)-9,4'-piperidine (98)

The title compound was prepared by the procedure of Example 48 with 1'-(3-aminopropyl)-spiro(9H-indeno[2,1-b]pyridine)-9,4'-piperidine (97) trihydrochloride used in place of 1'-(3-aminopropyl)-(spiro-5H-indeno[1,2-b] pyridine)-5,4'-piperidine (89) trihydrochloride.

m.p.: 140–157° C.

NMR: consistent with structure

HPLC: 93% pure

FAB MS: M+H @ m/e=519.33

Anal. cal'd for $C_{29}H_{28}F_2N_4O_3 \cdot 2HCl \cdot 0.95\ H_2O \cdot 0.30\ EtOAc \cdot 0.30\ Et_2O$: C, 57.38; H, 5.72; N, 8.52. Found: C, 57.35; H, 5.75; N, 8.47.

EXAMPLE 53

1,2,3,6-tetrahydro-1-[3-((spiro(9H-indeno[2,1-b] pyridine)-9,4'-piperidin)-1'-yl) propylaminocarbonyl]-5-methoxycarbonyl-4-methoxymethyl-6(S)-(3,4-difluorophenyl)-2-oxopyrimidine (99) dihydrochloride The title compound was prepared according to the procedure of Example 36 with 1'-(3-aminopropyl)-spiro(9H-indeno[2,1-b]pyridine)-9,4'-piperidine (97) used in place of 1'-(3-aminopropyl)-spiroxanthene-9,4'-piperidine, 59.

m.p.: 201–209° C.

NMR: consistent with structure

HPLC: 100% pure

FAB MS: M+H @ m/e=632.41

Anal. cal'd for C34H35F2N5O5.2HCl.0.40 H2O.0.15 Et2O: C, 57.48; H, 5.48; N, 9.69. Found: C, 57.45; H, 5.56; N, 9.75.

Scheme 5 show the preparative procedures employed in Examples 54–58 and the structure of the compounds so prepared.

EXAMPLE 54

10,11-dihydrospiro-5H-dibenzo[a,d]cycloheptene-5, 4'-piperidine (109), hydrochloride

Step 1: 5-(2-dimethylaminoethyl)-10,11-dihydro-5H-dibenzo[a,d]cycloheptene-5-carbonitrile (101)

To a solution of 10,11-dihydro-5H-dibenzo[a,d]cycloheptene-5-carbonitrile (100) (Med. Chem. Res. 1, 401 (1991)) (1.0 g, 4.56 mmol) and N-(2-chloroethyl)-N,N-dimethylamine hydrochloride (0.72 g, 5 mmol) in benzene (20 mL) was added 8.8 mL of a 1.3M solution of lithium hexamethyldisilazide (11.4 mmol). The mixture was heated at reflux under nitrogen for 18 hr and the solvent then removed under vacuum. The residue was treated with water (20 mL) and extracted twice with methylene chloride (20 mL). The organic layers were combined, dried over sodium sulfate, and chromatographed directly on silica gel eluted with methylene chloride followed by 95:5:0.5, then 90:10:1 methylene chloride:methanol:ammonium hydroxide. The product fractions were evaporated to dryness in vacuo to give the title compound as a yellow oil.

Step 2: 5-(2-dimethylaminoethyl)-10,11-dihydro-5H-dibenzo[a,d]cycloheptene-5-carbaldehyde (102)

To a solution of 5-(2-dimethylaminoethyl)-10,11-dihydro-5H-dibenzo[a,d]cycloheptene-5-carbonitrile (101) (4.15 g, 14.3 mmol) in 50 mL of $CH_2Cl_2$ stirred at −78° C. and maintained under a nitrogen atmosphere was added diisobutylaluminum hydride (20.6 mL of a 1.0M solution in $CH_2Cl_2$; 20.6 mmol) dropwise. The mixture was stirred at −78° C. for 30 minutes, warmed to 0° C. and left stir an additional 4 hours. The solution was poured into 35 mL of saturated aqueous ammonium chloride. The resulting gelatinous mixture was stirred vigorously for 15 minutes, then 65 mL of 1.5N sulfuric acid was added and the mixture stirred overnight. The mixture was extracted with CH2Cl2 (3×), and the combined organic layers were washed with saturated aqueous sodium bicarbonate and brine, dried the over sodium sulfate, filtered, and evaporated do dryness. The resulting oil was purified by chromatography on silica gel with 96/4/0.4 of methylene cloride/methanol/ammonium hydroxide. The product fractions were evaporated to dryness to yield the title product as an oil.

Step 3: [2-(5-[1,3]dithian-2-ylidenemethyl-10,11-dihydro-5H-dibenzo[a,d]cyclohepten-5-yl)-ethyl]-dimethylamine (103)

To a solution of 2-trimethylsilyl-1,3-dithiane (2.5 mL, 12.8 mmol) in 10 mL of THF stirred at −78° C. and maintained under a nitrogen atmosphere was added butyl-lithium (5.1 mL of a 2.5M solution in hexane; 12.8 mmol) dropwise. The mixture was stirred in the cold for 20 minutes and then treated with 5-(2-dimethylamino-ethyl)-10,11-dihydro-5H-dibenzo[a,d]cycloheptene-5-carbaldehyde (102), 3.1 g in 20 mL of THF; 10.6 mmol) added dropwise. The solution was stirred for 1.5 hours at −78° C., warmed to ambient temperature and stirred an additional 1.5 hours. The solution was diluted with ethyl ether and quenched with saturated aqueous ammonium chloride. The organic layer was washed with saturated aqueous ammonium chloride (1×), saturated aqueous sodium bicarbonate (1×), and brine (1×), dried the over sodium sulfate, filtered, and evaporated to dryness. The resulting oil was purified by chromatography on silica gel (95:5 of methylene chloride:methanol). The product fractions were evaporated to dryness to yield the title product as an oil.

Step 4: [5-(2-dimethylaminethyl)-10,11-dihydro-5H-dibenzo[a,d]cyclohepten-5-yl]-thioacetic acid-S-(3 mercapto-propyl)ester (104)

To a solution of [2-(5-[1,3]dithian-2-ylidenemethyl-10, 11-dihydro-5H-dibenzo[a,d]cyclohepten-5-yl)-ethyl]-dimethylamine (103), 2.94 g, 7.43 mmol) in 37 mL of methanol was added 37 mL of 1M hydrochloric acid. The solution was heated to reflux for 2 hours, cooled, and evaporated to dryness. The resulting residue was partitioned between ethyl acetate and saturated aqueous sodium bicarbonate. The phases were separated and the organic phase was washed with saturated aqueous sodium bicarbonate and brine, dried over sodium sulfate, filtered, and evaporated to dryness to yield the title product as an oil.

Step 5: 2-[5-(2-dimethylaminoethyl)-10,11-dihydro-5H-dibenzo[a,d]cyclohepten-5-yl]ethanol (105)

To a solution of [5-(2-dimethylaminoethyl)-10,11-dihydro-5H-dibenzo[a,d]cyclohepten-5-yl]-thioacetic acid-S-(3 mercapto-propyl)ester (104), 3.1 g, 7.5 mmol) in 50 mL of THF, maintained under an argon atmosphere, was added lithium aluminum hydride (37.5 mL of a 1M solution in THF; 37.5 mmol) dropwise. The clear solution was refluxed for 5 hours and then cooled to 0° C. The mixture was diluted with ethyl acetate and quenched with 10% sodium hydroxide. The resulting slurry was filtered over celite and the organic layer was washed with saturated aqueous sodium bicarbonate and brine, dried the over sodium sulfate, filtered, and evaporated to dryness. The resulting oil was purified by chromatography on silica gel (95:5:0.5 of methylene chloride:methanol:ammonium hydroxide). The product fractions were evaporated to dryness to yield the title product. as an oil.

Step 6: N,N-dimethyl-(10,11-dihydrospiro-5H-dibenzo[a,d]cycloheptene)-5,4'-piperidinium chloride (106)

To a solution 2-[5-(2-dimethylaminoethyl)-10,11-dihydro-5H-dibenzo[a,d]cyclohepten-5-yl]ethanol (105, 1.8 g, 5.8 mmol) in 40 mL of 1:1 carbon tetrachloride:acetonitrile, maintained under a nitrogen atmosphere, were added triphenylphosphine (2.08 g, 7.9 mmol) and triethylamine (300 mL, 2.16 mmol). The mixture was stirred for 5 hours and then evaporated to dryness. The addition and evaporation of ethyl ether several times yielded the title compound as a yellow foam.

Step 7: N-methyl-(10,11-dihydrospiro-5H-dibenzo[a,d]cycloheptene)-5,4'-piperidine (107)

N,N-Dimethyl-(10,11-dihydro-5H-dibenzo[a,d]cycloheptene)-5,4'-piperidinium chloride (106, 1.9 g, 5.8 mmol) was heated to 250° C. under high vacuum in a kugelrohr distillation apparatus. Heating was continued for 1 hour. The residue remaining in the collection bulbs and reaction flask was purified by chromatography on silica gel (95:5:0.5 of methylene chloride:methanol:ammonium hydroxide). The product fractions were evaporated to dryness to yield the title product as a white foam.

Step 8: N-carboethoxy-(10,11-dihydrospiro-5H-dibenzo[a,d]cycloheptene)-5,4'-piperidine (108)

N-methyl-(10,11-dihydro-5H-dibenzo[a,d]cycloheptene)-5,4'-piperidine (107, 1.38 g, 5 mmol) was suspended in 80 mL of ethyl chloroformate. The mixture was refluxed for 24 hours. The reaction solution was evaporated to dryness and the resulting residue was partitioned between ethyl acetate and saturated aqueous sodium bicarbonate. The phases were separated and the water layer was extracted with ethyl acetate (2×). The combined organic layers were washed with brine, dried over sodium sulfate, filtered, and evaporated to dryness. The resulting oil was purified by chromatography on silica gel (95:5 of methylene chloride:ethyl ether). The product fractions were evaporated to dryness to yield the title product as a white foam.

Step 9: 10,11-dihydrospiro-5H-dibenzo[a,d]cycloheptene-5,4'-piperidine (109), hydrochloride N-carboethoxy-(10,11-dihydrospiro-5H-dibenzo[a,d]cycloheptene)-5,4'-piperidine (108, 200 mg, 0.60 mmol) was dissolved in 8 mL of n-butanol and then treated with 1.1 g of potassium hydroxide. The resulting mixture was refluxed for 1.5 hours, cooled, and evaporated to dryness. The resulting residue was partitioned between ethyl acetate and saturated aqueous sodium bicarbonate. The phases were separated and the water layer was extracted with ethyl acetate (2×) The combined organic layers were washed with brine, dried over sodium sulfate, filtered, and evaporated to dryness. The resulting residue was treated with HCl/ethyl acetate, filtered, washed with ethyl ether to yield the hydrochloride of the title compound as a white solid.

m.p.: >275° C.

NMR: consistent with structure

HPLC: 97% pure

FAB MS: M+H @ m/e=264.09

Anal. cal'd for C19H21N.HCl.0.60 H2O: C, 73.45; H, 7.53; N, 4.51. Found: C, 73.44; H, 7.21; N, 4.31.

EXAMPLE 55

1'-(3-aminopropyl)-(10,11-dihydrospiro-5H-dibenzo[a,d]cycloheptene)-5,4'-piperidine (111) dihydrochloride

Step 1: 1'-(3-t-Butoxycarbonylaminopropyl)-(10,11-dihydrospiro-5H-dibenzo[a,d]cycloheptene)-5,4'-piperidine (110)

10,11-Dihydrospiro-5H-dibenzo[a,d]cycloheptene-5,4'-piperidine (109, 256 mg, 0.97 mmol) and N-Boc-3-bromopropylamine (346 mg, 1.45 mmol) were combined in DMF. The reaction mixture was treated with triethylamine (240 mL, 1.72 mmol) and warmed to 50° C. for 5 hours. The reaction solution was evaporated to dryness and the resulting residue was partitioned between ethyl acetate and saturated aqueous sodium bicarbonate. The phases were separated and the organic phase was washed with saturated aqueous sodium bicarbonate and brine, dried over sodium sulfate, filtered, and evaporated to dryness. The resulting oil was purified by chromatography on silica gel (96:4 of methylene chloride:methanol). The product fractions were evaporated to dryness to yield the title product as a yellow foam.

Step 2: 1'-(3-Aminopropyl)-(10,11-dihydrospiro-5H-dibenzo[a,d]cycloheptene)-5,4'-piperidine (111) dihydrochloride 1'-(3-t-Butoxycarbonylaminopropyl)-(10,11-dihydrospiro-5H-dibenzo[a,d]cycloheptene)-5,4'-piperidine (110) (340 mg, 0.81 mmol) in 2 mL of ethyl acetate and cooled in an ice bath. The solution was treated with 5 mL of saturated HCl/ethyl acetate solution and allowed to stir for 30 minutes. The mixture was evaporated in vacuo and the resulting residue was filtered from ethyl acetate and washed with ethyl ether to yield the dihydrochloride of the title compound as a white solid.

m.p.: 114–198° C. (foam)

NMR: consistent with structure

HPLC: 95% pure

FAB MS: M+H @ m/e=321

Anal. cal'd for C22H25N2.2HCl.1.15 H2.0.35 EtOAc: C, 63.16; H, 7.95; N, 6.30. Found: C, 63.19; H, 7.71; N, 6.15.

EXAMPLE 56

1,2,3,6-tetrahydro-1-[3-((10,11-dihydrospiro-5H-dibenzo[a,d]cycloheptene-5,4'-piperidin)-1'-yl)propylaminocarbonyl]-5-methoxycarbonyl-4-methoxymethyl-6(S)-(3,4-difluorophenyl)-2-oxopyrimidine (112), hydrochloride 1'-(3-Aminopropyl)-(10,11-dihydrospiro-5H-dibenzo[a,d]cycloheptene)-5,4'-piperidine (111), dihydrochloride (78 mg, 0.24 mmol), 5-methoxycarbonyl-4-methoxymethyl-1,2,3,6-tetrahydro-2-oxo-6(S)-(3,4-difluorophenyl)-1-[(4-nitrophenyloxy)carbonyl]pyrimidine (116 mg, 0.24 mmol), and triethylamine (42 mL, 0.30 mmol) were combined in 4 mL of THF, stirred at ambient temperature for 18 hours, then concentrated in vacuo. The resulting oil was purified by chromatography on silica gel eluted with 95:5 of methylene chloride:ethyl ether followed by 99:1, 98:2, and 95:5 of methylene chloride:methanol. The product fractions were evaporated to dryness. The resulting residue was treated with HCl/ethyl acetate and evaporated to dryness, and the residue reconcentrated from ethyl ether, then triturated with ethyl ether and filtered to give the hydrochloride of the title compound.

m.p.: 126–150° C. (foam)

NMR: consistent with structure

HPLC: 96% pure

FAB MS: M+H @ m/e=659.38

Anal. cal'd for C32H40F2N4O5.HCl.1.15 H2O.0.10 Et2O: C, 62.10; H, 6.17; N, 7.75. Found: C, 62.09; H, 6.14; N, 7.62.

EXAMPLE 57

1'-{3-[4(S)-(3,4-difluorophenyl)-2-oxooxazolidin-3-carbonylamino]-propyl}-(10,11-dihydrospiro-5H-dibenzo[a,d]cycloheptene)-5,4'-piperidine (113), hydrochloride The title compound was prepared by the method of Example 56 with 3-(p-nitrophenoxycarbonyl)-(4S)-(3,4-difluorophenyl)oxazolidin-2-one (92 mg, 0.25 mmol) substituted for 5-methoxycarbonyl-4-methoxymethyl-1,2,3,6-tetrahydro-2-oxo-6(S)-(3,4-difluorophenyl)-1-(4-nitrophenyloxycarbonyl)-pyrimidine.

m.p.: 146–177° C. (foam)

NMR: consistent with structure

HPLC: 97% pure

FAB MS: M+H @ m/e=546.16

Anal. cal'd for C32H33F2N3O3.HCl.1.10 H2O.0.15 Et2O: C, 63.87; H, 6.20; N, 6.86. Found: C, 63.86; H, 6.17; N, 6.76.

EXAMPLE 58

1'-{5-[4(S)-(3,4-difluorophenyl)-2-oxooxazolidin-3-yl]-pentyl}-(10,11-dihydrospiro-5H-dibenzo[a,d]cycloheptene)-5,4'-piperidine (114), hydrochloride (10,11-Dihydrospiro-5H-dibenzo[a,d]cycloheptene)-5,4'-piperidine (109, 60 mg, 0.23 mmol), 3-(5-bromopentyl)-4(S)-(3,4-difluorophenyl)-oxazolidin-2-one (80 mg, 0.23 mmol), and triethylamine (49 mL, 0.35 mmol) were combined in 3 mL of DMF and stirred at ambient temperature for 18 hours. The reaction was concentrated in vacuo, and the resulting residue was partitioned between ethyl acetate and saturated aqueous sodium bicarbonate. The phases were separated and the organic phase was washed with saturated aqueous sodium bicarbonate and brine, dried over sodium sulfate, filtered, and evaporated to dryness. The resulting oil was purified by chromatography on silica gel (98:2, 97:3, 96:4 and 95:5 of methylene chloride:methanol). The product fractions were evaporated to dryness. The resulting residue was converted to the hydrochloride salt by treatment with HCl/ethyl acetate and evaporation to dryness. The residue was reconcentrated from ethyl ether, then triturated with ethyl ether and filtered to give the hydrochloride of the title compound as a white solid.

m.p.: 232–236° C. (foam)

NMR: consistent with structure

HPLC: 100% pure

FAB MS: M+H @ m/e=531.37

Anal. cal'd for C33H36F2N2O2.HCl.H2O: C, 67.73; H, 6.72; N, 4.79. Found: C, 67.63; H, 6.47; N, 4.62.

EXAMPLE 59

As a specific embodiment of an oral composition, 100 mg of compound 99 (Example 53) is formulated with sufficient finely divided lactose to provide a total amount of 580 to 590 mg to fill a size O hard gel capsule.

EXAMPLE 60

Screening Assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 61

Selective Binding Assays

Membranes prepared from stably transfected human alpha 1d and alpha 1b cell lines (ATCC CRL 11138 and CRL 11139, respectively) were used to identify compounds that selectively bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

The compounds of the present invention prepared in the foregoing examples were found to have alpha 1a Ki values of less than about 150 nM as determined via the screening assay described in Example 60.

All of the compounds of the invention prepared in the foregoing examples were further found to exhibit selectivity in binding to alpha 1a receptors versus binding to the alpha 1b and alpha 1d receptors, as determined via the selective binding assay described in the preceding paragraph. The compounds of the invention prepared in Examples 3, 4, 6, 8, 10, 11, 14, 19, 20, 26, 27, 32, 33, 35, 36, 40, 42, 44, 46, 48, 49, 52, 53, 57 and 58 were found to be at least about 10-fold more selective in binding to alpha 1a receptors versus binding to the alpha 1b and 1d receptors.

The compounds of the invention prepared in Examples 4, 6, 8, 10, 14, 26, 27, 32, 33, 35, 40, 42, 44, 49, 53, 57 and 58 were found to have alpha 1a Ki values of less than about 20 nM and were also found to be at least about 30-fold more selective in binding to alpha 1a receptors versus binding to the alpha 1b and 1d receptors.

EXAMPLE 62

Counterscreen: Histamine-1 Selectivity

The binding affinity (Ki in nM) of the compounds of the present invention for histamine H1 receptors can determined via the binding assay described in Chang et al., *J. Neurochem.* (1979), 32: 1653, or as described in U.S. Pat. No. 5,403,847, or suitable modifications thereof known to those skilled in the art. The assay can be used to eliminate agents which specifically affect binding to hH1 receptors.

EXAMPLE 63

Exemplary Counterscreens

1. Assay Title: Dopamine D2, D3, D4 in vitro Screen

Objective of the Assay

The objective of this assay is to eliminate agents which specifically affect binding of [$^3$H] spiperone to cells expressing human dopamine receptors D2, D3 or D4.

Method

Modified from VanTol et al., *Nature* (1991), 350: 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl$_2$, KCl, NaCl, CaCl$_2$ and ascorbate to give a 1 Mg/mL suspension. The assay is initiated by adding 50–75 µg membranes in a total volume of 500 µl containing 0.2 nM [$^3$H]-spiperone. Non-specific binding is defined using 10 µM apomorphine. The assay is terminated after a 2 hour incubation at room temperature by rapid filtration over GF/B filters presoaked in 0.3% PEI, using 50 mM Tris-HCl pH 7.4.

2. Assay Title: Serotonin 5HT1a
Objective of the Assay

The objective of this assay is to eliminate agents which specifically affect binding to cloned human 5HT1a receptor Method Modified from Schelegel and Peroutka, *Biochemical Pharmacology* (1986), 35: 1943–1949.

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [$^3$H]8-OH-DPAT (8-hydroxy-2-dipropylamino-1,2,3,4-tetrahydronaphthalene) in 50 mM Tris-HCl, 4 mM $CaCl_2$ and 1 mg/ml ascorbate. Non-specific binding is defined using 10 $\mu$M propranolol. The assay is terminated after a 1 hour incubation at room temperature by rapid filtration over GF/Cfilters

EXAMPLE 64

Exemplary Functional Assays

In order to confirm the specificity of compounds for the human alpha 1a adrenergic receptor and to define the biological activity of the compounds, the following functional tests may be performed:

1. In vitro Rat, Dog and Human Prostate and Dog Urethra

Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 $\mu$M (for rat), 10 $\mu$M (for dog) and 20 $\mu$M (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. $pA_2$ (–log $K_b$) values were obtained from Schild plot when three or more concentrations were tested. When less than three concentrations of antagonist are tested, $K_b$ values are calculated according to the following formula $$K_b = [B]/x - 1$$

where x is the ratio of $EC_{50}$ of agonist in the presence and absence of antagonist and [B] is the antagonist concentration.

2. Measurement of Intra-Urethral Pressure in Anesthetized Dogs

PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha-1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 m/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four parameter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A compound of formula:

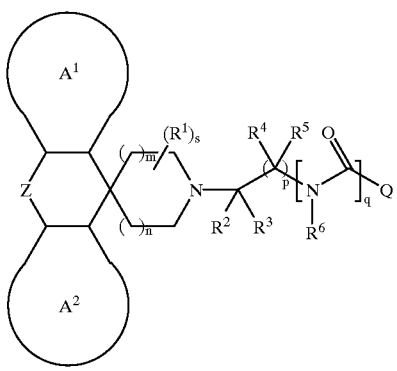

wherein Q is

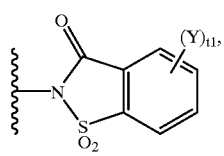 (i)

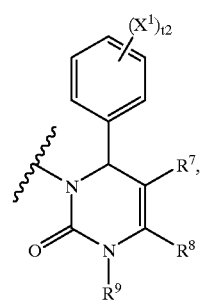 (ii)

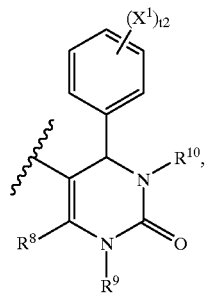 (iii)

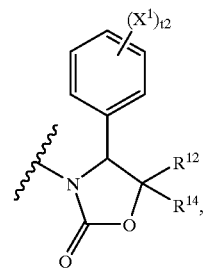 (iv)

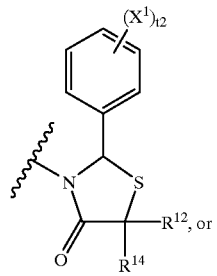 (v)

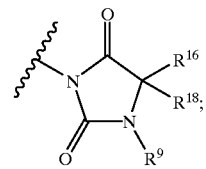 (vi)

$A^1$ is a benzene ring, substituted benzene, heterocyclic or substituted heterocyclic, wherein each of the substituents on substituted benzene or substituted heterocyclic is independently halogen, cyano, nitro, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalky;

$A^2$ independently has the same definition as set forth for $A^1$;

Z is $C(R^bR^c)C(R^bR^c)$, $C(R^b)=C(R^c)$, $C(R^bR^c)C(=O)$, or $C(=O)C(R^bR^c)$;

each Y is independently hydrogen, halogen, cyano, nitro, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalkyl;

each $X^1$ is independently hydrogen, halogen, cyano, nitro, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalkyl;

each $R^1$ is a substituent connected to a ring atom other than N or spiro substituted carbon and is independently hydrogen or $C_1$–$C_4$ alkyl;

$R^2$, $R^3$, $R^4$ and $R^5$ are each independently selected from hydrogen, $C_1$–$C_6$ alkyl, and $C_3$–$C_8$ cycloalkyl;

$R^6$ is hydrogen, $C_1$–$C_8$ alkyl, or fluorinated $C_1$–$C_8$ alkyl;

$R^7$ and $R^8$ are each independently selected from hydrogen, halogen, cyano, $C_1$–$C_6$ alkyl, $C_1$–$C_6$ alkoxy, fluorinated $C_1$–$C_6$ alkyl, fluorinated $C_1$–$C_6$ alkoxy, $CO_2R^d$, $C_2$–$C_8$ alkoxyalkyl, and fluorinated $C_2$–$C_8$ alkoxyalkyl;

$R^9$ and $R^{10}$ are each independently selected from hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, $C_4$–$C_{20}$ cycloalkylalkyl, or $CHR^eR^f$;

$R^{12}$ and $R^{14}$ are each independently selected from hydrogen, $C_1$–$C_6$ alkyl, $C_3$–$C_8$ cycloalkyl, $C_1$–$C_6$ alkoxy, fluorinated $C_1$–$C_6$ alkyl, fluorinated $C_1$–$C_6$ alkoxy, fluorinated $C_3$–$C_8$ cycloalkyl, $C_2$–$C_8$ alkoxyalkyl, and fluorinated $C_2$–$C_8$ alkoxyalkyl; or one of $R^{12}$ and $R^{14}$ is $CO_2R^d$ or $CON(R^e)_2$ and the other of $R^{12}$ and $R^{14}$ is as earlier defined; or $R^{12}$ and $R^{14}$ together with the carbon atom to which they are attached form $C_3$–$C_7$ cycloalkyl or substituted $C_3$–$C_7$ cycloalkyl, wherein the each of the substituents on substituted cycloalkyl is independently halogen, cyano, $C_1$–$C_6$ alkyl, fluorinated $C_1$–$C_6$ alkyl, $C_1$–$C_6$ alkoxy, fluorinated $C_1$–$C_6$ alkoxy, $CO_2R^d$, $C_2$–$C_8$ alkoxyalkyl, or fluorinated $C_2$–$C_8$ alkoxyalkyl;

$R^{16}$ and $R^{18}$ are each independently selected from hydrogen, $C_1$–$C_6$ alkyl, phenyl, substituted phenyl, naphthyl, substituted naphthyl, heterocyclic, and substituted heterocyclic, provided that $R^{16}$ and $R^{18}$ are not both hydrogen; wherein each of the substituents on substituted phenyl or substituted naphthyl is independently halogen, $C_1$–$C_6$ alkyl, fluorinated $C_1$–$C_6$ alkyl, $C_1$–$C_6$ alkoxy, fluorinated $C_1$–$C_6$ alkoxy, $CO_2R^d$, $C_2$–$C_8$ alkoxyalkyl, or fluorinated $C_2$–$C_8$ alkoxyalkyl; and wherein each of the substituents on substituted heterocyclic is independently halogen, $C_1$–$C_6$ alkyl, fluorinated $C_1$–$C_6$ alkyl, $C_1$–$C_6$ alkoxy, fluorinated $C_1$–$C_6$ alkoxy, $C_2$–$C_8$ alkoxyalkyl, fluorinated $C_2$–$C_8$ alkoxyalkyl, or phenyl;

$R^a$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, or $C_4$–$C_{20}$ cycloalkylalkyl;

$R^b$ and $R^c$ are each independently selected from hydrogen, $C_1$–$C_6$ alkyl, $C_3$–$C_6$ cycloalkyl, fluorinated $C_1$–$C_6$ alkyl, phenyl, and substituted phenyl, wherein each of the substituents on the substituted phenyl is independently halo, $C_1$–$C_6$ alkyl, fluorinated $C_1$–$C_6$ alkyl, $C_1$–$C_6$ alkoxy, fluorinated $C_1$–$C_6$ alkoxy, $CO_2R^d$, $C_2$–$C_8$ alkoxyalkyl, or fluorinated $C_2$–$C_8$ alkoxyalkyl;

$R^d$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, or $C_4$–$C_{20}$ cycloalkylalkyl;

$R^e$ is hydrogen or $C_1$–$C_6$ alkyl;

$R^f$ is phenyl or substituted phenyl, wherein each of the substituents on substituted phenyl is halogen, cyano, $C_1$–$C_6$ alkyl, fluorinated $C_1$–$C_6$ alkyl, $C_1$–$C_6$ alkoxy, fluorinated $C_1$–$C_6$ alkoxy, or $CO_2R^d$, $C_2$–$C_8$ alkoxyalkyl, or fluorinated $C_2$–$C_8$ alkoxyalkyl;

m and n are each independently integers from 0 to 3;

p is an integer from 1 to 5;

q is 0 or 1, provided that when Q is

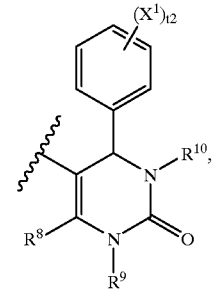

(iii)

then q is 0;

s is an integer from 0 to 4;

t1 is an integer from 0 to 4; and t2 is an integer from 0 to 5;

or a pharmaceutically acceptable salt thereof.

2. The compound according to claim 1, wherein $A^1$ is a benzene ring, substituted benzene ring, heteroaryl, or substituted heteroaryl;

$A^2$ independently has the same definition as set forth for $A^1$;

Z is $C(R^bR^c)C(R^bR^c)$, or $C(R^b)\!=\!C(R^c)$;

one of $R^2$ and $R^3$ is hydrogen and the other of $R^2$ and $R^3$ is hydrogen, $C_1$–$C_6$ alkyl, or $C_3$–$C_8$ cycloalkyl;

one of $R^4$ and $R^5$ is hydrogen and the other of $R^4$ and $R^5$ is hydrogen, $C_1$–$C_6$ alkyl, or $C_3$–$C_8$ cycloalkyl;

$R^{16}$ and $R^{18}$ are each independently selected from hydrogen, $C_1$–$C_6$ alkyl, phenyl, substituted phenyl, naphthyl, substituted naphthyl, heterocyclic, and substituted heterocyclic, provided that $R^{16}$ and $R^{18}$ are not both hydrogen; wherein each heterocyclic is independently pyridyl, thienyl, or furanyl; and m and n are each integers from 0 to 3, provided that the sum of m and n is an integer less than or equal to 3;

or a pharmaceutically acceptable salt thereof.

3. The compound according to claim 2, having the formula

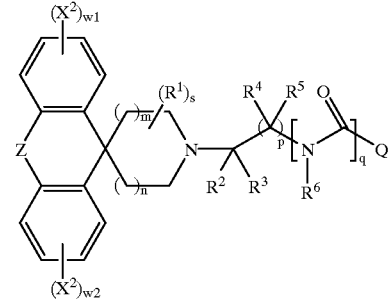

wherein

Z is $C(R^bR^c)C(R^bR^c)$;

each $X^2$ is independently hydrogen, halogen, cyano, $C_1$–$C_8$ alkyl, $C_1$–$C_6$ alkoxy, $C_3$–$C_8$ cycloalkyl, fluorinated $C_1$–$C_8$ alkyl, fluorinated $C_1$–$C_6$ alkoxy, fluorinated $C_3$–$C_8$ cycloalkyl, $C_2$–$C_8$ alkoxyalkyl, or fluorinated $C_2$–$C_8$ alkoxyalkyl; and w1 and w2 are each independently integers from 0 to 4; or a pharmaceutically acceptable salt thereof.

4. The compound according to claim 3, wherein Q is

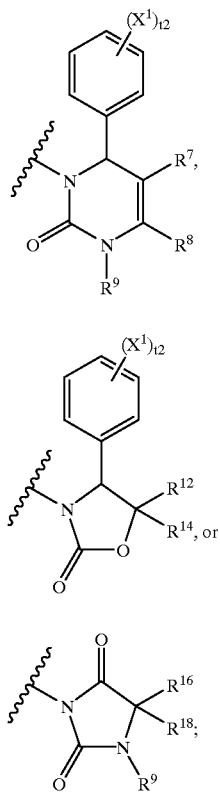

or a pharmaceutically acceptable salt thereof.

5. The compound according to claim 4, wherein the compound is of formula

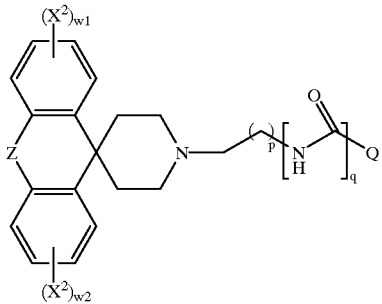

wherein

Z is $C(HR^b)C(HR^c)$, or $C(R^b)=C(R^c)$;

$R^7$ and $R^8$ are each independently selected from hydrogen, halogen, cyano, $C_1$–$C_4$ alkyl, $C_1$–$C_4$ alkoxy, $(CH_2)_{0-4}CF_3$, $OCF_3$, $CO_2R^d$, $(CH_2)_{1-4}OCH_3$, and $(CH_2)_{1-4}OCF_3$;

$R^9$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl;

$R^{12}$ and $R^{14}$ are each independently selected from hydrogen, $C_1$–$C_4$ alkyl, $C_3$–$C_6$ cycloalkyl, $C_1$–$C_4$ alkoxy, $(CH_2)_{0-4}CF_3$, $OCF_3$, fluorinated $C_3C_6$ cycloalkyl, $(CH_2)_{1-4}OCH_3$, $(CH_2)_{1-4}OCF_3$; or one of $R^{12}$ and $R^{14}$ $CO_2R^d$ or $CON(R^e)_2$ and the other of $R^{12}$ and $R^{14}$ is as earlier defined; or $R^{12}$ and $R^{14}$ together with the carbon atom to which they are attached form $C_3$–$C_7$ cycloalkyl;

one of $R^{16}$ and $R^{18}$ is hydrogen, $C_1$–$C_4$ alkyl, phenyl, mono- or di- or tri-substituted phenyl, naphthyl, mono- or di- or tri-substituted naphthyl, heterocyclic, or mono- or di- or tri-substituted heterocyclic; the other of $R^{16}$ and $R^{18}$ is phenyl, mono- or di- or tri-substituted phenyl, naphthyl, mono- or di- or tri-substituted naphthyl, heterocyclic, or mono- or di- or tri-substituted heterocyclic; wherein each of the substituents on substituted phenyl or substituted naphthyl or substituted heterocyclic is independently halogen, $C_1$–$C_4$ alkyl, $(CH_2)_{0-4}CF_3$, $C_1$–$C_4$ alkoxy, $OCF_3$, $CO_2R^d$, $(CH_2)_{1-4}OCH_3$, and $(CH_2)_{1-4}OCF_3$;

each $R^b$ and each $R^c$ is independently hydrogen, $C_1$–$C_4$ alkyl, $C_3$–$C_6$ cycloalkyl, $(CH_2)_{0-4}CF_3$, phenyl, or substituted phenyl, wherein each of the substituents on substituted phenyl is independently halogen, $C_1$–$C_4$ alkyl, $(CH_2)_{0-4}CF_3$, $C_1$–$C_4$ alkoxy, $OCF_3$, $CO_2R^d$, $(CH_2)_{0-4}OCH_3$, or $(CH_2)_{0-4}OCF_3$;

$R^d$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl;

$R^e$ is hydrogen or $C_1$–$C_4$ alkyl; and p is an integer from 2 to 5;

or a pharmaceutically acceptable salt thereof.

6. The compound according to claim 5, wherein the compound is selected from the group consisting of 1,2,3,6-tetrahydro-1-[3-((10,11-dihydrospiro-5H-dibenzo[a,d]cycloheptene-5,4'-piperidin)-1'-yl)propylaminocarbonyl]-5-methoxycarbonyl-4-methoxymethyl-6(S)-(3,4-difluorophenyl)-2-oxopyrimidine;

1'-{3-[4(S)-(3,4-difluorophenyl)-2-oxooxazolidin-3-carbonylamino]-propyl}-(10,11-dihydrospiro-5H-dibenzo [a,d]cycloheptene)-5,4'-piperidine;

1'-{5-[4(S)-(3,4-difluorophenyl)-2-oxooxazolidin-3-yl]-pentyl}-(10,11-dihydrospiro-5H-dibenzo[a,d]cycloheptene)-5,4'-piperidine;

and pharmaceutically acceptable salts thereof.

7. A pharmaceutical composition comprising a therapeutically effective amount of the compound according to claim 1 and a pharmaceutically acceptable carrier.

8. A pharmaceutical composition made by combining a therapeutically effective amount of the compound according to claim 1 and a pharmaceutically acceptable carrier.

9. A process for making a pharmaceutical composition comprising combining a therapeutically effective amount of the compound according to claim 1 and a pharmaceutically acceptable carrier.

10. The composition according to claim 7 further comprising a therapeutically effective amount of testosterone 5-alpha reductase inhibitor.

11. The composition according to claim 10, wherein the testosterone 5-alpha reductase inhibitor is a type 1, a type 2, both a type 1 and a type 2, or a dual type 1 and type 2 testosterone 5-alpha reductase inhibitor.

12. The composition according to claim 11, wherein the testosterone 5-alpha reductase inhibitor is a type 2 testosterone 5-alpha reductase inhibitor.

13. The composition according to claim 12, wherein the testosterone 5-alpha reductase inhibitor is finasteride.

14. A method of treating benign prostatic hyperplasia in a subject in need thereof which comprises administering to the subject a therapeutically effective amount of the compound according to claim 1.

15. The method according to claim 14, wherein the compound does not cause a fall in blood pressure at dosages effective to alleviate benign prostatic hyperlasia.

16. The method according to claim 14, wherein the compound is administered in combination with a therapeutically effective amount of a testosterone 5-alpha reductase inhibitor.

17. The method according to claim 16, wherein the testosterone 5-alpha reductase inhibitor is finasteride.

18. A method of treating benign prostatic hyperplasia in a subject in need thereof which comprises administering a therapeutically effective amount of the composition according to claim 7.

19. The method according to claim 18, wherein the composition further comprises a therapeutically effective amount of a testosterone 5-alpha reductase inhibitor.

20. A method of relaxing lower urinary tract tissue in a subject in need thereof which comprises administering to the subject a therapeutically effective amount of the compound according to claim 1.

21. The method according to claim 20, wherein the compound is administered in combination with a therapeutically effective amount of a testosterone 5-alpha reductase inhibitor.

22. The method according to claim 21, wherein the testosterone 5-alpha reductase inhibitor is finasteride.

23. A method of eliciting an alpha 1a antagonizing effect in a mammal in need thereof, comprising administering to the mammal a therapeutically effective amount of the compound according to claim 1.

* * * * *